US010551379B2

(12) United States Patent
Super et al.

(10) Patent No.: US 10,551,379 B2
(45) Date of Patent: Feb. 4, 2020

(54) METHODS AND COMPOSITIONS FOR IMPROVING DETECTION AND/OR CAPTURE OF A TARGET ENTITY

(71) Applicant: PRESIDENT AND FELLOWS OF HARVARD COLLEGE, Cambridge, MA (US)

(72) Inventors: Michael Super, Lexington, MA (US); Mark J. Cartwright, West Newton, MA (US); Martin M. Rottman, La Celle St Cloud (FR); Julie A. Tomolonis, Brighton, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 661 days.

(21) Appl. No.: 14/766,575

(22) PCT Filed: Mar. 14, 2014

(86) PCT No.: PCT/US2014/028683
§ 371 (c)(1),
(2) Date: Aug. 7, 2015

(87) PCT Pub. No.: WO2014/144325
PCT Pub. Date: Sep. 18, 2014

(65) Prior Publication Data
US 2015/0377881 A1 Dec. 31, 2015

Related U.S. Application Data

(60) Provisional application No. 61/788,570, filed on Mar. 15, 2013.

(51) Int. Cl.
*G01N 33/50* (2006.01)
*G01N 33/569* (2006.01)

(52) U.S. Cl.
CPC ....... *G01N 33/569* (2013.01); *G01N 2400/00* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 4,425,330 A | 1/1984 | Norcross et al. | |
| 5,137,810 A | 8/1992 | Sizemore | |
| 5,270,199 A | 12/1993 | Ezekowitz | |
| 5,273,884 A | 12/1993 | Gale et al. | |
| 5,405,832 A | 4/1995 | Potempa | |
| 5,474,904 A | 12/1995 | Potempa et al. | |
| 5,545,820 A | 8/1996 | Gatehouse | |
| 5,585,349 A | 12/1996 | Potempa | |
| 5,783,179 A | 7/1998 | Nestor, Jr. et al. | |
| 5,874,238 A | 2/1999 | Potempa et al. | |
| 5,951,976 A | 9/1999 | Segal | |
| 6,057,295 A | 5/2000 | Caretto et al. | |
| 6,117,977 A | 9/2000 | Lasky | |
| 6,225,046 B1 | 5/2001 | Vesey | |
| 6,376,473 B1 | 4/2002 | Audonnet et al. | |
| 6,471,968 B1 * | 10/2002 | Baker, Jr. ........... | A61K 41/0057 424/280.1 |
| 6,503,761 B1 | 1/2003 | Koenig | |
| 6,528,618 B1 | 3/2003 | Fridkin et al. | |
| 6,528,624 B1 | 3/2003 | Idusogie | |
| 6,562,784 B1 | 5/2003 | Thiel | |
| 6,703,219 B1 | 3/2004 | Potempa et al. | |
| 6,733,753 B2 | 5/2004 | Boone | |
| 6,846,649 B1 | 1/2005 | Thiel | |
| 6,900,292 B2 | 5/2005 | Sun | |
| 7,182,945 B2 | 2/2007 | Fridkin et al. | |
| 7,202,207 B2 | 4/2007 | Thiel | |
| 7,211,396 B2 | 5/2007 | Uttenthal | |
| 7,226,429 B2 | 6/2007 | Tullis | |
| 7,439,224 B2 | 10/2008 | Thiel | |
| 7,462,596 B2 | 12/2008 | Larsen | |
| 7,566,694 B2 | 7/2009 | Rider | |
| 7,629,440 B2 | 12/2009 | Segal et al. | |
| 7,695,937 B2 | 4/2010 | Baum | |

(Continued)

FOREIGN PATENT DOCUMENTS

| | | |
|---|---|---|
| EP | 0375736 B1 | 5/1998 |
| EP | 0861667 A2 | 8/2001 |

(Continued)

OTHER PUBLICATIONS

Steurer et al., "Ex Vivo Coating of Islet Cell Allografts with Murine CTLA4/Fc Promotes Graft Tolerance", The Journal of Immunology 155:1165-1174 (1995).
Stuart et al., "Mannose-Binding Lectin-Deficient Mice Display Defective Apoptotic Cell Clearance but No Autoimmune Phenotype", The Journal of Immunology 174:3220-3226 (2005).
Takahashi et al., "Mannose-binding lectin and its associated proteases (MASPs) mediate coagulation and its deficiency is a risk factor in developing complications from infection, including disseminated intravascular coagulation", Immunobiology 216(1-2):96-102 (2011).
Terai et al., "Relationship between gene polymorphisms of mannose-binding lectin (MBL) and two molecular forms of MBL", European Journal of Immunology 33:2755-2763 (2003).

(Continued)

*Primary Examiner* — Gary Counts
(74) *Attorney, Agent, or Firm* — Nixon Peabody LLP; David S. Resnick; Nicole D. Kling

(57) ABSTRACT

Methods, compositions, kits and systems for detecting and/or capturing a target entity in a sample are disclosed. In particular, the methods, compositions and kits described herein can be used for pretreatment of target-binding agents with a blocking agent to reduce non-target binding in a complex matrix (e.g., blood). Methods and compositions for detecting and/or capturing a microbe in a test sample, including bodily fluids such as blood and tissues of a subject, food, water, and environmental surfaces are also disclosed.

14 Claims, 4 Drawing Sheets
Specification includes a Sequence Listing.

(56) References Cited

U.S. PATENT DOCUMENTS

| | | | |
|---|---|---|---|
| 7,763,436 B2 | 7/2010 | Das | |
| 8,013,120 B2 | 9/2011 | Du Clos et al. | |
| 8,080,245 B2 | 12/2011 | Visintin | |
| 8,084,275 B2 | 12/2011 | Hirai | |
| 8,088,596 B2 | 1/2012 | Zeng | |
| 8,415,118 B2 | 4/2013 | Huang | |
| 8,598,324 B2 | 12/2013 | Rider | |
| 9,150,631 B2 * | 10/2015 | Super | C07K 14/4726 |
| 9,644,021 B2 | 5/2017 | Wang et al. | |
| 2003/0162248 A1 | 8/2003 | Wakamiya | |
| 2003/0166878 A1 | 9/2003 | Nishiya | |
| 2003/0180814 A1 | 9/2003 | Hodges et al. | |
| 2004/0018611 A1 | 1/2004 | Ward et al. | |
| 2004/0229212 A1 | 11/2004 | Thiel | |
| 2005/0014932 A1 | 1/2005 | Imboden | |
| 2005/0037949 A1 | 2/2005 | O'Brien | |
| 2006/0040362 A1 | 2/2006 | Wakamiya | |
| 2006/0104975 A1 | 5/2006 | Geijtenbeek | |
| 2006/0177879 A1 | 8/2006 | Mayes | |
| 2006/0188963 A1 | 8/2006 | Kongerslev | |
| 2006/0251580 A1 | 11/2006 | Keppler | |
| 2007/0031819 A1 | 2/2007 | Koschwanez et al. | |
| 2007/0049532 A1 | 3/2007 | Feige et al. | |
| 2007/0072247 A1 | 3/2007 | Wong | |
| 2007/0122850 A1 | 5/2007 | Teng et al. | |
| 2007/0184463 A1 | 8/2007 | Molho et al. | |
| 2007/0224640 A1 | 9/2007 | Caldwell | |
| 2007/0231833 A1 | 10/2007 | Arcidiacono et al. | |
| 2007/0269818 A1 | 11/2007 | Savage | |
| 2008/0014576 A1 | 1/2008 | Jovanovich et al. | |
| 2008/0056949 A1 | 3/2008 | Lee et al. | |
| 2008/0108120 A1 | 5/2008 | Cho et al. | |
| 2008/0156736 A1 | 7/2008 | Hirai | |
| 2008/0182793 A1 | 7/2008 | Baum | |
| 2008/0193965 A1 | 8/2008 | Zeng | |
| 2008/0260738 A1 | 10/2008 | Moore | |
| 2008/0300188 A1 | 12/2008 | Yang et al. | |
| 2009/0078614 A1 | 3/2009 | Varghese et al. | |
| 2009/0175797 A1 | 7/2009 | Warren et al. | |
| 2009/0181041 A1 | 7/2009 | Holgersson | |
| 2009/0220932 A1 | 9/2009 | Ingber | |
| 2009/0252729 A1 | 10/2009 | Farrington et al. | |
| 2009/0269843 A1 | 10/2009 | Blume et al. | |
| 2009/0297516 A1 | 12/2009 | Mayo | |
| 2010/0044232 A1 | 2/2010 | Lin et al. | |
| 2010/0055675 A1 | 3/2010 | Kumamoto et al. | |
| 2010/0266558 A1 | 10/2010 | Zipori | |
| 2010/0323342 A1 | 12/2010 | Gomez et al. | |
| 2010/0323429 A1 | 12/2010 | Hu | |
| 2010/0331240 A1 | 12/2010 | Michelow | |
| 2011/0027267 A1 | 2/2011 | Kyneb | |
| 2011/0053145 A1 | 3/2011 | Takakura | |
| 2011/0053250 A1 | 3/2011 | Takakura | |
| 2011/0065095 A1 | 3/2011 | Kida et al. | |
| 2011/0159000 A1 | 6/2011 | Silverman | |
| 2011/0183398 A1 | 7/2011 | Dasaratha | |
| 2011/0281792 A1 | 11/2011 | Zion | |
| 2012/0100140 A1 | 4/2012 | Reyes et al. | |
| 2012/0164628 A1 | 6/2012 | Duffin | |
| 2013/0029428 A1 | 1/2013 | Kim et al. | |
| 2013/0035283 A1 | 2/2013 | Super et al. | |
| 2013/0072445 A9 | 3/2013 | Du Clos et al. | |
| 2014/0227723 A1 | 8/2014 | Ingber et al. | |
| 2014/0249087 A1 | 9/2014 | Warren et al. | |
| 2015/0173883 A1 | 6/2015 | Ingber et al. | |

FOREIGN PATENT DOCUMENTS

| | | |
|---|---|---|
| EP | 0915970 B1 | 9/2004 |
| EP | 1862541 A1 | 12/2007 |
| EP | 1812459 B1 | 3/2011 |
| JP | S54-18198 A | 2/1979 |
| JP | 2006-517512 A | 7/2006 |
| JP | 2008515389 A | 5/2008 |
| JP | 2010122205 A | 6/2010 |
| JP | 2010268800 A | 12/2010 |
| WO | 2000/006603 A1 | 2/2000 |
| WO | 2001/003737 A1 | 1/2001 |
| WO | 2002/032292 A2 | 4/2002 |
| WO | 2003/014150 A2 | 2/2003 |
| WO | 2003/054164 A2 | 7/2003 |
| WO | 2004/018698 A2 | 3/2004 |
| WO | 2005092925 A2 | 10/2005 |
| WO | 2006/018428 A2 | 2/2006 |
| WO | 2006/044650 A2 | 4/2006 |
| WO | 2007/001332 A2 | 1/2007 |
| WO | 2007/044642 A2 | 4/2007 |
| WO | 2007/111496 A1 | 10/2007 |
| WO | 2008/130618 A1 | 10/2008 |
| WO | 2009/040048 A2 | 4/2009 |
| WO | 2009/062195 A2 | 5/2009 |
| WO | 2009/119722 A1 | 10/2009 |
| WO | 2009/126346 A2 | 10/2009 |
| WO | 2011/084749 A1 | 7/2011 |
| WO | 2011/090954 A2 | 7/2011 |
| WO | 2011/091037 A2 | 7/2011 |
| WO | 2011/103144 A1 | 8/2011 |
| WO | 2012/019178 A2 | 2/2012 |
| WO | 2012/050874 A2 | 4/2012 |
| WO | 2012/100099 A2 | 7/2012 |
| WO | 2012/135834 A2 | 10/2012 |
| WO | 2012142515 A2 | 10/2012 |
| WO | 2013/012924 A2 | 1/2013 |
| WO | 2013/130875 A1 | 9/2013 |

OTHER PUBLICATIONS

Thiel et al., "A second serine protease associated with mannan-binding lectin that activates complement", Nature 386:506-510 (1997).

Vaccaro et al., "Engineering the Fc region of immunoglobulin G to modulate in vivo antibody levels", Nature Biotechnology 23(10):1283-1288 (2005).

Ward et al., "Characterization of Humanized Antibodies Secreted by Aspergillus niger", Applied and Environmental Microbiology 70(5):2567-2576 (2004).

Warwick et al., "Use of Quantitative 16S Ribosomal DNA Detection for Diagnosis of Central Vascular Catheter-Associated Bacterial Infection", Journal of Clinical Microbiology 42(4):1402-1408 (2004).

Witus et al., "Identification of Highly Reactive Sequences for PLP-Mediated Bioconjugation Using a Combinatorial Peptide Library", Journal of the American Chemical Society 132:16812-16817 (2010).

Wong et al., "Bioinspired self-repairing slippery surfaces with pressure-stable omniphobicity", Nature 477:443-447 (2011).

Wriggers et al., "Control of Protein Functional Dynamics by Peptide Linkers", Biopolymers (Peptide Science) 80:736-746 (2005).

Xia et al., "Combined microfluidic-micromagnetic separation of living cells in continuous flow", Biomed Microdevices 8:299-308 (2006).

Ye et al., "Surface display of a glucose binding protein", Journal of Molecular Catalysis B: Enzymatic 28:201-206 (2004).

Yung et al., "Micromagnetic-microfluidic blood cleansing device", Lab on a Chip 9:1171-1177 (2009).

Ilyas et al., "High Glucose Disrupts Oligosaccharide Recognition Function Via Competitive Inhibition: A Potential Mechanism for Immune Dysregulation in Diabetes Mellitus", Immunobiology 216(1-2):126-131 (2011).

Kjaer et al., "M-Ficolin Binds Selectively to the Capsular Polysaccharides of Streptococcus pneumoniae Serotypes 19B and 19C and of a Streptococcus mitis Strain", Infection and Immunity 81(2):452-459 (2013).

Zettner, "Principles of Competitive Binding Assays (Saturation Analyses). I. Equilibrium Techniques", Clinical Chemistry 19(7):699-705 (1973).

Zettner et al., "Principles of Competitive Binding Assays (Saturation Analyses). II. Sequential Saturation", Clinical Chemistry 20(1):5-14 (1974).

Arakawa et al., "Elution of antibodies from a Protein-A column by aqueous arginine solutions", Protein Expression and Purification 36:244-248 (2004).

(56) References Cited

OTHER PUBLICATIONS

Armour et al., "Recombinant human IgG molecules lacking Fcγ receptor I binding and monocyte triggering activities", European Journal of Immunology 29:2613-2624 (1999).).

Ashkenazi et al., "Immunoadhesins as research tools and therapeutic agents", Current Opinion in Immunology 9:195-200 (1997).

Azevedo et al., "Horseradish peroxidase: a valuable tool in biotechnology," Biotechnology Annual Review 9:199-247 (2003).

Bangs Laboratories, Inc., "Protein Coated Microspheres", Tech. Note #51 (1997). (4 pages).

Bayston et al., "Bacterial endotoxin and current concepts in the diagnosis and treatment of endotoxaemia", Journal of Medical Microbiology 31:73-83 (1990).

Bossola et al., "Circulating Bacterial-Derived DNA Fragments and Markers of Inflammation in Chronic Hemodialysis Patients", Clinical Journal of the American Society of Nephrology 4:379-385 (2009).

Brooks et al., "Expression and secretion of ficolin β by porcine neutrophils", Biochimica et Biophysica Acta 1624:36-45 (2003).

Brouwer et al., "Mannose-Binding Lectin (MBL) Facilitates Opsonophagocytosis of Yeasts but Not of Bacteria despite MBL Binding", The Journal of Immunology 180:4124-4132 (2008).

Chamow et al., "Immunoadhesins: principles and applications", Trends Biotechnology 14:52-60 (1996).

Chang et al., "Crystallization and Preliminary X-ray Analysis of a Trimeric Form of Human Mannose Binding Protein", Journal of Molecular Biology 241:125-127 (1994).

Chen et al., "Fabrication of an Oriented Fc-Fused Lectin Microarray through Boronate Formation", Angewandte ahemie International Edition 47:8627-8630 (2008).

Foster, "Immune Evasion by *Staphylococci*", Nature 3:948-958 (2005).

Fox et al., "Single amino acid substitutions on the surface of *Escherichia coli* maltose-binding protein can have a profound impact on the solubility of fusion proteins", Protein Science 10:622-630 (2001).

Frakking et al., "Safety and phamacokinetics of plasma-derived mannose-binding lectin (MBL) substitution in children with chemotherapy-induced neutropaenia", European Journal of Cancer 45:505-512 (2009).

Garred et al., "Mannose-binding lectin and its genetic variants", Genes and Immunity 7:85-94 (2006).

Gouin et al., "Multimeric Lactoside "Click Clusters" as Tools to Investigate the Effect of Linker Length in Specific Interactions with Peanut Lectin, Galectin-1, and -3", ChemBioChem 11:1430-1442 (2010).

Grogl et al., "Leishmania braziliensis: Protein, Carbohydrate, and Antigen Differences between Log Phase and Stationary Phase Promastigotes in Vitro", Experimental Parasitology 63:352-359 (1987).

Hinton et al., "Engineered Human IgG Antibodies with Longer Serum Half-lives in Primates", The Journal of Biological Chemistry 279(8):6213-6216 (2004).

Holmskov et al., "Affinity and kinetic analysis of the bovine plasma C-type lectin collectin-43 (CL-43) interacting with mannan", FEBS Letters 393:314-316 (1996).

Huang et al., "Porcine DC-SIGN: Molecular cloning, gene structure, tissue distribution and binding characteristics", Developmental and Comparative Immunology 33:464-480 (2009).

Hwang et al., "The Pepper Mannose-Binding Lectin Gene CaMBL1 Is Required to Regulate Cell Death and Defense Responses to Microbial Pathogens", Plant Physiology 155:447-463 (2011).

Idusogie et al., "Engineered Antibodies with Increased Activity to Recruit Complement", The Journal of Immunology 166:2571-2575 (2001).

Invivo Gen Insight, "IgG-Fc Engineering for Therapeutic Use", (2006). (4 pages).

Jack et al., "Mannose-binding lectin: targeting the microbial world for complement attack and opsonophagocytosis", Immunological Reviews 180:86-99 (2001).

Jarva et al., "*Streptococcus pneumoniae* Evades Complement Attack and Opsonophagocytosis by Expressing the pspC Locus-Encoded Hic Protein That Binds to Short Consensus Repeats 8-11 of Factor H", The Journal of Immunology 168:1886-1894 (2002).

Kang et al., "The human macrophage mannose receptor directs *Mycobacterium tuberculosis* lipoarabinomanan-mediated phagosome biogenesis", The Journal of Experimental Medicine 202(7):987-999 (2005).

Keen et al., "Interrelationship Between pH and Surface Growth of Nitrobacter", Soil Biology and Biochemistry 19(6):665-672 (1987).

Kehres, "A kinetic model for binding protein-mediated arabinose transport", Protein Science 1:1661-1665 (1992).

Krarup et al., "Simultaneous Activation of Complement and Coagulation by MBL-Associated Serine Protease 2", PLoS One 2(7):e623 (2007). (8 pages).

Linehan et al., "Endogenous ligands of carbohydrate recognition domains of the mannose receptor in murine macrophages, endothelial cells and secretory cells; potential relevance to inflammation and immunity", European Journal of Immunology 31:1857-1866 (2001).

Lo et al., "High level expression and secretion of Fc-X fusion proteins in mammalian cells", Protein Engineering 11(6):495-500 (1998).

Loosdrecht et al., "Influence of Interfaces on Microbial Activity", Microbiological Reviews 54(1):75-87 (1990).

Matsushita et al., "Activation of the Classical Complement Pathway by Mannose-binding Protein in Association with a Novel C1s-like Serine Protease", Journal of Experimental Medicine 176(6):1497-1502 (1992).

Michelow et al., "A Novel L-ficolin/Mannose-binding Lectin Chimeric Molecule with Enhanced Activity against Ebola Virus", The Journal of Biological Chemistry 285(32):24729-24739 (2010).

Nadesalingam et al., "Mannose-Binding Lectin Recognizes Peptidoglycan via the N-acetyl Glucosamine Moiety, and Inhibits Ligand-Induced Proinflammatory Effect and Promotes Chemokine Production by Macrophages", The Journal of Immunology 175:1785-1794 (2005).

Nakamura et al., "Characterization of the interaction between serum mannan-binding protein and nucleic acid ligands", Journal of Leukocyte Biology 86:737-748 (2009).

Neth et al., "Ehancement of Complement Activation and Opsonophagocytosis by Complexes of Mannose-Binding Lectin with Mannose-Binding Lectin-Associated Serine Protease After Binding to *Staphylococcus aureus*", The Journal of Immunology 169:4430-4436 (2002).

Neth et al., "Mannose-Binding Lectin Binds to a Range of Clinically Relevant Microorganisms and Promotes Complement Deposition", Infection and Immunity 68(2):688-693 (2000).

Nisnevitch et al., "The solid phase in affinity chromatography: strategies for antibody attachment", Journal of Biochemical and Biophysical Methods 49:467-480 (2001).

Ogden et al., "C1q and Mannose Binding Lectin Engagement of Cell Surface Calreticulin and CD91 Initiates Macropinocytosis and Uptake of Apoptotic Cells", The Journal of Experimental Medicine 194(6):781-795 (2001).

Perham, "Domains, Motifs, and Linkers in 2-Oxo Acid Dehydrogenase Multienzyme Complexes: A Paradigm in the Design of a Multifunction Protein", Biochemistry 30(35):8501-8512 (1991).

Rutishauser et al., "Amino Acid Sequence of the Fc Region of a Human γG Immunoglobulin", Biochemistry 61:1414-1421 (1968).

Safarik et al., "The application of magnetic separations in applied microbiology", Journal of Applied Bacteriology 78:575-585 (1995).

Schmidt, "Fusion proteins as biopharmaceuticals—Applications and challenges", Current Opinion in Drug Discovery & Development 12(2):284-295 (2009).

Sheriff et al., "Human mannose-binding protein carbohydrate recognition domain trimerizes through a triple alpha-helical coiled-coil", Nat Struct Biol 1(11) 789-794 (1994).

Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry 276(9):6591-6604 (2001).

(56) References Cited

OTHER PUBLICATIONS

Sibille et al., "Comparison of serological tests for the diagnosis of feline immunodeficiency virus infection of cats", Veterinary Microbiology 45:259-267 (1995).
Sprong et al., "Mannose-Binding Lectin Is a Critical Factor in Systemic Complement Activation during Meningococcal Septic Shock", Clinical Infectious Diseases 49:1380-1386 (2009).
Cooper "A generic pathogen capture technology for sepsis diagnosis," pp. 1-127, Aug. 11, 2013, Article retrieved from the internet. <http://hdl.handle.net/1721.1/83966>.
Agrawal et al., "C-reactive protein mutant that does not bind to phosphocholine and pneumococcal C-polysaccharide", J. Immunol. 169(6):3217-3222 (2002).
Barnum et al., "Comparative Studies on the Binding Specificities of C-Reactive Protein (CRP) and HOPC 8", Annals of the New York Academy of Sciences 389:431-434 (1982).
Casey et al., "The acute-phase reactant C-Reactive protein binds to phosphorylcholine-expressing Neisseria meningitidis and increased uptake by human phagocytes", Infection and Immunity 76(3): 12998-1304 (2008).
Castle et al., "The binding of 125I-labeled concanavalin A to the cell surface of rabbit peritoneal polymorphonuclear leucocytes." Biochemical Medicine 28(1):1-15 (1982).
Choma et al. "Design of a Heme-Binding Four-Helix Bundle" 116:856-865 (1994).
Chuang et al., "Computational prediction of N-linked glycosylation incorporating structural properties and patterns," Bioinformatics. Sep. 1; 28(17): 2249-2255 (2012).
Culley et al., "C-reactive protein binds to phosphorylated carbohydrates", Glycobiology 10(1):59-65 (2000).
Czajkowsky et al., "Fc-fusion proteins: new developments and future perspectives", EMBO Mol Med., 4(10):1015-1028 (2012).
Dumont et al., "Monomeric Fc Fusions: Impact on Pharmacokinetic and Biological Activity of Protein Therapeutics", Biodrugs 20(3):151-160 (2006).
Feng et al., "Identification of carbohydrates on the surface membrane of pathogenic and nonpathogenic piscine haemoflagellates, Cryptobia salmositica, C. bullocki and C. catostomi (Kinetoplastida)." Diseases of Aquatic Organisms 32(3)201-209 (1998).
Hohenester, "Tackling the Legs of Mannan-Binding Lectin", Structure 19:1538-1540 (2011).

Huang et al., "Integrated microfluidic system for rapid screening of CRP aptamers utilizing systematic evolution of ligands by exponential enrichment (SELEX)", Biosensors and Bioelectronics 25:1761-1766 (2010).
Johnson et al. "Iron metabolism and the innate immune response to infection." Microbes and infection / Insitut Pasteur 14:207 (2012).
Lee et al., "Carbohydrate-binding properties of human neo-CRP and its relationship to phosphorylcholine-binding site", Glycobiology 13(1):11-21 (2003).
Lin et al. "Synergistic inflammation is induced by blood degradation products with microbial Toll-like receptor agonists and is blocked by hemopexin." The Journal of Infectious Diseases 202:624 (2010).
Mantuano et al., "The hemopexin domain of matrix metalloproteinase-9 activates cell signaling and promotes migration of schwann cells by binding to low-density lipoprotein receptor-related protein.", The Journal of Neuroscience 28(45)11571-11582 (2008).
Mauk et al. "An alternative view of the proposed alternative activities of hemopexin." Protein Science. 20:791 (2011).
Mold et al., "Binding of Human C-Reactive Protein to Bacteria", Infection and Immunity 38(1):392-395 (1982).
Presanis et al., "Biochemistry and genetics of mannan-binding lectin (MBL)", Biochemical Society Transactions 31(4):748-752 (2003).
Product Datasheet, "Human Mannan Binding Lectin peptide (237-248) (Carboxyterminal end) ab45655". Downloaded from the world wide web from abcam.com/Human-Mannan-Binding-Lectin-peptide-237-248-Carboxyterminal-end-ab45655.html on May 14, 2015.
Rouhandeh et al., "Surface membrane redistribution and stabilization of concanavalin A-specific receptors following Yaba tumor poxvirus infection." Biochimica et Biophysica Acta (BBA)-Biomembranes 600(2):301-312 (1980).
Shoulders et al., "Collagen structure and stability." Annual Review of Biochemistry 78(1):929-958 (2009).
Szalai, "The biological functions of C-reactive protein", Vascular Pharmacology 39:105-107 (2002).
Ying et al., "Soluble Monomeric IgG1 Fc", The Journal of Biological Chemistry 287(23):19399-19408 (2012).
Zhavnerko et al., "Oriented Immobilization of C-Reactive Protein on Solid Surface for Siosensor Applications", Frontiers of Multifunctional Integrated Nanosystems 95-108 (2004).

\* cited by examiner

Mannan-Glucose competition
(myOne AOB beads)

LPS-Glucose competition
(myOne AOB beads)

SEQUENCE LISTING

```
<160> NUMBER OF SEQ ID NOS: 8

<210> SEQ ID NO 1
<211> LENGTH: 248
<212> TYPE: PRT
<213> ORGANISM: Homo sapiens

<400> SEQUENCE: 1

Met Ser Leu Phe Pro Ser Leu Pro Leu Leu Leu Leu Ser Met Val Ala
1               5                   10                  15
```

```
Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
         35                  40                  45

Lys Asp Gly Arg Asp Gly Thr Lys Gly Glu Lys Gly Glu Pro Gly Gln
 50                  55                  60

Gly Leu Arg Gly Leu Gln Gly Pro Pro Gly Lys Leu Gly Pro Pro Gly
 65                  70                  75                  80

Asn Pro Gly Pro Ser Gly Ser Pro Gly Pro Lys Gly Gln Lys Gly Asp
                 85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245

<210> SEQ ID NO 2
<211> LENGTH: 228
<212> TYPE: PRT
<213> ORGANISM: Homo sapiens

<400> SEQUENCE: 2

Glu Thr Val Thr Cys Glu Asp Ala Gln Lys Thr Cys Pro Ala Val Ile
1               5                  10                  15

Ala Cys Ser Ser Pro Gly Ile Asn Gly Phe Pro Gly Lys Asp Gly Arg
            20                  25                  30

Asp Gly Thr Lys Gly Glu Lys Gly Glu Pro Gly Gln Gly Leu Arg Gly
        35                  40                  45

Leu Gln Gly Pro Pro Gly Lys Leu Gly Pro Pro Gly Asn Pro Gly Pro
 50                  55                  60

Ser Gly Ser Pro Gly Pro Lys Gly Gln Lys Gly Asp Pro Gly Lys Ser
 65                  70                  75                  80

Pro Asp Gly Asp Ser Ser Leu Ala Ala Ser Glu Arg Lys Ala Leu Gln
                 85                  90                  95

Thr Glu Met Ala Arg Ile Lys Lys Trp Leu Thr Phe Ser Leu Gly Lys
            100                 105                 110

Gln Val Gly Asn Lys Phe Phe Leu Thr Asn Gly Glu Ile Met Thr Phe
        115                 120                 125

Glu Lys Val Lys Ala Leu Cys Val Lys Phe Gln Ala Ser Val Ala Thr
```

```
                130                 135                 140
Pro Arg Asn Ala Ala Glu Asn Gly Ala Ile Gln Asn Leu Ile Lys Glu
145                 150                 155                 160

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
                180                 185                 190

Pro Asn Asn Ala Gly Ser Asp Glu Asp Cys Val Leu Leu Leu Lys Asn
                195                 200                 205

Gly Gln Trp Asn Asp Val Pro Cys Ser Thr Ser His Leu Ala Val Cys
                210                 215                 220

Glu Phe Pro Ile
225

<210> SEQ ID NO 3
<211> LENGTH: 141
<212> TYPE: PRT
<213> ORGANISM: Homo sapiens

<400> SEQUENCE: 3

Ala Ala Ser Glu Arg Lys Ala Leu Gln Thr Glu Met Ala Arg Ile Lys
1               5                   10                  15

Lys Trp Leu Thr Phe Ser Leu Gly Lys Gln Val Gly Asn Lys Phe Phe
                20                  25                  30

Leu Thr Asn Gly Glu Ile Met Thr Phe Glu Lys Val Lys Ala Leu Cys
                35                  40                  45

Val Lys Phe Gln Ala Ser Val Ala Thr Pro Arg Asn Ala Ala Glu Asn
50                  55                  60

Gly Ala Ile Gln Asn Leu Ile Lys Glu Glu Ala Phe Leu Gly Ile Thr
65                  70                  75                  80

Asp Glu Lys Thr Glu Gly Gln Phe Val Asp Leu Thr Gly Asn Arg Leu
                85                  90                  95

Thr Tyr Thr Asn Trp Asn Glu Gly Glu Pro Asn Asn Ala Gly Ser Asp
                100                 105                 110

Glu Asp Cys Val Leu Leu Leu Lys Asn Gly Gln Trp Asn Asp Val Pro
                115                 120                 125

Cys Ser Thr Ser His Leu Ala Val Cys Glu Phe Pro Ile
                130                 135                 140

<210> SEQ ID NO 4
<211> LENGTH: 115
<212> TYPE: PRT
<213> ORGANISM: Homo sapiens

<400> SEQUENCE: 4

Val Gly Asn Lys Phe Phe Leu Thr Asn Gly Glu Ile Met Thr Phe Glu
1               5                   10                  15

Lys Val Lys Ala Leu Cys Val Lys Phe Gln Ala Ser Val Ala Thr Pro
                20                  25                  30

Arg Asn Ala Ala Glu Asn Gly Ala Ile Gln Asn Leu Ile Lys Glu Glu
                35                  40                  45

Ala Phe Leu Gly Ile Thr Asp Glu Lys Thr Glu Gly Gln Phe Val Asp
                50                  55                  60

Leu Thr Gly Asn Arg Leu Thr Tyr Thr Asn Trp Asn Glu Gly Glu Pro
65                  70                  75                  80

Asn Asn Ala Gly Ser Asp Glu Asp Cys Val Leu Leu Leu Lys Asn Gly
```

```
                    85                  90                  95

Gln Trp Asn Asp Val Pro Cys Ser Thr Ser His Leu Ala Val Cys Glu
            100                 105                 110

Phe Pro Ile
        115

<210> SEQ ID NO 5
<211> LENGTH: 148
<212> TYPE: PRT
<213> ORGANISM: Homo sapiens

<400> SEQUENCE: 5

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln Val Gly Asn Lys Phe Phe Leu Thr Asn Gly Glu Ile Met Thr Phe
        35                  40                  45

Glu Lys Val Lys Ala Leu Cys Val Lys Phe Gln Ala Ser Val Ala Thr
    50                  55                  60

Pro Arg Asn Ala Ala Glu Asn Gly Ala Ile Gln Asn Leu Ile Lys Glu
65                  70                  75                  80

Glu Ala Phe Leu Gly Ile Thr Asp Glu Lys Thr Glu Gly Gln Phe Val
                85                  90                  95

Asp Leu Thr Gly Asn Arg Leu Thr Tyr Thr Asn Trp Asn Glu Gly Glu
            100                 105                 110

Pro Asn Asn Ala Gly Ser Asp Glu Asp Cys Val Leu Leu Leu Lys Asn
        115                 120                 125

Gly Gln Trp Asn Asp Val Pro Cys Ser Thr Ser His Leu Ala Val Cys
    130                 135                 140

Glu Phe Pro Ile
145

<210> SEQ ID NO 6
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
```

```
            115                 120                 125
Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Pro Asp Gly Asp Ser Ser Leu Ala
225                 230                 235                 240

Ala Ser Glu Arg Lys Ala Leu Gln Thr Glu Met Ala Arg Ile Lys Lys
                245                 250                 255

Trp Leu Thr Phe Ser Leu Gly Lys Gln Val Gly Asn Lys Phe Phe Leu
            260                 265                 270

Thr Asn Gly Glu Ile Met Thr Phe Glu Lys Val Lys Ala Leu Cys Val
        275                 280                 285

Lys Phe Gln Ala Ser Val Ala Thr Pro Arg Asn Ala Ala Glu Asn Gly
    290                 295                 300

Ala Ile Gln Asn Leu Ile Lys Glu Glu Ala Phe Leu Gly Ile Thr Asp
305                 310                 315                 320

Glu Lys Thr Glu Gly Gln Phe Val Asp Leu Thr Gly Asn Arg Leu Thr
                325                 330                 335

Tyr Thr Asn Trp Asn Glu Gly Glu Pro Asn Asn Ala Gly Ser Asp Glu
            340                 345                 350

Asp Cys Val Leu Leu Leu Lys Asn Gly Gln Trp Asn Asp Val Pro Cys
        355                 360                 365

Ser Thr Ser His Leu Ala Val Cys Glu Phe Pro Ile
    370                 375                 380

<210> SEQ ID NO 7
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95
```

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Pro Asp Gly Asp Ser
225                 230                 235                 240

Ser Leu Ala Ala Ser Glu Arg Lys Ala Leu Gln Thr Glu Met Ala Arg
                245                 250                 255

Ile Lys Lys Trp Leu Thr Phe Ser Leu Gly Lys Gln Val Gly Asn Lys
            260                 265                 270

Phe Phe Leu Thr Asn Gly Glu Ile Met Thr Phe Glu Lys Val Lys Ala
        275                 280                 285

Leu Cys Val Lys Phe Gln Ala Ser Val Ala Thr Pro Arg Asn Ala Ala
    290                 295                 300

Glu Asn Gly Ala Ile Gln Asn Leu Ile Lys Glu Glu Ala Phe Leu Gly
305                 310                 315                 320

Ile Thr Asp Glu Lys Thr Glu Gly Gln Phe Val Asp Leu Thr Gly Asn
                325                 330                 335

Arg Leu Thr Tyr Thr Asn Trp Asn Glu Gly Pro Asn Asn Ala Gly
            340                 345                 350

Ser Asp Glu Asp Cys Val Leu Leu Leu Lys Asn Gly Gln Trp Asn Asp
        355                 360                 365

Val Pro Cys Ser Thr Ser His Leu Ala Val Cys Glu Phe Pro Ile
    370                 375                 380

<210> SEQ ID NO 8
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

-continued

```
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Ala Thr Ser Lys Gln Val Gly Asn Lys
225                 230                 235                 240
Phe Phe Leu Thr Asn Gly Glu Ile Met Thr Phe Glu Lys Val Lys Ala
                245                 250                 255
Leu Cys Val Lys Phe Gln Ala Ser Val Ala Thr Pro Arg Asn Ala Ala
            260                 265                 270
Glu Asn Gly Ala Ile Gln Asn Leu Ile Lys Glu Glu Ala Phe Leu Gly
        275                 280                 285
Ile Thr Asp Glu Lys Thr Glu Gly Gln Phe Val Asp Leu Thr Gly Asn
    290                 295                 300
Arg Leu Thr Tyr Thr Asn Trp Asn Glu Gly Glu Pro Asn Asn Ala Gly
305                 310                 315                 320
Ser Asp Glu Asp Cys Val Leu Leu Leu Lys Asn Gly Gln Trp Asn Asp
                325                 330                 335
Val Pro Cys Ser Thr Ser His Leu Ala Val Cys Glu Phe Pro Ile
            340                 345                 350
```

METHODS AND COMPOSITIONS FOR IMPROVING DETECTION AND/OR CAPTURE OF A TARGET ENTITY

CROSS-REFERENCE TO RELATED APPLICATIONS

This application is a 35 U.S.C. § 371 National Phase Entry Application of International Application No. PCT/US2014/028683 filed Mar. 14, 2014, which designates the U.S., and which claims benefit under 35 U.S.C. § 119(e) of the U.S. Provisional Application No. 61/788,570 filed Mar. 15, 2013, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 6, 2015 is named 20150807_Sequence_Listing_002806-076402-US.txt and is 18,135 bytes in size.

TECHNICAL FIELD

Described herein relates generally to methods, compositions, and kits for detecting and/or capturing a target entity in a sample. In some embodiments, methods and compositions for detecting and/or capturing a microbe in a test sample, including bodily fluids such as blood and tissues of a subject, food, water, and environmental surfaces are also provided herein.

BACKGROUND

Sepsis is a major cause of morbidity and mortality in humans and other animals. In the United States, sepsis is the second leading cause of death in intensive care units among patients with non-traumatic illnesses. It is also the leading cause of death in young livestock, affecting 7.5-29% of neonatal calves, and is a common medical problem in neonatal foals. Despite the major advances of the past several decades in the treatment of serious infections, the incidence and mortality due to sepsis continues to rise.

Sepsis results from the systemic invasion of microorganisms into blood and can present two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and, often times, death.

Sepsis is a systemic reaction defined by the American College of Chest Physicians and the Society of Critical Care Medicine by a systemic inflammatory response (SIRS) in response to a confirmed infectious process. SIRS is defined by the presence of two or more of the following: altered body temperature (<36° C. or >38° C.), tachycardia (heart rate>90/min), tachypnea (respiratory rate>20/min) or hypocapnia ($P_aCO_2$ less than 4.3 kPa), leucopenia (white blood cells (WBCs)<4000 cells/mm$^3$ or leucocytosis (>12000 WBC/mm$^3$) or >10% band forms. The confirmation of the infectious process is confirmed by microbiological means (stain, culture, antigenemia or antigenuria, nucleic acid detection) or pathognomonic signs of infection obtained by imaging or clinical examination. The infection can affect any organ system, but the more severe cases present as septicemia (i.e., organisms, their metabolic end-products or toxins in the blood stream), bacteremia (i.e., bacteria in the blood), toxemia (i.e., toxins in the blood), and endotoxemia (i.e., endotoxin in the blood). Sepsis can also result from fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by various microorganisms.

There are three major types of sepsis characterized by the type of infecting organism. For example, gram-negative sepsis is the most frequently isolated (with a case fatality rate of about 35%). The majority of these infections are caused by *Escherichia coli, Klebsiella pneumoniae* and *Pseudomonas aeruginosa*. Gram-positive pathogens such as the Staphylococci and Streptococci are the second major cause of sepsis. The third major group includes fungi, with fungal infections causing a relatively small percentage of sepsis cases, but with a high mortality rate; these types of infections also have a higher incidence in immunocompromised patients.

Some of these infections can be acquired in a hospital setting and can result from certain types of surgery (e.g., abdominal procedures), immune suppression due to cancer or transplantation therapy, immune deficiency diseases, and exposure through intravenous catheters. Sepsis is also commonly caused by trauma, difficult newborn deliveries, and intestinal torsion (especially in dogs and horses). Infections in the lungs (pneumonia), bladder and kidneys (urinary tract infections), skin (cellulitis), abdomen (such as appendicitis), bone (osteomyeltitis) and joints (arthritis) and other areas (such as meningitis) can spread and also lead to sepsis. In some circumstances, ingestion of microbe-contaminated water, fluid or food, or contact with microbe-covered environmental surfaces can cause infections that lead to sepsis, and infection with food-borne and water-borne pathogens such as *Shigella* spp, or certain serotypes of *Escherichichia coli* (such as O157 H7), *Salmonella* spp including *Salmonella enterica serovar typhi* or *Listeria monocytogenes* can also lead to sepsis.

Many patients with septicemia or suspected septicemia exhibit a rapid decline over a 24-48 hour period. It has been reported that patients with septic shock require adapted treatment in less than 6 hours in order to benefit from antimicrobial therapy. Thus, rapid and reliable diagnostic and treatment methods are essential for effective patient care. Unfortunately, a confirmed diagnosis as to the type of infection, e.g., sepsis, traditionally requires microbiological analysis involving inoculation of blood cultures, incubation for 18-24 hours, plating the causative microorganism on solid media, another incubation period, and final identification 1-2 days later. Even with immediate and aggressive treatment, some patients can develop multiple organ dysfunction syndrome and eventually death. Hence, there remains a need for improved techniques for diagnosis of patients with infectious diseases, blood-borne infections, sepsis, or systemic inflammatory response syndrome. In addition, the ability to detect infectious pathogens in food, water, and/or environmental surfaces with improved specificity and thus decreased incidence of false positives would help providing appropriate and necessary treatments to patients who are in need and thus reducing healthcare cost.

SUMMARY

Embodiments of various aspects described herein are, at least in part, based on discovery of pre-treating a target-binding agent with an appropriate concentration of an intermediate-affinity ligand for the target-binding agent, prior to contacting a sample with the target-binding agent, so as to reduce non-target binding during capture of a target entity in the sample (e.g., blood). Unlike a typical blocking agent commonly used to saturate unoccupied binding sites on an interfering agent (non-target material), the inventors have discovered that pre-treating a microbe-binding agent comprising a mannan-binding domain (e.g., FcMBL, which is a fusion protein or peptide comprising a carbohydrate recognition domain of a mannan-binding lectin and a Fc portion of an immunoglobulin) with an intermediate-affinity blocking agent (e.g., glucose) can not only improve binding specificity and/or sensitivity of the microbe-binding agent for microbes and/or fragments thereof (target entity), but can also reduce false positives resulting from non-target binding (e.g., haemocyte binding). In one embodiment, glucose is selected as one of the blocking agents for use in the FcMBL system to detect and/or capture microbes or fragments thereof, partly because glucose can prevent non-target or interfering agents such as haemocytes from binding to FcMBL, while permitting a target entity such as microbes and/or fragments thereof to displace glucose that is bound to FcMBL.

The concept of pre-treatment of a target-binding agent with a blocking agent, where the blocking agent is selected based on relative binding affinities of the blocking agent, a target entity and an interfering agent, respectively, for the target-binding agent, can be extended to any detection/capture processes, assays, systems and/or platforms in which binding interaction between the target entity and the target-binding agent is involved in a sample comprising at least one interfering agent. The blocking agent used in these detection/capture processes, assays, systems and/or platforms can be selected to have an effective binding affinity for the target binding agent that is between an effective binding affinity of a target entity for the target-binding agent and the effective binding affinity of an interfering agent for the target-binding agent, so that the target entity, but not the interfering agent, can displace the blocking agent that is bound to the target-binding agent, and thus be captured on the target-binding agent. Accordingly, embodiments of various aspects described herein relate to methods, compositions and kits for detecting or capturing at least one target entity.

In one aspect, provided herein relates to methods of detecting or capturing at least one target entity. The method comprises contacting a sample with a composition comprising a target-binding agent and a blocking agent, wherein the blocking agent is selected for reducing the binding of at least one interfering agent present in the sample to the target-binding agent, while permitting a first target entity, if present in the sample, to (a) displace the blocking agent bound to the target-binding agent, or to (b) bind to the target-binding agent without the blocking agent bound thereto. In some embodiments, the blocking agent is bound to the target-binding agent within the composition, prior to contacting the sample with the composition.

In some embodiments of this aspect and other aspects described herein, the effective binding affinity of the blocking agent for the target-binding agent can be selected for increasing apparent specificity of the target-binding agent to the first target entity in the sample, as compared to the apparent specificity in the absence of the blocking agent. For example, the apparent specificity of the target-binding agent to the first target entity can be increased by reducing the binding of said at least one interfering agent to the target-binding agent, which can in turn increase the availability of binding sites on the target-binding agent for the target entity. While the binding of said at least one interfering agent to the target-binding agent is typically reduced by blocking the unoccupied binding sites on the interfering agent, the inventors instead pre-block or mask the binding sites on the target-binding agent with a blocking agent such that the interfering agent cannot bind to the target-binding agent, but the target entity is able to displace the blocking agent due to the target entity's higher affinity for the target-binding agent than that of the blocking agent. Thus, the target entity is bound to a sub-population of the target-binding agent, while a sub-population of the target-binding agent can still comprise the blocking agent bound thereto. The target entity can then be detected, for example, with a detection agent. In some embodiments, the blocking agent that is bound to the target-binding agent cannot bind to a detection agent and thus cannot interfere with detection of the target-binding agent bound with a target entity. In other embodiments, a blocking agent that is already bound to the target-binding agent can still bind to a detection agent. In these embodiments, the blocking agent can be treated, prior to addition of a detection gent, to mask its spare binding sites such that the blocking agent becomes unable to bind to the detection agent.

Accordingly, in some embodiments, the blocking agent can be selected based on its effective binding affinity relative to effective binding affinities of the first target entity and said at least one interfering agent, respectively, for the target-binding agent. In some embodiments, the blocking agent can be selected to have an effective binding affinity for the target-binding agent that is lower than an effective binding affinity of the first target entity for the target-binding agent; and the blocking agent is further selected to have the effective binding affinity for the target-binding agent that is higher than an effective binding affinity of at least one interfering agent present in the sample for the target-binding agent.

In order to permit the first target entity to displace the blocking agent bound to the target-binding agent, the effective binding affinity of the blocking agent for the target-binding agent is desired to be lower than the effective binding affinity of the first target entity for the target-binding agent. In some embodiments of this aspect and other aspects described herein, the effective binding affinity of the blocking agent for the target-binding agent can be lower than the effective binding affinity of the first target entity for the target-binding agent by at least about 10% or more, including, e.g., at least about 20%, at least about 30%, at least about 40%, at least about 50%, at least about 60%, at least about 70%, at least about 80%, at least about 90% or more.

In order to prevent at least one interfering agent from binding to the target-binding agent, the effective binding affinity of the blocking agent for the target-binding agent is desired to be higher than the effective binding affinity of said at least one interfering agent present in the sample for the target-binding agent. In some embodiments of this aspect and other aspects described herein, the effective binding affinity of the blocking agent for the target-binding agent can be higher than the effective binding affinity of said at least one interfering agent present in the sample for the target-binding agent by at least about 10% or more, including, e.g., at least about 20%, at least about 30%, at least about 40%, at least about 50%, at least about 60%, at least about 70%, at least about 80%, at least about 90% or more. In some embodiments, the effective binding affinity of the blocking agent for the target-binding agent can be higher than the effective binding affinity of said at least one interfering agent present in the sample for the target-binding agent by at least about 1-fold or more, including, e.g., at least about 2-fold, at least about 3-fold, at least about 4-fold, at least about 5-fold, at least about 6-fold, at least about 7-fold, at least about 8-fold, at least about 9-fold, at least about 10-fold or more.

In some embodiments of this aspect and other aspects described herein, the effective binding affinity of the blocking agent for the target-binding agent, as indicated by a dissociation constant for the binding of the blocking agent to the target-binding agent, can range from about 1 µM to about 100 mM, or about 10 µM to about 75 mM, or about 5 mM to about 50 mM. In one embodiment, the effective binding affinity of the blocking agent for the target-binding agent, as indicated by a dissociation constant for the binding of the blocking agent to the target-binding agent, can range from about 5 mM to about 50 mM. In some embodiments, the effective binding affinity of the blocking agent for the target-binding agent, as indicated by a dissociation constant for the binding of the blocking agent to the target-binding agent, can be in a nanomolar range. For example, in some embodiments, the effective binding affinity of the blocking agent for the target-binding agent, as indicated by a dissociation constant for the binding of the blocking agent to the target-binding agent, can range from about 1 nM to 10 µM, about 1 nM to about 1 µM, or about 10 nM to about 500 nM.

The blocking agent can be any molecule, compound, or agent that can bind to a target-binding agent with an effective binding affinity between that of the target entity and the interfering agent, respectively, for the target-binding agent. Depending on the binding properties of the target-binding agents, target entity, and/or interfering agents, the blocking agent can include, but not limited to, cells or fragments thereof, peptides, polypeptides, proteins, peptidomimetics, antibodies, antibody fragments (e.g., antigen binding fragments of antibodies), carbohydrate-binding protein, e.g., lectins, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, endotoxins (e.g., bacterial lipopolysaccharide), and any combinations thereof. In some embodiments, the cells include, but are not limited to, prokaryotes (e.g., microbes such as bacteria) and eukaryotes (e.g., animal cells, plant cells, yeasts, and fungi), blood cells, and any fragments thereof. In some embodiments where the target-binding agent is configured to recognize a carbohydrate pattern, e.g., for detection and/or capture of a microbe or a fragment thereof, the blocking agent can be a carbohydrate or a saccharide.

In some embodiments, the blocking agent can be a monomer, which has no free binding site after binding to the target-binding agent. Thus, the blocking agent cannot subsequently bind to a detection agent, and thus prevent its interference with an assay used to detect a target entity bound to a target-binding agent. For example, a saccharide-based monomeric blocking agent can be a monosaccharide or modification thereof.

In alternative embodiments, the blocking agent can be a multimer which has at least one free binding site after binding to the target-binding agent. In these embodiments, the blocking agent can subsequently bind to a detection agent and thus interfere in an assay used to detect a target entity bound to a target-binding agent. In these embodiments, the blocking agent can be treated, prior to addition of a detection agent, to mask all the free binding sites. In some embodiments, a saccharide-based multimeric blocking agent can be a disaccharide, an oligosaccharide, a polysaccharide, modifications thereof, or any combinations thereof.

Examples of a saccharide-based blocking agent include, without limitations, hexose (e.g., glucose), maltose, mannose, N-acetyl-muramic acid, amino sugars (e.g., galactosamine, glucosamine, sialic acid, N-acetylgludosamine), sulfosugars (e.g., sulfoquinovose), trehalose, cellobiose, lactose, lactulose, sucrose, fructo-oligosaccharides, cellulose, chitin, or any combinations thereof. In some embodiments, a saccharide-based blocking agent can be glucose, maltose, N-acetyl-muramic acid, or any combinations thereof. In one embodiment, a saccharide-based blocking agent can comprise glucose. In one embodiment, a saccharide-based blocking agent can comprise mannose.

The target entity can be any molecule, compound, or agent that can be detected and/or captured by a target-binding agent. Non-limiting examples of a target entity include, but are not limited to, cells or fragments thereof, peptides, polypeptides, proteins, peptidomimetics, antibodies, antibody fragments (e.g., antigen binding fragments of antibodies), carbohydrate-binding protein, e.g., lectins, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, endotoxins (e.g., bacterial lipopolysaccharide), and any combinations thereof. In some embodiments, the cells include, but are not limited to, prokaryotes (e.g., microbes such as bacteria) and eukaryotes (e.g., animal cells, plant cells, yeasts, and fungi), blood cells, and any fragments thereof. In some embodiments, the target entity can be a cell, e.g., but not limited to a microbe or a fragment thereof.

As described earlier, the effective binding affinity of the blocking agent for the target-binding agent is lower than the effective binding affinity of the target entity for the target-binding agent. Accordingly, in some embodiments of this aspect and other aspects described herein, the effective binding affinity of the first target entity for the target-binding agent, as indicated by a dissociation constant for the binding of the first target entity to the target-binding agent, can be less than 100 mM, less than 75 mM, less than 50 mM, less than 25 mM, less than 10 mM, less than 5 mM, less than 1 mM, less than 0.5 mM, less than 0.1 mM, less than 10 µM, less than 1 µM, or less, provided that the dissociation constant for the binding of the blocking agent to the target-binding agent is smaller than higher than that for the binding of the first target entity to the target-binding agent. In some embodiments, the effective binding affinity of the first target entity for the target-binding agent, as indicated by a dissociation constant for the binding of the first target entity to the target-binding agent, can be less than 25 mM. In some embodiments, the effective binding affinity of the first target entity for the target-binding agent, as indicated by a dissociation constant for the binding of the first target entity to the target-binding agent, can be in a nanomolar range. For example, in some embodiments, the effective binding affinity of the first target entity for the target-binding agent, as indicated by a dissociation constant for the binding of the first target entity to the target-binding agent, can be less than 1 µM, less than 500 nM, less than 100 nM, less than 50 nM, less than 25 nM, less than 10 nM, less than 5 nM, less than 1 nM, less than 0.5 nM, or less.

The target-binding agent is an agent configured to detect and/or capture at least one target entity. The target-binding agent can be present in any form, including but not limited to a target-binding molecule, and/or a target-binding substrate (e.g., a target-binding molecule conjugated to a solid substrate). In some embodiments, the target-binding agent can comprise a target-binding molecule selected from the group consisting of cells or fragments thereof, peptides, polypeptides, proteins, peptidomimetics, antibodies, antibody fragments (e.g., antigen binding fragments of antibodies), carbohydrate-binding protein, e.g., lectins, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, endotoxins (e.g., bacterial lipopolysaccharide), and any combinations thereof. In some embodiments, the target-binding agent can be configured to detect and/or capture at least one microbe and/or a fragment thereof. Thus, in some embodiments, the target-binding agent can comprise a microbe-binding agent. By way of example only, a microbe-binding agent can comprise a lectin (e.g., a FcMBL molecule).

In some embodiments, the target-binding agent can be affixed to a solid substrate described herein. Non-limiting examples of a solid substrate include, but are not limited to, a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combinations thereof.

An interfering agent is an agent present in a sample to be assayed, which undesirably binds to a target-binding agent and reduces the effective binding affinity of the target-binding agent to the corresponding target entity. In some embodiments where the sample comprises a biological fluid, e.g., blood, at least one interfering agent can comprise a blood cell and/or a fragment thereof, e.g., a red blood cell (or an erythrocyte) and/or a fragment thereof. In some embodiments where the sample comprises a second target entity not intended to be captured or detected by the first target-binding agent, but by a second target-binding agent, the second target entity can be considered as an interfering agent with respect to the binding interaction between the first target-binding agent and the first target entity. In some embodiments, said at least one interfering agent can be a non-specific binding molecule. In some embodiments, said at least one interfering agent can be a molecule for which the target-binding agent has a binding specificity, but with a lower binding affinity than to the target entity.

As described herein, the effective binding affinity of said at least one interfering agent for the target-binding agent is lower than the effective binding affinity of the blocking agent for the target-binding agent. Accordingly, in some embodiments of this aspect and other aspects described herein, the effective binding affinity of said at least one interfering agent for the target-binding agent, as indicated by a dissociation constant for the binding of the interfering agent to the target-binding agent, can be more than 5 µM, more than 10 µM, more than 0.1 mM, more than 0.5 mM, more than 1 mM, more than 5 mM, more than 10 mM, more than 25 mM, more than 50 mM, more than 75 mM, more than 100 mM or more, provided that the dissociation constant for the binding of the interfering agent to the target-binding agent is larger than that for the binding of the blocking agent to the target-binding agent. In some embodiments, the effective binding affinity of said at least one interfering agent for the target-binding agent, as indicated by a dissociation constant for the binding of the interfering agent to the target-binding agent, can be more than 50 mM. In some embodiments, the effective binding affinity of said at least one interfering agent for the target-binding agent, as indicated by a dissociation constant for the binding of said at least one interfering agent to the target-binding agent, can be in a lower range, e.g., more than 500 nM, or more than 1 µM, or higher.

In some embodiments, the method can further comprise exposing the target-binding agent to the blocking agent at a pre-determined concentration to form the composition comprising the target-binding agent and the blocking agent bound thereto, prior to the contacting of the sample with the composition.

The blocking agent can be generally present in a sample at any concentration provided that its presence in the sample does not adversely affect the binding of the first target entity to the target-binding agent. In some embodiments, the blocking agent can be present in a pre-determined concentration that does not reduce the binding of the first target entity to the target-binding agent by more than 50%, no more than 40%, no more than 30% or less, as compared to the binding in the absence of the blocking agent. In some embodiments, the concentration ratio of the blocking agent to the target-binding agent can range from about 100:1 to about 10,000:1, from about 250:1 to about 7500:1, or from about 500:1 to about 5000:1. In some embodiments, the concentration ratio of the blocking agent to the target-binding agent can range from about 500:1 to about 5000:1. In some embodiments, the concentration ratio of the blocking agent to the target-binding agent can range from about 2:1 to about 100:1, from about 2:1 to about 50:1, or from about 5:1 to about 25:1. In some embodiments, the concentration ratio of the blocking agent to the target-binding agent can be at least about 100:1, at least about 1000:1, at least about 2500:1, at least about 5000:1, at least about 7500:1, or at least about 10,000:1.

In some embodiments, the blocking agent can be provided in the pre-determined concentration, which is sufficient to reduce the binding of said at least one interfering agent to the target-binding agent, e.g., by at least about 10%, at least about 20%, at least about 30%, at least about 40%, at least about 50%, at least about 60% or more, as compared to the binding in the absence of the blocking agent. Without wishing to be bound by theory, by reducing the binding of said at least one interfering agent to the target-binding agent, the binding sensitivity of the target binding agent for the corresponding target entity can be increased, e.g., due to a lower background noises contributed by the interfering agent. Accordingly, in some embodiments, the blocking agent can be provided in the pre-determined concentration, which is sufficient to decrease the lower limit of detection of the target-binding agent binding to the first target entity in the sample, e.g., by at least about 10%, at least about 20%, at least about 30%, at least about 40%, at least about 50%, at least about 60% or more, when compared to the lower limit of detection in the absence of the blocking agent.

In some embodiments, the concentration of the blocking agent in a sample can be selected to minimize non-specific binding (including, e.g., binding of interfering agent(s) to a target-binding agent) while minimizing inhibition of a target entity binding to a target-binding agent.

In some embodiments, the blocking agent can be set to a concentration that is determined based on, e.g., the matrix composition of a sample (e.g., a blood sample) and/or concentrations of interfering agent(s) in the sample. In some embodiments, the concentration of the blocking agent added can increase with the amount/concentration of interfering agents present in a sample. In some embodiments, the concentration of the blocking agent added can increase with the amount/concentration of interfering agent(s) present in a sample, while the amount/concentration of the target-binding agent remains about the same.

The pre-determined concentration of the blocking agent can vary with the effective binding affinity of the target entity for the target-binding agent. For example, a higher concentration of the blocking agent can be used without adversely affect the binding of the target-binding agent to the target entity with a higher effective binding affinity. In some embodiments, the pre-determined concentration of the blocking agent can range from about 1 mM to about 500 mM, or from about 5 mM to about 250 mM, or from about 10 mM to about 100 mM.

In some embodiments where the glucose is the blocking agent, the pre-determined concentration of glucose can range from about 5 mM to about 200 mM. In some embodiments, the pre-determined concentration of glucose can be less than 20 mM. In some embodiments, the pre-determined concentration of glucose can be more than 20 mM.

In some embodiments, the method can further comprise separating the target-binding agent from the sample after the contacting. For example, the target-binding agent in the form of magnetic particles (e.g., target-binding magnetic particles) can be separated from the sample after the contacting in the presence of a magnetic field gradient.

In some embodiments, the method can further comprise performing a competitive wash to release, if any, said at least one interfering agent that remains bound to the target-binding agent after the contacting and/or separation. For example, the target-binding agent after the contacting and/or separation can be further washed with a buffer comprising a blocking agent described herein so as to remove any residual interfering agents still bound to the target-binding agent. The blocking agent used in the wash buffer can be the same as, or different from, the one used during the capture of the target entity.

In some embodiments, the method can further comprise detecting the presence or absence of a target entity, after the sample is contacted with a composition comprising a target-binding agent and a blocking agent. The target entity, if present, can remain bound on the target-binding agent during the detection, or be detached from the target-binding agent prior to the detection. Methods for detecting the target entity are known in the art. For example, in some embodiments, the target entity can be detected by a method comprising contacting the bound or detached target entity with a detection agent.

In some embodiments, the method can further comprise detecting the displaced blocking agent. Without wishing to be bound by theory, the amount of the displaced blocking agent can be proportional to the amount of the target entity displacing the blocking agent. Accordingly, in some embodiments, rather than directly determining the amount of the target entity bound on the target-binding agent, the amount of the target entity can be also reflected by a measurement of the amount of the displaced blocking agent. To facilitate detection of the displaced blocking agent, in some embodiments, the blocking agent can comprise a detectable label, e.g., a fluorescent label.

Various embodiments of the methods described herein can be adapted to various applications or be integrated as part of a process, e.g., but not limited to, antibody-based assays (e.g., ELISA), filtrations, microbe detection and/or capture, antibiotic susceptibility testings, multiplexing assays, coating processes, hybridization-based assays, diagnostic strips, targeted drug delivery, or any combinations thereof. Thus, various compositions comprising a target-binding agent and at least one blocking agent can be formulated to suit the need of each individual application. Accordingly, another aspect provided herein relates to a composition comprising one or more embodiments of a target-binding agent described herein, and at least one embodiment of a blocking agent described herein at a pre-determined concentration, wherein the effective binding affinity of said at least one blocking agent for the target-binding agent is lower than the effective binding affinity of a target entity to be captured, and wherein the effective binding affinity of said at least one blocking agent for the target-binding agent is higher than the effective binding affinity of at least one interfering molecule present in a sample to be assayed for the target-binding agent.

In some embodiments, said at least one blocking agent can be pre-bound to the target-binding agent within the composition. In alternative embodiments, said at least one blocking agent and the target-binding agent can be kept separately within the composition, e.g., each is contained in a separate container. In some embodiments, the target-binding agent and said at least one blocking agent can each be independently present in a buffered solution.

In some embodiments, the composition can further comprise a solid substrate affixed with at least one target-binding agent. Examples of the solid substrate include, but are not limited to, a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combinations thereof. In some embodiments, the composition can comprise microparticle or a microbead (e.g., polymeric particle and/or magnetic particle) affixed with the target-binding agent. In some embodiments, the composition can comprise a dipstick affixed with the target-binding agent.

In some embodiments, the target-binding agent can comprise an antibody (e.g., a primary antibody, and/or a secondary antibody). In these embodiments, by way of example only, the composition can be used during immunoglobulin secondary detection reactions, immunostaining, and/or ELISA assay.

In some embodiments, the target-binding agent can comprise a microbe-binding agent (e.g., FcMBL molecule). Examples of microbe-binding agent for detection and/or capture of microbes and/or fragments thereof are known in the art, including, e.g., microbe-binding molecules disclosed herein and in the International Application Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), the content of which are incorporated herein by reference.

In some embodiments where the microbe-binding agent comprises a mannan-binding domain (e.g., FcMBL molecule), said at least one blocking agent can comprise glucose, maltose, N-acetyl muramic acid, and/or any combinations thereof. The pre-determined concentration of the blocking agent can vary with the binding affinity of the target entity for the target-binding agent. For example, a higher concentration of the blocking agent can be used without adversely affect the binding of the target-binding agent to the target entity with a higher effective binding affinity. In some embodiments where the glucose is the blocking agent, the pre-determined concentration of glucose can range from about 5 mM to about 200 mM.

In some embodiments, the blocking agent can further comprise a detectable label.

A kit comprising at least one composition described herein is also provided. In some embodiments, the kit comprises a first composition comprising a first target-binding agent and at least one first blocking agent at a first pre-determined concentration, wherein the effective binding affinity of said at least one first blocking agent for the first target-binding agent is lower than the effective binding affinity of a first target entity to be captured, and wherein the effective binding affinity of said at least one first blocking agent for the first target-binding agent is higher than the effective binding affinity of at least one first interfering molecule present in a sample to be assayed for the first target-binding agent; and instructions for using the composition for detecting or capturing the first target entity.

In some embodiments, the kit can further comprise a second composition comprising a second target-binding agent and at least one second blocking agent at a second pre-determined concentration, wherein the effective binding affinity of said at least one second blocking agent for the second target-binding agent is lower than the effective binding affinity of a second target entity to be captured, and wherein the effective binding affinity of said at least one second blocking agent for the second target-binding agent is higher than the effective binding affinity of at least one second interfering molecule present in the sample to be assayed for the second target-binding agent.

In some embodiments, the first blocking agent and the second blocking agent can be selected to prevent or reduce the binding of the same interfering agent to the first target-binding agent and the second target-binding agent, respectively. By way of example only, where said at least the first interfering agent and/or said at least the second interfering agent can be a non-specific binding molecule present in a sample, the first blocking agent and the second blocking agent can be selected to prevent or reduce the binding of non-specific binding molecules to the first target-binding agent and the second target-binding agent, respectively.

In some embodiments, the first blocking agent and the second blocking agent can be selected to prevent or reduce the binding of a different interfering agent to the first target-binding agent and the second target-binding agent, respectively. By way of example only, where the kit is adapted for use in a multiplexing assay, a first target entity can be intended to be detected by a first target-binding agent but not a second target-binding agent, while a second target entity can be intended to be detected by a second target-binding agent, but not a first target-binding agent. In these embodiments, the first target entity can be considered as said second interfering agent with respect to binding interaction between the second target-binding agent and the second target entity, and the second target entity can be considered as said first interfering agent with respect to binding interaction between the first target-binding agent and the first target entity.

In some embodiments, the first blocking agent can be pre-bound to the first target-binding agent. In some embodiments, the second blocking agent can be pre-bound to the second target-binding agent.

In some embodiments, the first target-binding agent can be affixed to a first solid substrate. In some embodiments, the first solid substrate can be further affixed with the second target-binding agent. In some embodiments, the second target-binding agent can be affixed to a second solid substrate. Non-limiting examples of the first or the second solid substrate includes, but are not limited to, a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combination thereof.

In some embodiments, the kit can further comprise a first detection agent capable of binding to the first target entity. In some embodiments, the kit can further comprise a second detection agent capable of binding to the second target entity.

The methods, compositions and kits described herein can be applicable for use with any sample. For example, a sample can comprise, without limitations, a biological sample (e.g., bodily fluids such as blood, cells, and tissue samples), an environmental sample, a cell culture sample, a blood culture, water, pharmaceutical preparations, foods, beverages, and any combinations thereof. In some embodiments, the sample is a fluid sample, e.g., blood or serum.

In some embodiments, the sample can comprise or be attached to a solid substrate as described herein. For example, in one embodiment, a sample can comprise a biological sample (e.g., a tissue sample) on a microscopic slide. In another embodiment, a sample can comprise protein or peptide on a membrane.

BRIEF DESCRIPTION OF THE DRAWINGS

FIG. 1 shows that the addition of ~10 mM glucose does not adversely affect mannan binding in buffer, whereas ~20 mM glucose effectively reduces the mannan binding by ~50% and ~40 mM glucose almost abolishes the mannan binding in buffer.

FIG. 2 shows that higher concentrations of glucose are required to effectively compete for binding of LPS to FcMBL. Unlike mannan detection (shown in FIG. 1), the addition of ~40 mM glucose or ~80 mM glucose does not significantly affect the detection of LPS in serum. When glucose was added at a concentration of about 160 mM, the LPS detection was reduced to 10% as compared to the LPS level determined in the absence of glucose.

FIG. 3A shows that the addition of glucose reduces the background noise contributed by interfering agents present in donor blood, thereby increasing the specificity of FcMBL binding to LPS, as evidenced by decreasing $OD_{450}$ signal as the concentration of LPS spiked in donor blood decreases. Further, FIG. 3B shows that the addition of glucose significantly decreases the binding of haemocytes (e.g., erythrocytes) to FcMBL in donor blood.

DETAILED DESCRIPTION OF THE INVENTION

Figure 1:
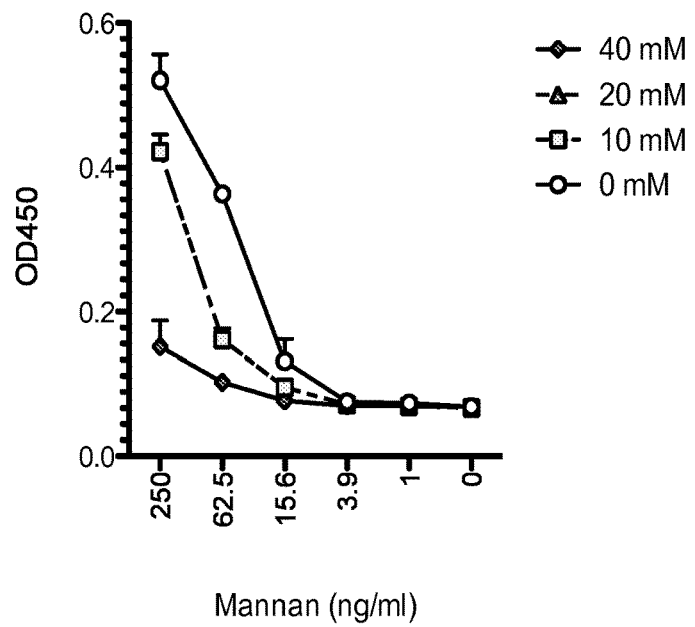
FIG. 1 is a line graph showing effects of adding various concentrations of a blocking agent (e.g., glucose) on binding of a target entity (e.g., mannan) to a target-binding agent (e.g., FcMBL beads) in a buffer.

Embodiments of various aspects described herein relate to methods, compositions and kits for detecting or capturing at least one target entity. The inventors have discovered inter alia that a target-binding agent pre-bound with an appropriate concentration of an intermediate-affinity ligand, prior to contacting a sample with the target-binding agent, can reduce non-target binding during capture of a target entity in the sample (e.g., blood). A traditional blocking agent (e.g., bovine serum albumin, which has no binding specificity) has been commonly used to mask unoccupied binding sites on an interfering agent (non-target material). However, the blocking agent described herein is unique, as the blocking agent is selected to bind specifically to a target-binding agent, not any other material such as interfering agents, and also be capable of being displaced by a target entity, if present in a sample. In particular, the inventors have discovered that, in one embodiment, pre-treating a microbe-binding agent comprising a mannan-binding domain (e.g., FcMBL) with an intermediate-affinity blocking agent (e.g., glucose) can not only improve binding specificity and/or sensitivity of the microbe-binding agent for microbes and/or fragments thereof (target entity), but can also reduce false positives resulting from non-target binding (e.g., haemocyte binding). In these embodiments, glucose was selected as one of the blocking agents for use in the FcMBL system to detect and/or capture microbes or fragments thereof, partly because glucose can prevent non-target or interfering agents such as haemocytes from binding to FcMBL, while permitting a target entity such as microbes and/or fragments thereof to displace glucose that is bound to FcMBL.

The concept of pre-treating a target-binding agent with a blocking agent, where the blocking agent is selected based on relative binding affinities of the blocking agent, a target entity and an interfering agent, respectively, for the target-binding agent, can be extended to any detection/capture processes, assays, systems and/or platforms in which binding interaction between the target entity and the target-binding agent is involved in a matrix comprising at least one interfering agent. The blocking agent used in these detection/capture processes, assays, systems and/or platforms can be selected to have an effective binding affinity for the target binding agent that is between an effective binding affinity of a target entity for the target-binding agent and the effective binding affinity of an interfering agent for the target-binding agent, so that the target entity, but not the interfering agent, can displace the blocking agent that is bound to the target-binding agent, and thus be captured on the target-binding agent.

Methods of Detecting or Capturing at Least One Target Entity

In one aspect, provided herein relates to methods of detecting or capturing at least one target entity, including, e.g., at least two target entities, at least three target entities, or more. The method comprises contacting a sample with a composition comprising a target-binding agent and a blocking agent, wherein the blocking agent is selected for reducing the binding of at least one interfering agent present in the sample to the target-binding agent, while permitting a first target entity, if present in the sample, to (a) displace the blocking agent bound to the target-binding agent, or to (b) bind to the target-binding agent without the blocking agent bound thereto.

In some embodiments, the blocking agent is bound to the target-binding agent, prior to contacting the sample with the composition. As used herein, the term "binding" or "bound" generally refers to a reversible binding of one agent or molecule to another agent or molecule via, e.g., van der Waals force, hydrophobic force, hydrogen bonding, and/or electrostatic force. The binding interaction between an agent or molecule and another agent or molecule can be described by a dissociation constant ($K_d$) or association constant (K), which is further described below. For example, in the presence of a higher affinity binder (e.g., a target entity), the blocking agent can be displaced by the higher affinity binder (e.g., a target entity).

In some embodiments, the blocking agent and the target-binding agent can be concurrently added to a sample.

The term "displace" is used in reference to a target entity being capable of causing a blocking agent that is bound to the target-binding agent to be released from the target-binding agent in order for the target entity to bind with the target-binding agent. The displacement of the blocking agent by the target-binding agent will generally occur when the target entity has a higher effective binding affinity for the target-binding agent than the blocking agent for the target-binding agent, e.g., by at least about 10%, at least about 20%, at least about 30%, at least about 40%, at least about 50%, at least about 60%, at least about 70%, at least about 80%, at least about 90%, or more. In some embodiments, the displacement of the blocking agent by the target-binding agent will occur when the target entity has a higher effective binding affinity for the target-binding agent than the blocking agent for the target-binding agent, e.g., by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, or more.

The term "contacting" or "contact" as used herein in connection with contacting a sample refers to subjecting a sample to a composition comprising a target-binding agent and a blocking agent by any means, which can vary with different formats of the compositions. For example, in some embodiments, the composition can be added into a fluid sample. In some embodiments, the sample can be flown through the composition (e.g., as a membrane) described herein to make the contact. In some embodiments, the sample can flow through a channel, e.g., a microfluidic channel or a tubing, having the inner wall coated with the composition described herein to make the contact. In some embodiments, the sample can be deposited or placed on the composition (e.g., a composition comprising a solid substrate affixed with the target-binding agent and a block agent bound thereto).

In some embodiments of this aspect and other aspects described herein, the effective binding affinity of the blocking agent for the target-binding agent can be selected for increasing apparent specificity of the target-binding agent to the first target entity in the sample, as compared to the apparent specificity in the absence of the blocking agent. For example, the apparent specificity of the target-binding agent to the first target entity can be increased by reducing the binding of said at least one interfering agent to the target-binding agent, which can in turn increase the availability of binding sites on the target-binding agent for the target entity. While the binding of said at least one interfering agent to the target-binding agent is typically reduced by blocking the unoccupied binding sites on the interfering agent, the inventors instead pre-block the binding sites on the target-binding agent with a blocking agent such that the interfering agent cannot bind to the target-binding agent, but the target entity is able to displace the blocking agent due to the target entity's higher affinity for the target-binding agent than that of the blocking agent. Selection of an appropriate blocking agent for use in the methods described herein is described in the section "Blocking agents" later below.

In some embodiments, the method can further comprise exposing the target-binding agent to the blocking agent at a pre-determined concentration to form the composition comprising the target-binding agent and the blocking agent bound thereto, prior to the contacting of the sample with the composition.

The blocking agent can be generally present in a sample at any concentration provided that its presence in the sample does not adversely affect the binding of the first target entity to the target-binding agent. In some embodiments, the blocking agent can be present in a pre-determined concentration that does not reduce the binding of the first target entity to the target-binding agent, e.g., by more than 60%, more than 50%, more than 40%, more than 30%, more than 20%, more than 10%, more than 5%, more than 1%, or less, as compared to the binding in the absence of the blocking agent.

Figure 3A:
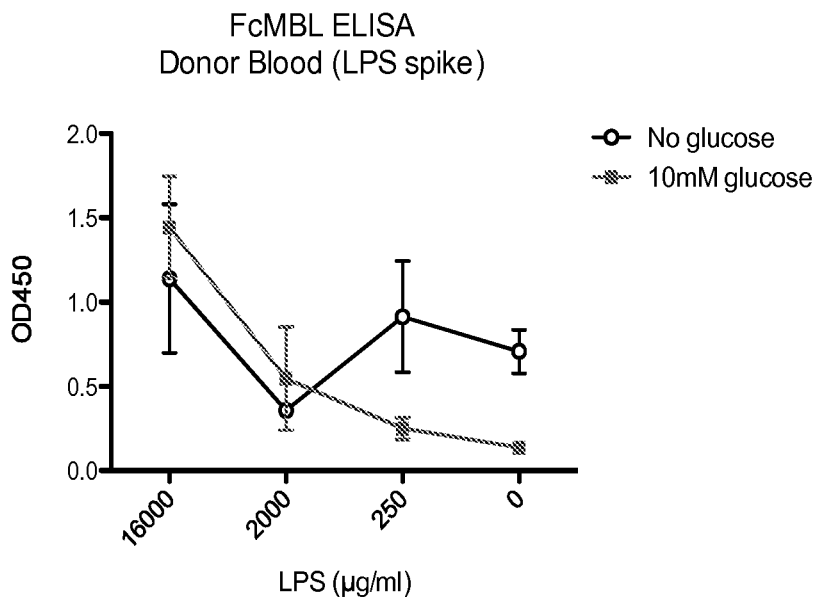
FIGS. 3A-3B are data graphs showing effects of adding a blocking agent (e.g., ~10 mM glucose) on binding of a target entity (e.g., LPS) or an interfering agent (e.g., haemocytes) to a target-binding agent (e.g., FcMBL beads) in donor blood.
Figure 3B:
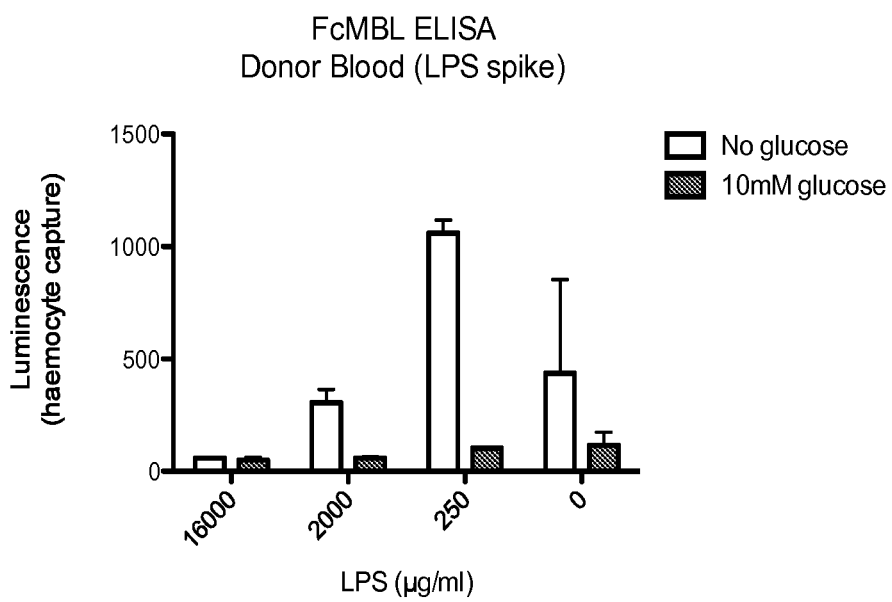

FIG. 3A shows that the addition of a blocking agent (e.g., glucose) reduces the background noise contributed by interfering agents present in donor blood, thereby increasing the specificity of a target-binding agent (e.g., FcMBL) binding to a target entity (e.g., LPS), as evidenced by decreasing $OD_{450}$ signal as the concentration of LPS spiked in donor blood decreases. Further, FIG. 3B shows that the addition of a blocking agent (e.g., glucose) can significantly decrease the binding of interfering agents such as haemocytes (e.g., erythrocytes) to a target-binding agent (e.g., FcMBL) in donor blood. Accordingly, in some embodiments, the blocking agent can be provided in the pre-determined concentration, which is sufficient to reduce the binding of said at least one interfering agent to the target-binding agent, e.g., by at least about 10%, at least about 20%, at least about 30%, at least about 40%, at least about 50%, at least about 60%, at least about 70%, at least about 80%, at least about 90%, at least about 95%, at least about 98%, at least about 99%, or more, as compared to the binding in the absence of the blocking agent. In one embodiment, the blocking agent can be present in a concentration sufficient to partially or completely inhibit the binding of said at least one interfering agent to the target-binding agent. Without wishing to be bound by theory, by reducing or inhibiting the binding of said at least one interfering agent to the target-binding agent, the binding sensitivity and/or specificity of the target binding agent for the corresponding target entity can be increased, e.g., due to a lower background noise contributed by the interfering agent. Accordingly, in some embodiments, the blocking agent can be provided in the pre-determined concentration, which is sufficient to decrease the lower limit of detection of the target-binding agent binding to the first target entity in the sample, e.g., by at least about 10%, at least about 20%, at least about 30%, at least about 40%, at least about 50%, at least about 60%, at least about 70%, at least about 80%, at least about 90%, or more, when compared to the lower limit of detection in the absence of the blocking agent.

Figure 2:
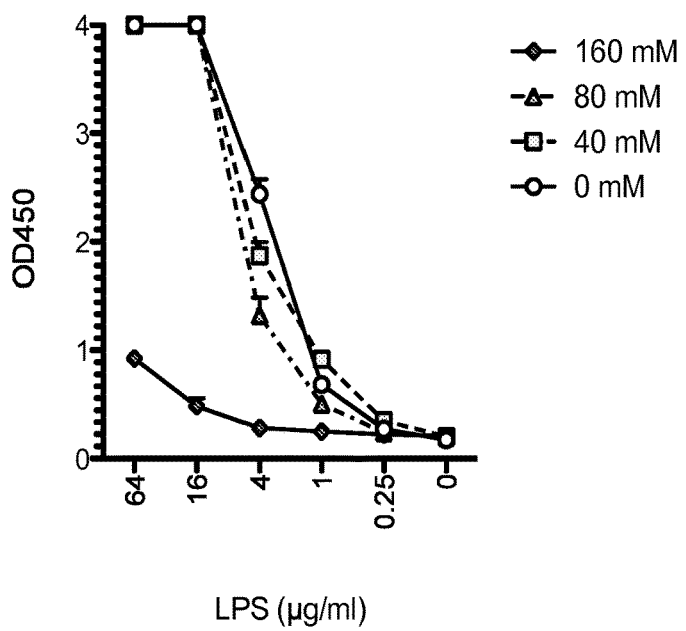
FIG. 2 is a line graph showing effects of adding various concentrations of a blocking agent (e.g., glucose) on binding of a target entity (e.g., lipopolysaccharide (LPS)) to a target-binding agent (e.g., FcMBL beads) in a buffer.

The pre-determined concentration of the blocking agent can vary with the effective binding affinity of the target entity for the target-binding agent. For example, a target-binding agent (e.g., FcMBL) has a relatively high affinity for bacterial lipopolysaccharide (LPS), as compared to mannan binding. Thus, as shown in FIG. 2, higher concentrations of a blocking agent (e.g., glucose) are required to effectively compete with LPS for binding to FcMBL. Unlike mannan detection as shown in FIG. 1, the addition of ~40 mM blocking agent (e.g., glucose) or ~80 mM blocking agent (e.g., glucose) does not significantly affect the detection of a target entity (LPS) in serum, until high concentrations of the blocking agent were used. Accordingly, a higher concentration of the blocking agent can be used without adversely affect the binding of the target-binding agent to the target entity with a higher effective binding affinity. In some embodiments where the glucose is the blocking agent, the pre-determined concentration of glucose can range from about 5 mM to about 200 mM. In some embodiments, the pre-determined concentration of glucose can be less than 20 mM. In some embodiments, the pre-determined concentration of glucose can be more than 20 mM. One of skill in the art can determine the optimum concentration of the blocking agent to be used, e.g., by determining amounts of target entity bound to the target-binding agent in the presence of blocking agent at various concentrations, e.g., as described in Example 1 and shown in FIGS. 1-2.

In some embodiments, the method can further comprise separating the target-binding agent from the sample after the contacting. By way of example only, the target-binding agent in the form of magnetic particles (e.g., target-binding magnetic particles) can be separated from the sample after the contacting in the presence of a magnetic field gradient. In some embodiments where the target-binding agent is a target-binding dipstick, target-binding agent can be separated from the sample by simply removing the target-binding dipstick from the sample. In some embodiments where the target-binding agent comprises particles, the target-binding agent can be separated from the sample by centrifugation and/or filtration. Methods for separating the target-binding agent from the sample are dependent on the format of the target-binding agents and are generally known in the art. In some embodiments where the method described herein is used to detect and/or capture a microbe, the target-binding agent (e.g., a microbe-binding agent) can be separated from the sample following one or a combination of the methods as described in step 1210 (microbe separation) of the process 1200 described later below.

In some embodiments, the method can further comprise performing a competitive wash to release, if any, said at least one interfering agent that remains bound to the target-binding agent after the contacting and/or separation. For example, the target-binding agent after the contacting and/or separation can be further washed with a buffer comprising a blocking agent described herein so as to remove any residual interfering agents still bound to the target-binding agent. In some embodiments, the competitive wash can be used to remove any residual interfering agents not competed away by the target-binding agent, e.g., due to low abundance of the target binding agent. The blocking agent used in the wash buffer can be the same as, or different from, the one used during the capture of the target entity.

In some embodiments, the method can further comprise detecting a target entity, after the sample is contacted with a composition comprising a target-binding agent and a blocking agent. The target entity can remain bound on the target-binding agent during detection and/or analysis, or be detached from the target-binding agent prior to detection and/or analysis. Methods for detecting the target entity are known in the art, e.g., by spectroscopy, electrochemical detection, polynucleotide detection, fluorescence anisotropy, fluorescence resonance energy transfer, electron transfer, enzyme assay, magnetism, electrical conductivity, isoelectric focusing, chromatography, immunoprecipitation, immunoseparation, aptamer binding, filtration, electrophoresis, use of a CCD camera, immunoassay, ELISA, Gram staining, immunostaining, microscopy, immunofluorescence, western blot, polymerase chain reaction (PCR), RT-PCR, fluorescence in situ hybridization, sequencing, mass spectroscopy, or substantially any combination thereof.

In some embodiments, the detecting of a target entity can comprise contacting the target-binding agent with a detection agent, wherein the target entity, if present, remains bound on the target-binding agent. In some embodiments, a sub-population of the target-binding agent comprises a target entity, if present in a sample, bound thereto; while a sub-population of the target-binding agent can still comprise the blocking agent bound thereto. In some embodiments, a sub-population of the target-binding agent can comprise both the target entity and the blocking agent bound thereto. In some embodiments, the blocking agent that is already bound to the target-binding agent cannot bind to a detection agent and thus cannot interfere with detection of the bound target entity. In other embodiments, the blocking agent that is already bound to the target-binding agent can still bind to a detection agent. In these embodiments, the blocking agent can be treated, prior to addition of a detection gent, to mask its spare binding sites such that the blocking agent becomes unable to bind to the detection agent.

In some embodiments, the detecting of a target entity can comprise contacting a target entity, if present, with a detection agent, wherein the target entity has been detached from the target-binding agent.

The detection agent used to detect a target entity can be any molecule or compound that can bind to a target entity and be detected by any methods known in the art. Examples of a detection agent include, but are not limited to, proteins, peptides, antibodies or fragments thereof, aptamers, nucleic acid molecules, polynucleotides, oligonucleotides, carbohydrates, and any combinations thereof. In some embodiments, the detection agent can comprise a detectable label. A detectable label can include, but not limited to, an optical label, a radioactive label, an oligonucleotide label, an enzyme label (e.g., but not limited to, a horseradish peroxidase (HRP) or an alkaline phosphatase (AP)), a metabolic label, or any combinations thereof.

In some embodiments where the target entity comprises a microbe or a fragment thereof, the detection agent can comprise a carbohydrate recognition domain derived from a carbohydrate-binding molecule. Examples of a carbohydrate-binding molecule include, but are not limited to, lectin, collectin, ficolin, mannose-binding lectin (MBL), maltose-binding protein, arabinose-binding protein, glucose-binding protein, *Galanthus nivalis* agglutinin, peanut lectin, lentil lectin, DC-SIGN, C-reactive protein, and any combinations thereof. In some embodiments, the detection agent can comprise a carbohydrate recognition domain and a detectable label. In some embodiments, the detection agent is a fusion peptide comprising a carbohydrate recognition domain of a lectin, wherein the fusion peptide is conjugated to a detectable label. For example, the fusion peptide can be a FcMBL, which is a fusion peptide comprising mannan-binding lectin and a Fc portion of an immunoglobulin, and is described in the U.S. application Ser. No. 13/574,191 entitled "Engineered Opsonin for Pathogen Detection and Treatment" and U.S. application Ser. No. 14/233,553 entitled "Engineered Microbe-Targeting Molecules and Uses Thereof," both of which the patent applications are incorporated herein by reference. In some embodiments, a detection agent can be a FcMBL conjugated to an enzyme label (e.g., but not limited to, a horseradish peroxidase or an alkaline phosphatase). Detection agents such as FcMBL-HRP or FcMBL-AP described in U.S. application Ser. No. 14/233,553 entitled "Engineered Microbe-Targeting Molecules and Uses Thereof," incorporated by reference, can be also used herein.

In some embodiments, the method can further comprise detecting the displaced blocking agent. Without wishing to be bound by theory, the amount of the displaced blocking agent can be proportional to the amount of the target entity displacing the blocking agent. Accordingly, in some embodiments, rather than directly determining the amount of the target entity bound on the target-binding agent, the amount of the target entity can be also reflected by a measurement of the amount of the displaced blocking agent. To facilitate detection of the displaced blocking agent, in some embodiments, the blocking agent can comprise a detectable label, e.g., a fluorescent label or any detectable labels described herein.

Blocking Agents

While it may not be necessary to have a target-binding agent pre-bound with a blocking agent, in some embodiments, it can be beneficial to add the blocking agent to the target-binding agent prior to contacting a sample with the target-binding agent, e.g., when there is a much higher abundance of interfering agents than the target entity present in a sample.

In some embodiments, the blocking agent can be selected based on its effective binding affinity relative to effective binding affinities of the first target entity and said at least one interfering agent, respectively, for the target-binding agent. In some embodiments, the blocking agent can be selected to have an effective binding affinity for the target-binding agent that is lower than an effective binding affinity of the first target entity for the target-binding agent; and the blocking agent is further selected to have the effective binding affinity for the target-binding agent that is higher than an effective binding affinity of at least one interfering agent present in the sample for the target-binding agent.

In order to permit the first target entity to displace the blocking agent bound to the target-binding agent, the effective binding affinity of the blocking agent for the target-binding agent is desired to be lower than the effective binding affinity of the first target entity for the target-binding agent. In some embodiments of this aspect and other aspects described herein, the effective binding affinity of the blocking agent for the target-binding agent can be lower than the effective binding affinity of the first target entity for the target-binding agent by at least about 10% or more, including, e.g., at least about 20%, at least about 30%, at least about 40%, at least about 50%, at least about 60%, at least about 70%, at least about 80%, at least about 90% or more.

In order to reduce or prevent at least one interfering agent from binding to the target-binding agent, the effective binding affinity of the blocking agent for the target-binding agent is desired to be higher than the effective binding affinity of said at least one interfering agent present in the sample for the target-binding agent. In some embodiments of this aspect and other aspects described herein, the effective binding affinity of the blocking agent for the target-binding agent can be higher than the effective binding affinity of said at least one interfering agent present in the sample for the target-binding agent by at least about 10% or more, including, e.g., at least about 20%, at least about 30%, at least about 40%, at least about 50%, at least about 60%, at least about 70%, at least about 80%, at least about 90% or more. In some embodiments, the effective binding affinity of the blocking agent for the target-binding agent can be higher than the effective binding affinity of said at least one interfering agent present in the sample for the target-binding agent by at least about 1-fold or more, including, e.g., at least about 2-fold, at least about 3-fold, at least about 4-fold, at least about 5-fold, at least about 6-fold, at least about 7-fold, at least about 8-fold, at least about 9-fold, at least about 10-fold or more.

As used herein, the term "effective binding affinity" generally refers to an overall binding property of a first agent (e.g., a blocking agent, an interfering agent, and/or a target entity) interacting with a second agent (e.g., a target-binding agent) under a specific condition, and the overall binding property is typically dependent on intrinsic characteristics of the first agent and the second agent including, but not limited to, surface composition of the first agent and/or the second agent (e.g., but not limited to, density of target-binding molecules present on the surface of the target-binding agent such as FcMBL density on the beads), single-bond affinity, avidity, as well as the surrounding/ambient condition for the binding interaction, e.g., but not limited to, concentration of the first agent and/or the second agent, and/or the presence of a third agent (e.g., a blocking agent, an interfering agent and/or a target entity) during the binding interaction between the first and the second agents. Different measures of an effective binding affinity of an agent are known in the art. In some embodiments, the effective binding affinity of a first agent for a second agent can be indicated by a dissociation constant ($K_d$) for binding of the first agent to the second agent. The dissociation constant ($K_d$) is an equilibrium constant that generally measures the propensity of a bound complex to separate (dissociate) reversibly into separate agents. In these embodiments, a higher dissociation constant indicates a lower effective binding affinity. Alternatively, the effective binding affinity of a first agent for a second agent can be indicated by an association constant (K) for binding of the first agent to the second agent. The association constant (K) is the inverse of the dissociation constant ($K_d$), i.e., a higher association constant indicates a higher effective binding affinity.

As used herein, the term "single-bond affinity" refers to the strength of a single bond interaction, including but not limited to hydrogen bonds, electrostatic bonds, van der Waals forces, hydrophobic forces, or any combinations thereof.

As used herein, the term "avidity" refers to the combined strength of multiple bond interactions. Avidity is distinct from affinity or single-bond affinity, which is the strength of a single bond interaction. In general, avidity is the combined synergistic strength of bond affinities rather than the sum of bonds. Accordingly, avidity is generally used to describe one agent having multiple interactions with another agent. For example, where the blocking agent may have similar single-bond affinity as that of the target entity to the target-binding agent, the target entity can have higher avidity than that of the blocking agent if the target entity can form more bonds than the blocking agent with the target-binding agent. The higher avidity of the target entity would yield a higher effective binding affinity than that of the blocking agent.

Accordingly, in some embodiments, the effective binding affinity of the blocking agent can be dependent on a number of properties including, but not limited to, surface composition of the blocking agent, avidity, single-bond affinity or affinity, surface composition of the target-binding agent (e.g., but not limited to, density of target-binding molecules present on the surface of the target-binding agent), concentration of the blocking agent, concentration of the first target entity in the sample, concentration of said at least one interfering agent, or any combinations thereof. By way of example only, in some embodiments where both the target entity and the blocking agent comprise a glucose molecule, the target entity, e.g., a microbe or a fragment thereof comprising on its surface a glucose molecule in combination with other sugar molecules, or more than one glucose molecules in a specific pattern, can have a higher effective binding affinity for the target-binding agent (e.g., FcMBL) that that of a glucose monomer as a blocking agent, partly due to the higher avidity observed in the microbes or fragments thereof.

In some embodiments of this aspect and other aspects described herein, the effective binding affinity of the blocking agent for the target-binding agent, as indicated by a dissociation constant for the binding of the blocking agent to the target-binding agent, can range from about 1 μM to about 100 mM, or about 10 μM to about 75 mM, or about 5 mM to about 50 mM. In one embodiment, the effective binding affinity of the blocking agent for the target-binding agent, as indicated by a dissociation constant for the binding of the blocking agent to the target-binding agent, can range from about 5 mM to about 50 mM. In some embodiments, the effective binding affinity of the blocking agent for the target-binding agent, as indicated by a dissociation constant for the binding of the blocking agent to the target-binding agent, can be in a nanomolar range. For example, in some embodiments, the effective binding affinity of the blocking agent for the target-binding agent, as indicated by a dissociation constant for the binding of the blocking agent to the target-binding agent, can range from about 1 nM to 10 μM, about 1 nM to about 1 μM, or about 10 nM to about 500 nM.

In some embodiments, the effective binding affinity ratio of a blocking agent to a target entity (for a target-binding agent), as indicated by dissociation constants, can range from about 2:1 to about 1000:1, from about 2:1 to about 500:1, from about 2:1 to about 100:1, or from about 2:1 to about 50:1, from about 2:1 to about 25:1, from about 2:1 to about 10:1, from about 2:1 to about 5:1.

The blocking agent can be any molecule, compound, or agent that can bind to a target-binding agent with an effective binding affinity between that of the target entity and the interfering agent, respectively, for the target-binding agent. Depending on the binding properties of the target-binding agents, target entity, and/or interfering agents, the blocking agent can include, but not limited to, cells or fragments thereof, peptides, polypeptides, proteins, peptidomimetics, antibodies, antibody fragments (e.g., antigen binding fragments of antibodies), carbohydrate-binding protein, e.g., lectins, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, endotoxins (e.g., bacterial lipopolysaccharide), and any combinations thereof. In some embodiments, the cells include, but are not limited to, prokaryotes (e.g., microbes such as bacteria) and eukaryotes (e.g., animal cells, plant cells, yeasts, and fungi), blood cells, and any fragments thereof. In some embodiments where the target-binding agent is configured to recognize a carbohydrate pattern, e.g., for detection and/or capture of a microbe or a fragment thereof, the blocking agent can be a carbohydrate or a saccharide.

In some embodiments, the blocking agent can be a monomer. In general, a monomer (with a single binding site) has no free binding site after binding to the target-binding agent. Accordingly, for monomeric blocking agents that have not been displaced by the target entity and still remain bound on the target-binding agent, the bound monomeric blocking agents will unlikely be detected by an assay using a "sandwich" method, e.g., ELISA, due to the absence of binding sites for binding with a detection agent. Thus, the target entity can be detected, e.g., using a "sandwich" method, e.g., ELISA, without getting significant background signals from the monomeric blocking agents.

Examples of a saccharide-based monomeric blocking agent can be a monosaccharide or modification thereof, including, e.g., but not limited to, diose, triose, tetrose, pentose, hexose, heptose, linear chain monosaccharides, open chain monosaccharides, cyclic isomers (e.g., furanose form and pyranose of monosaccharides such as hexose), pyranose, fructose, galactose, xylose, ribose, amino sugars (e.g., but not limited to, galactosamine, glucosamine, sialic acid, N-acetylglucosamine, N-acetyl-muramic acid, sulfosugars (e.g., but not limited to sulfoquinovose). In some embodiments, one or more of these saccharide-based monomeric blocking agents can be used in an assay to detect and/or capture microbes and/or fragments thereof, e.g., added prior to step 1208 (microbe capture) of process 1200 as described below. In one embodiment, the saccharide-based monomeric blocking agent can comprise glucose.

In alternative embodiments, the blocking agent can be a multimer, i.e., a blocking agent that has at least one free binding site after binding to the target-binding agent. In these embodiments, bound multimer blocking agents remained on the target-binding agents can have additional binding sites. In some embodiments, addition of another monomeric blocking agent to block these additional binding sites prior to detection of the captured target entities, e.g., using a "sandwich" method such as ELISA or any other detection methods known in the art can be performed. To identify $K_d$ for multimers, one can, for example, evaluate the $K_d$ of the corresponding monomers experimentally.

Examples of a saccharide-based multimeric blocking agent can be a disaccharide, an oligosaccharide, a polysaccharide, modifications thereof, or any combinations thereof, including, e.g., but not limited to, lactose, sucrose, maltose, lactulose, trehalose, cellobiose, kojibiose, nigerose, isomaltose, β,β-trehalose, α,β-trehalose, sophorose, laminaribiose, gentiobiose, turanose, maltulose, palatinose, gentiobiulose, mannobiose, melibiose, melibiulose, rutinose, rutinulose, xylobiose, fructo-oligosaccharides, galactooligosaccharides, mannan oligosaccharides, cellulose, chitin, callose, laminarin, chrysilaminarin, xylan, arabinoxylan, mannan, fucoidan, galactomannan, or any combinations thereof. In some embodiments, one or more of these saccharide-based multimeric blocking agents can be used in an assay to detect and/or capture microbes and/or fragments thereof, e.g., added prior to step 1208 (microbe capture) of process 1200 as described below.

In some embodiments, a saccharide-based blocking agent can be glucose, maltose, N-acetyl-muramic acid, or any combinations thereof. In one embodiment, a saccharide-based blocking agent can comprise glucose. In some embodiments, one or more of these saccharide-based blocking agents can be used in an assay to detect and/or capture microbes and/or fragments thereof, e.g., added prior to step 1208 (microbe capture) of process 1200 as described below.

Interfering Agents

An interfering agent is an agent present in a sample to be assayed, which undesirably binds to a target-binding agent and reduces the effective binding affinity of the target-binding agent to the corresponding target entity, e.g., by at least about 10% or more, including, e.g., at least about 20%, at least about 30%, at least about 40%, at least about 50%, at least about 60%, at least about 70%, at least about 80%, at least about 90% or more. Examples of the interfering agents include, but are not limited to, cells or fragments thereof, peptides, polypeptides, proteins, peptidomimetics, antibodies, antibody fragments (e.g., antigen binding fragments of antibodies), carbohydrate-binding protein, e.g., lectins, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, endotoxins (e.g., bacterial lipopolysaccharide), and any combinations thereof. In some embodiments, the cells include, but are not limited to, prokaryotes (e.g., microbes such as bacteria) and eukaryotes (e.g., animal cells, plant cells, yeasts, and fungi), blood cells, and any fragments thereof.

In some embodiments where the sample comprises a biological fluid, e.g., blood, at least one interfering agent can comprise a blood cell and/or a fragment thereof, e.g., a red blood cell (or an erythryocyte) and/or a fragment thereof.

In some embodiments where the sample comprises a second target entity not intended to be captured or detected by the first target-binding agent, but by a second target-binding agent, the second target entity can be considered as an interfering agent with respect to the binding interaction between the first target-binding agent and the first target entity.

In some embodiments, said at least one interfering agent can be a non-specific binding molecule. As used herein, the term "non-specific binding molecule" refers to a molecule capable of binding to the target-binding agent, which is not correlated with the specificity of the target-binding agent. In some embodiments, the non-specific binding molecule can bind to the target-binding agent, e.g., via adsorption.

In some embodiments, the binding of said at least one interfering agent with the target-binding agent can be specific, but the effective binding affinity of the interfering agent for the target-binding agent is lower than that of the target entity and/or the blocking agent for the target-binding agent.

In some embodiments, the effective binding affinity of said at least one interfering agent can be dependent on a number of properties including, but not limited to surface composition of the interfering agent, avidity, single-bond affinity or affinity, surface composition of the target-binding agent (e.g., but not limited to, density of target-binding molecules present on the surface of the target-binding agent such as FcMBL density on the beads), concentration of the blocking agent, concentration of the first target entity in the sample, concentration of said at least one interfering agent, or any combinations thereof.

As described herein, the effective binding affinity of said at least one interfering agent for the target-binding agent is lower than the effective binding affinity of the blocking agent for the target-binding agent. Accordingly, in some embodiments of this aspect and other aspects described herein, the effective binding affinity of said at least one interfering agent for the target-binding agent, as indicated by a dissociation constant for the binding of the interfering agent to the target-binding agent, can be more than 5 µM, more than 10 µM, more than 0.1 mM, more than 0.5 mM, more than 1 mM, more than 5 mM, more than 10 mM, more than 25 mM, more than 50 mM, more than 75 mM, more than 100 mM or more, provided that the dissociation constant for the binding of the interfering agent to the target-binding agent is larger than that for the binding of the blocking agent to the target-binding agent. In some embodiments, the effective binding affinity of said at least one interfering agent for the target-binding agent, as indicated by a dissociation constant for the binding of the interfering agent to the target-binding agent, can be more than 10 mM. In some embodiments, the effective binding affinity of said at least one interfering agent for the target-binding agent, as indicated by a dissociation constant for the binding of the interfering agent to the target-binding agent, can be more than 50 mM. In some embodiments, the effective binding affinity of said at least one interfering agent for the target-binding agent, as indicated by a dissociation constant for the binding of said at least one interfering agent to the target-binding agent, can be in a lower range, e.g., more than 500 nM, or more than 1 µM or higher.

Target Entity or Target Species

The methods, compositions and kits described herein can be used to capture or isolate one or more target entities from a test sample. As used interchangeably herein, the terms "target entity" and "target species" refer to any molecule, cell or particulate that is to be separated or isolated from a fluid sample. Representative examples of target cellular entities include, but are not limited to, mammalian cells, viruses, bacteria, fungi, yeast, protozoan, microbes, parasites, endotoxins (e.g., bacterial lipopolysaccharide), and any combinations thereof. Representative additional examples of target entities include, but are not limited to, peptides, polypeptides, proteins, peptidomimetics, antibodies, antibody fragments (e.g., antigen binding fragments of antibodies), carbohydrate-binding protein, e.g., lectins, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, toxins, and any combinations thereof. The target species can also include contaminants found in non-biological fluids, such as pathogens or lead in water or in petroleum products. Parasites can include organisms within the phyla Protozoa, Platyhelminthes, Aschelminthes, Acanthocephala, and Arthropoda.

In some embodiments, the effective binding affinity of the target entity can be dependent on a number of properties including, but not limited to, surface composition of the target entity, avidity, single-bond affinity or affinity, surface composition of the target-binding agent (e.g., but not limited to, density of target-binding molecules present on the surface of the target-binding agent such as FcMBL density on the beads), concentration of the blocking agent, concentration of the first target entity in the sample, concentration of said at least one interfering agent, or any combinations thereof.

As described earlier, the effective binding affinity of the blocking agent for the target-binding agent is lower than the effective binding affinity of the target entity for the target-binding agent. Accordingly, in some embodiments of this aspect and other aspects described herein, the effective binding affinity of the target entity for the target-binding agent, as indicated by a dissociation constant for the binding of the target entity to the target-binding agent, can be less than 100 mM, less than 75 mM, less than 50 mM, less than 25 mM, less than 10 mM, less than 5 mM, less than 1 mM, less than 0.5 mM, less than 0.1 mM, less than 10 µM, less than 1 µM, or less, provided that the dissociation constant for the binding of the blocking agent to the target-binding agent is smaller than higher than that for the binding of the target entity to the target-binding agent. In some embodiments, the effective binding affinity of the target entity for the target-binding agent, as indicated by a dissociation constant for the binding of the target entity to the target-binding agent, can be less than 25 mM. In some embodiments, the effective binding affinity of the target entity for the target-binding agent, as indicated by a dissociation constant for the binding of the target entity to the target-binding agent, can be in a nanomolar range. For example, in some embodiments, the effective binding affinity of the target entity for the target-binding agent, as indicated by a dissociation constant for the binding of the target entity to the target-binding agent, can be less than 1 µM, less than 500 nM, less than 100 nM, less than 50 nM, less than 25 nM, less than 10 nM, less than 5 nM, less than 1 nM, less than 0.5 nM, or less.

In some embodiments, the target species can include a biological cell selected from the group consisting of living or dead cells (prokaryotic and eukaryotic, including mammalian), viruses, bacteria, fungi, yeast, protozoan, microbes, and parasites. The biological cell can be a normal cell or a diseased cell, e.g., a cancer cell. Mammalian cells include, without limitation; primate, human and a cell from any animal of interest, including without limitation; mouse, hamster, rabbit, dog, cat, domestic animals, such as equine, bovine, murine, ovine, canine, and feline. In some embodiments, the cells can be derived from a human subject. In other embodiments, the cells are derived from a domesticated animal, e.g., a dog or a cat. Exemplary mammalian cells include, but are not limited to, stem cells, cancer cells, progenitor cells, immune cells, blood cells, fetal cells, and any combinations thereof. The cells can be derived from a wide variety of tissue types without limitation such as, hematopoietic, neural, mesenchymal, cutaneous, mucosal, stromal, muscle, spleen, reticuloendothelial, epithelial, endothelial, hepatic, kidney, gastrointestinal, pulmonary, cardiovascular, T-cells, and fetus. Stem cells, embryonic stem (ES) cells, ES-derived cells, induced pluripotent stem cells, and stem cell progenitors are also included, including without limitation, hematopoietic, neural, stromal, muscle, cardiovascular, hepatic, pulmonary, and gastrointestinal stem cells. Yeast cells may also be used as cells in some embodiments described herein. In some embodiments, the cells can be ex vivo or cultured cells, e.g. in vitro. For example, for ex vivo cells, cells can be obtained from a subject, where the subject is healthy and/or affected with a disease. While cells can be obtained from a fluid sample, e.g., a blood sample, cells can also be obtained, as a non-limiting example, by biopsy or other surgical means know to those skilled in the art.

In some embodiments, the target species refers to a rare cell or a cellular component thereof. In some embodiments, the target species can refer to a rare cell or a cellular component thereof derived from a mammalian subject, including, without limitation, primate, human or any animal of interest such as mouse, hamster, rabbit, dog, cat, domestic animals, such as equine, bovine, murine, ovine, canine, and feline. In some embodiments, the rare cells can be derived from a human subject. In other embodiments, the rare cells can be derived from a domesticated animal or a pet such as a cat or a dog. As used herein, the term "rare cells" is defined, in some embodiments, as cells that are not normally present in a fluid sample, e.g., a biological fluid sample, but can be present as an indicator of an abnormal condition, such as infectious disease, chronic disease, injury, proliferative diseases, or pregnancy. In some embodiments, the term "rare cells" as used herein refers to cells that can be normally present in biological specimens, but are present with a frequency several orders of magnitude (e.g., at least about 100-fold, at least about 1000-fold, at least about 10000-fold) less than other cells typically present in a normal biological specimen. In some embodiments, rare cells are found infrequently in circulating blood, e.g., less than 100 cells (including less than 10 cells, less than 1 cell) per $10^8$ mononuclear cells in about 50 mL of peripheral blood. In some embodiments, a rare cell can be a normal cell or a diseased cell. Examples of rare cells include, but are not limited to, circulating tumor cells, progenitor cells, e.g., collected for bone marrow transplantation, blood vessel-forming progenitor cells, stem cells, circulating fetal cells, e.g., in maternal peripheral blood for prenatal diagnosis, virally-infected cells, cell subsets collected and manipulated for cell and gene therapy, and cell subpopulations purified for subsequent gene expression or proteomic analysis, other cells related to disease progression, and any combinations thereof.

As used herein, the term "a cellular component" in reference to circulating tumor cells, stem cells, fetal cells and/or microbes is intended to include any component of a cell that can be at least partially isolated from the cell, e.g., upon lysis of the cell. Cellular components can include, but are not limited to, organelles, such as nuclei, perinuclear compartments, nuclear membranes, mitochondria, chloroplasts, or cell membranes; polymers or molecular complexes, such as lipids, polysaccharides, proteins (membrane, trans-membrane, or cytosolic); nucleic acids, viral particles, or ribosomes; or other molecules, such as hormones, ions, and cofactors.

As used herein, the term "molecular toxin" refers to a compound produced by an organism which causes or initiates the development of a noxious, poisonous or deleterious effect in a host presented with the toxin. Such deleterious conditions may include fever, nausea, diarrhea, weight loss, neurologic disorders, renal disorders, hemorrhage, and the like. Toxins include, but are not limited to, bacterial toxins, such as cholera toxin, heat-liable and heat-stable toxins of *E. coli*, toxins A and B of *Clostridium difficile*, aerolysins, and hemolysins; toxins produced by protozoa, such as *Giardia*; toxins produced by fungi. Molecular toxins can also include exotoxins, i.e., toxins secreted by an organism as an extracellular product, and enterotoxins, i.e., toxins present in the gut of an organism.

Target-binding Agents

A target-binding agent is an agent configured to detect and/or capture at least one target entity described herein. The target-binding agent can be present in any form, including but not limited to a target-binding molecule, and/or a target-binding substrate (e.g., a target-binding molecule conjugated to a solid substrate or a solid supporting structure). In some embodiments, the target-binding agent can comprise a target-binding molecule selected from the group consisting of cells or fragments thereof, peptides, polypeptides, proteins, peptidomimetics, antibodies, antibody fragments (e.g., antigen binding fragments of antibodies), carbohydrate-binding protein, e.g., lectins, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, endotoxins (e.g., bacterial lipopolysaccharide), and any combinations thereof.

In some embodiments, a target-binding agent can comprise a microbe-binding agent as described in the section "Microbe-binding agents or molecules" below.

In some embodiments, the target-binding agent can be affixed to a solid substrate described herein to form a target-binding substrate. Non-limiting examples of a solid substrate include, but are not limited to, a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combinations thereof.

The solid substrate can be made of any material, including, but not limited to, metal, metal alloy, polymer, plastic, paper, glass, fabric, packaging material, biological material such as cells, tissues, hydrogels, proteins, peptides, nucleic acids, and any combinations thereof.

In some embodiments, the solid substrate can be fabricated from or coated with a biocompatible material. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include, for example, derivatives and copolymers of polyimides, poly(ethylene glycol), polyvinyl alcohol, polyethyleneimine, and polyvinylamine, polyacrylates, polyamides, polyesters, polycarbonates, and polystyrenes. In some embodiments, biocompatible materials can include metals, such as titanium and stainless steel, or any biocompatible metal used in medical implants. In some embodiments, biocompatible materials can include paper substrate, e.g., as a solid substrate for a diagnostic strip. In some embodiments, biocompatible materials can include peptides or nucleic acid molecules, e.g., a nucleic acid scaffold such as a 2-D DNA sheet or 3-D DNA scaffold.

Additional material that can be used to fabricate or coat a solid substrate include, without limitations, polydimethylsiloxane, polyimide, polyethylene terephthalate, polymethylmethacrylate, polyurethane, polyvinylchloride, polystyrene polysulfone, polycarbonate, polymethylpentene, polypropylene, polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly (ethylene glycol), styrene-acrylonitrile resin, poly(trimethylene terephthalate), polyvinyl butyral, polyvinylidenedifluoride, poly(vinyl pyrrolidone), and any combination thereof.

In some embodiments, at least a portion of a solid substrate surface to be in contact with a test sample can be treated or modified to become less adhesive or non-adhesive to molecules present in the test sample. By way of example only, the solid substrate surface can be silanized or coated with a polymer such that the solid substrate surface becomes inert and non-adhesive to any molecules present in a test sample. In other embodiments, a solid substrate surface can be modified or overlaid with a repellant or slippery surface. For example, a solid substrate surface can comprise a nano/microstructured substrate layer infused with a lubricating fluid, where the lubricating fluid is substantially immobilized on the substrate layer to form a repellant or slippery surface. In some embodiments, the repellant or slippery surface is known as Slippery Liquid-Infused Porous Surface (SLIPS), which is described in Wong T. S. et al., "Bioinspired self-repairing slippery surfaces with pressure-stable omniphobicity." (2011) Nature 477 (7365): 443-447, and International Application Nos. PCT/US12/21928 and PCT/US12/21929, the contents of which are incorporated herein by reference.

As used herein, by the "coating" or "coated" is generally meant a layer of molecules or material formed on a surface of a solid substrate. With respect to a coating of target-binding molecules on a solid substrate, the term "coating" or "coated" refers to a layer of target-binding molecules formed on a surface of a solid substrate. In some embodiments, the solid substrate surface can encompass an outer substrate surface and/or an inner substrate surface, e.g., with respect to a hollow structure. For example, the inner surface of a needle or catheter can be coated with target-binding molecules described herein. In one embodiment, the inner surface and/or outer surface of a hollow fiber can be coated with target-binding molecules described herein. In some embodiments, a cartridge can comprise a plurality of (e.g., at least 2 or more, including, e.g., at least 3, at least 4, at least 5, at least 10, at least 20, or more) hollow fibers having their inner surface and/or outer surface coated with target-binding molecules described herein. In one embodiment, the target-binding molecules coating a solid substrate surface can comprise microbe-binding molecules, e.g., for removing any microbe contaminants or fragments thereof from a fluid.

A solid substrate surface can be functionalized or activated for conjugation with target-binding molecules by any methods known in the art. Exemplary conjugations include, but are not limited to, covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, cyclodextrin/ adamantly host guest interaction) and the like. In some embodiments, a solid substrate surface can be functionalized with addition of silane coupling agents (e.g., but not limited to organosilanes, aminosilanes, vinyl silanes, methacryl silanes, and any combinations thereof).

Target-binding magnetic particles: In some embodiments, the target-binding agents can comprise target-binding magnetic particles. As used herein, the term "target-binding magnetic particles" refers to magnetic particles conjugated to target-binding molecules.

The target-binding magnetic particles can be paramagnetic, superparamagnetic, or ferromagnetic. In some embodiments, the target-binding magnetic particles can be paramagnetic or superparamagnetic. In some embodiments, the target-binding magnetic particles can have the same core magnetic particles as the magnetic field gradient concentrating particles, optionally with different surface properties, e.g., surface chemistry. In other embodiments, the core magnetic particles within the target-binding magnetic particles can be different from that of the magnetic field gradient concentrating particles.

The target-binding magnetic particles can range in size from 1 nm to 1 mm. For example, the target-binding magnetic particles can be about 2.5 nm to about 500 µm, or about 5 nm to about 250 µm in size. In some embodiments, the target-binding magnetic particles can be about 5 nm to about 100 µm in size. In some embodiments, the target-binding magnetic particles can be about 0.01 µm to about 10 µm in size. In some embodiments, the target-binding magnetic particles can be about 0.05 µm to about 5 µm in size. In some embodiments, the target-binding magnetic particles can be about 0.08 µm to about 1 µm in size. In one embodiment, the target-binding magnetic particles can be about 10 nm to about 10 µm in size. In some embodiments, the target-binding magnetic particles can have a size ranging from about 1 nm to about 1000 nm, from about 10 nm to about 500 nm, from about 25 nm to about 300 nm, from about 40 nm to about 250 nm, or from about 50 nm to about 200 nm. In one embodiment, the target-binding magnetic particles can have a size of about 50 nm to about 200 nm. The target-binding magnetic particles can be manipulated using magnetic field or magnetic field gradient. Such particles commonly consist of magnetic elements such as iron, nickel and cobalt and their oxide compounds. Magnetic microbeads are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199, the contents of which are incorporated herein by reference.

The target-binding magnetic particles can be of any shape, including but not limited to spherical, rod, elliptical, cylindrical, and disc.

Target-binding microparticles: The target-binding microparticle comprises at least one target-binding molecule on its surface. In some embodiments, the target-binding molecules can be pre-bound with a blocking agent described herein. The term "microparticle" as used herein refers to a particle having a particle size of about 0.001 µm to about 100 µm, about 0.005 µm to about 50 µm, about 0.01 µm to about 25 µm, about 0.05 µm to about 10 µm, or about 0.05 µm to about 5 µm. In one embodiment, the microparticle has a particle size of about 0.05 µm to about 1 µm. In one embodiment, the microparticle is about 0.09 µm-about 0.2 µm in size. It will be understood by one of ordinary skill in the art that microparticles usually exhibit a distribution of particle sizes around the indicated "size." Unless otherwise stated, the term "size" as used herein refers to the mode of a size distribution of microparticles, i.e., the value that occurs most frequently in the size distribution. Methods for measuring the microparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

The microparticles can be of any shape, e.g., a sphere. In some embodiments, the term "microparticle" as used herein can encompass a microsphere. The term "microsphere" as used herein refers to a microparticle having a substantially spherical form. A substantially spherical microparticle is a microparticle with a difference between the smallest radii and the largest radii generally not greater than about 40% of the smaller radii, and more typically less than about 30%, or less than 20%. In one embodiment, the term "microparticle" as used herein encompasses a microcapsule. The term "microcapsule" as used herein refers to a microscopic capsule that contains an active ingredient, e.g., a therapeutic agent.

In some embodiments, the microparticles can comprise biocompatible polymers as described herein.

In general, any biocompatible material well known in the art for fabrication of microparticles can be used in embodiments of the microparticle described herein. Accordingly, a microparticle comprising a lipidic microparticle core is also within the scope described herein. An exemplary lipidic microparticle core is, but is not limited to, a liposome. A liposome is generally defined as a particle comprising one or more lipid bilayers enclosing an interior, e.g., an aqueous interior. In one embodiment, a liposome can be a vesicle formed by a bilayer lipid membrane. Methods for the preparation of liposomes are well described in the art, e.g., Szoka and Papahadjopoulos (1980) *Ann. Rev. Biophys. Bioeng.* 9: 467, Deamer and Uster (1983) Pp. 27-51 In: *Liposomes*, ed. M. J. Ostro, Marcel Dekker, New York.

Target-binding microtiter plates: In some embodiments, the bottom surface of microtiter wells can be coated with the target-binding molecules described herein, e.g., for detecting and/or determining the amount of a target entity in a sample. In some embodiments, the target-binding molecules can be pre-bound with a blocking agent described herein. After a target entity in the sample displacing the blocking agent and binding to the target-binding molecules bound to the microwell surface, the rest of the sample can be removed. Detectable molecules that can also bind to a target entity (e.g., a target-binding molecule conjugated to a detectable molecules as described herein) can then be added to the microwells with the target entity for detection of the target entity. Various signal detection methods for determining the amount of proteins, e.g., using enzyme-linked immunosorbent assay (ELISA), with different detectable molecules have been well established in the art, and those signal detection methods can also be employed herein to facilitate detection of the signal induced by a target entity binding on the target-binding molecules.

Target-binding dipsticks/test strips: In some embodiments, the target-binding molecules can be adapted for use in a dipstick and/or a test strip for detection of a target entity. For example, a dipstick and/or a test strip can include at least one test area containing one or more target-binding molecules described herein. In some embodiments, the target-binding molecules can be conjugated or attached to a test area surface of the dipstick and/or a test strip. Methods for conjugating a protein to a solid substrate surface are known in the art, including, but not limited to direct cross-linking, indirect cross-linking via a coupling agent (e.g., a functional group, a peptide, a nucleic acid matrix such as DNA matrix), absorption, or any other art-recognized methods known in the art.

In some embodiments, the target-binding molecule(s) conjugated to the dipstick and/or a test strip can further comprise a detectable label as described herein. In some embodiments, the target-binding molecules can be pre-bound with a blocking agent described herein. In some embodiments, the dipstick and/or a test strip can further comprise at least one reference area or control area for comparison with a readout signal determined from the test area. The reference area generally excludes the target-binding molecules, e.g., to account for any background signal. In some embodiments, the reference area can include one or more known amounts of the detectable label that the target-binding molecules in the test area encompass. In such embodiments, the reference area can be used for calibration such that the amount of the target entity in a test sample can be estimated or quantified.

The dipstick and/or a test strip can be in any shape and/or in any format, e.g., a planar shape such as a rectangular strip or a circular disk, or a curved surface such as a stick. Alternatively, a continuous roll can be utilized, rather than discrete test strips, on which the test area(s) and optionally reference area(s) are present in the form of continuous lines or a series of spots.

The dipstick and/or a test strip can be made of any material, including, without limitations, paper, nitrocellulose, glass, plastic, polymer, membrane material, nylon, and any combinations thereof. In one embodiment, the dipstick and/or a test strip can include paper. In one embodiment, the dipstick and/or a test strip can include nylon.

The target-binding dipsticks and/or test strips described herein can be used as point-of-care diagnostic tools for detection of specific target entity such as microbes. By way of example only, a microbe-binding dipstick or test strip (e.g., made of membrane material such as nylon) comprising microbe-binding molecules and a blocking agent bound thereto can be brought into contact with a test sample (e.g., a blood sample) from a patient or a subject, and incubated for a period of time, e.g., at least about 15 seconds, at least about 30 seconds, at least about 1 min, at least about 2 mins, at least about 5 mins, at least about 10 mins, at least about 15 mins, at least about 30 mins, at least about 1 hour or more. Depending on different embodiments of the target-binding molecules, in some embodiments, the microbe-binding dipstick or test strip after contact with a test sample (e.g., a blood sample) can be further contacted with at least one additional agent to facilitate detection of microbes, and/or to increase specificity of the microbe detection. For example, some embodiments of the dipstick or test strip after contact with a test sample (e.g., a blood sample) can be further contacted with a detectable label that is conjugated to a molecule that binds to a microbe and/or microbial matter. Examples of such molecules can include, but are not limited to, one or more embodiments of the target-binding molecule described herein, an antibody specific for the microbes or pathogens to be detected, a protein, a peptide, a carbohydrate or a nucleic acid that is recognized by the microbes or pathogens to be detected, and any combinations thereof.

In some embodiments, the target-binding agent or substrates can be configured to detect and/or capture at least one microbe and/or a fragment thereof. Thus, in some embodiments, the target-binding agent or substrate can comprise a microbe-binding agent. By way of example only, a microbe-binding agent can comprise a carbohydrate recognition domain of a lectin (e.g., FcMBL), and/or any other microbe-binding molecules described in WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof") and the contents of which are incorporated herein by reference.

Target-binding molecules: The target-binding agent can be present in any form, including but not limited to a target-binding molecule, and/or a target-binding substrate (e.g., a target-binding molecule conjugated to a solid substrate) as described above. By "target-binding molecules" is meant herein molecules that can interact with or bind to a target species or a target analyte such that the target species or target analyte can be captured or isolated from a fluid sample. Typically the nature of the interaction or binding is noncovalent, e.g., by hydrogen, electrostatic, or van der Waals interactions, however, binding can also be covalent. Target-binding molecules can be naturally-occurring, recombinant or synthetic. Examples of the target-binding molecule can include, but are not limited to, a nucleic acid, an antibody or a portion thereof, an antibody-like molecule, an enzyme, an antigen, a small molecule, a protein, a peptide, a peptidomimetic, a carbohydrate, an aptamer, and any combinations thereof. By way of example only, in immunohistochemistry, the target-binding molecule can be an antibody specific to the target antigen to be analyzed. An ordinary artisan can readily identify appropriate target-binding molecules for each target species or analytes of interest to be detected in various bioassays.

In some embodiments, the target-binding molecules can be pre-bound with a blocking agent described herein.

In some embodiments, the target-binding molecules can be modified by any means known to one of ordinary skill in the art. Methods to modify each type of target-binding molecules are well recognized in the art. Depending on the types of target-binding molecules, an exemplary modification includes, but is not limited to genetic modification, biotinylation, labeling (for detection purposes), chemical modification (e.g., to produce derivatives or fragments of the target-binding molecule), and any combinations thereof. In some embodiments, the target-binding molecule can be genetically modified. In some embodiments, the target-binding molecule can be biotinylated.

In some embodiments, the target-binding molecules can comprise on their surfaces microbe-binding molecules as described herein, and/or disclosed in WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), the contents of which are incorporated herein by reference. Accordingly, in some embodiments, the method described herein can be used with the target-binding magnetic particles for microbial capture, i.e., microbe-binding magnetic particles, e.g., but not limited to FcMBL magnetic particles. Examples of microbe-binding magnetic particles can include, but are not limited to the ones described in WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), the contents of which are incorporated herein by reference.

In some embodiments, the target-binding molecule can be an antibody or a portion thereof, or an antibody-like molecule. In some embodiments, the target-binding molecule can be an antibody or a portion thereof, or an antibody-like molecule that is specific for detection of a rare-cell, e.g., a circulating tumor cell, a fetal cell, a stem cell and/or a microbe biomarker. In some embodiments, the target-binding molecule can be an antibody or a portion thereof, or an antibody-like molecule that is specific for a protein or an antigen present on the surface of a rare cell, e.g., a circulating tumor cell, a fetal cell, a stem cell and/or a microbe. In such embodiments, the target-binding molecules can be used to, for example, detect and/or identify cell type or species (including normal and/or diseased cells), the presence of cell or disease markers, cellular protein expression levels, phosphorylation or other post-translation modification state, or any combinations thereof.

In some embodiments, the target-binding molecule can be a nucleic acid (e.g., DNA, RNA, LNA, PNA, or any combinations thereof). For example, the nucleic acid can encode the gene specific for a rare cell biomarker, e.g., a circulating tumor cell, a fetal cell, a stem cell and/or a microbe biomarker. In such embodiments, the nucleic acids can be used to determine, for example, the existence of characteristic cellular DNA or RNA sequences (such as in fluorescent in situ hybridization), RNA expression levels, miRNA presence and expression, and any combinations thereof, in various applications, e.g., for disease diagnose, prognosis and/or monitoring.

In some embodiments, the target-binding molecule can be a protein or a peptide. In some embodiments, the protein or peptide can be essentially any proteins that can bind to a rare cell, e.g., a circulating tumor cell, a fetal cell, a stem cell and/or a microbe. By way of example only, if the target species is a bacteria, exemplary proteins or peptides that can be used to generate microbe-binding molecules and/or microbe-binding magnetic particles can include, but are not limited to, innate-immune proteins (e.g., without limitations, MBL, Dectin-1, TLR2, and TLR4 and any molecules (including recombinant or engineered protein molecules) disclosed here as well as the microbe-binding molecules disclosed in the International Application Publication Nos. WO/2011/090954 and WO/2013/012924, the content of which is incorporated herein by reference) and proteins comprising the chitin-binding domain, and any factions thereof. Such innate-immune proteins and chitin-binding domain proteins can be used to detect their corresponding pattern-recognition targets (e.g., microbes such as bacteria) and fungus, respectively.

In some embodiments, the target-binding molecule can be an aptamer. In some embodiments, the target-binding molecule can be a DNA or RNA aptamer. The aptamers can be used in various bioassays, e.g., in the same way as antibodies or nucleic acids described herein. For example, the DNA or RNA aptamer can encode a nucleic acid sequence corresponding to a rare cell biomarker or a fraction thereof, for use as a target-binding molecule on the magnetic particles described herein.

In some embodiments, the target-binding molecule can be a cell surface receptor ligand. As used herein, a "cell surface receptor ligand" refers to a molecule that can bind to the outer surface of a cell. Exemplary cell surface receptor ligand includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug. Additional cell surface receptor ligands include, but are not limited to, cytokines, growth factors, hormones, antibodies, and angiogenic factors. In some embodiments, any art-recognized cell surface receptor ligand that can bind to a rare cell, e.g., a circulating tumor cell, a fetal cell, a stem cell and/or a microbe, can be used as a target-binding molecule on the magnetic particles described herein.

Compositions Comprising a Target-binding Agent (or a Target-binding Substrate) and a Blocking Agent Various embodiments of the methods described herein can be adapted to various applications or be integrated as part of a process, e.g., but not limited to, antibody-based assays (e.g., ELISA), filtrations, microbe detection and/or capture, antibiotic susceptibility testings, multiplexing assays, coating processes, hybridization-based assays, diagnostic strips, targeted drug delivery, or any combinations thereof. Thus, various compositions comprising a target-binding agent and at least one blocking agent can be formulated to suit the need of each individual application. Accordingly, another aspect provided herein relates to a composition comprising one or more embodiments of a target-binding agent described herein, and at least one embodiment of a blocking agent described herein at a pre-determined concentration. In some embodiments, a composition can comprise one or more embodiments of a target-binding substrate described herein and at least one embodiment of a blocking agent described herein at a pre-determined concentration. The effective binding affinity of said at least one blocking agent for the target-binding agent is lower than the effective binding affinity of a target entity to be captured, and wherein the effective binding affinity of said at least one blocking agent for the target-binding agent is higher than the effective binding affinity of at least one interfering molecule present in a sample to be assayed for the target-binding agent.

In some embodiments, said at least one blocking agent can be pre-bound to the target-binding agent within the composition. In some embodiments, said at least one blocking agent can be pre-bound to the target-binding molecules present on the target-binding substrates. In alternative embodiments, said at least one blocking agent and the target-binding agent (or the target-binding substrate) can be kept separately within the composition, e.g., each is contained in a separate container. In some embodiments, the target-binding agent and said at least one blocking agent can each be independently present in a buffered solution.

In some embodiments, the target-binding agent can comprise an antibody (e.g., a primary antibody, and/or a secondary antibody). In these embodiments, by way of example only, the composition can be used during immunoglobulin secondary detection reactions, immunostaining, and/or ELISA assay.

In one embodiment, the addition of a blocking agent to a test sample in a competitive manner can be used in immunoglobulin secondary detection reactions. An example of such an application is described below: Fluorescent-labeled IgG1 has been raised to detect rabbit F(c) fragment for which IgG1 has high affinity. However, IgG1 also has a low affinity to goat F(c) and a medium affinity to an aptamer derived from the rabbit F(c) epitope. Thus, incubating HRP-labeled IgG1 in multiplex labeling assay where a goat primary Ab and a rabbit primary Ab are both used can result in the fluorescent labeling of both the goat and rabbit primary Abs.

In order to distinguish the labeling of both the goat and rabbit primary Abs, fluorescent-labeled IgG1 can be incubated with the aptamers (derived from the rabbit F(c) epitope) with a medium affinity prior to addition into a multiplex labeling assay where both a goat primary Ab and a rabbit are used. In this example, the high affinity ligand A is the rabbit Ab, the low affinity undesirable ligand B is the goat Ab and the intermediate affinity ligand C is the aptamer. The rabbit Ab (A) can displace the aptamers (C) that are bound to the fluorescent-labeled IgG1 but the goat Ab (B) is less likely to bind to the fluorescent-labeled IgG1 because the fluorescent-labeled IgG1 has already bound to the aptamers, which cannot be displaced by the goat Ab (B) with lower affinity. In some embodiments, the goat Ab (B) that is not bound to the first fluorescent-labeled IgG1 can be then detected with another fluorescent-labeled IgG1, thus enabling detection of different target entities in a multiplex labeling assay, e.g., using the same detection agent (e.g., IgG1) but with a different detectable label (e.g., a different fluorescent label) for each target entity (e.g., rabbit Ab and goat Ab).

In some embodiments, the target-binding agent can comprise a microbe-binding agent (e.g., FcMBL molecule). Examples of microbe-binding agent for detection and/or capture of microbes and/or fragments thereof are known in the art, including, e.g., microbe-binding molecules disclosed herein and in the International Application Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), the contents of which are incorporated herein by reference.

In some embodiments where the microbe-binding agent comprises a mannan-binding domain (e.g., FcMBL molecule), said at least one blocking agent can comprise glucose, maltose, N-acetyl muramic acid, and/or any combinations thereof. The pre-determined concentration of the blocking agent can vary with the binding affinity of the target entity for the target-binding agent. For example, a higher concentration of the blocking agent can be used without adversely affect the binding of the target-binding agent to the target entity with a higher effective binding affinity. In some embodiments where the glucose is the blocking agent, the pre-determined concentration of glucose can range from about 5 mM to about 200 mM.

In some embodiments, the blocking agent can further comprise a detectable label as described herein.

Kits Comprising a Composition Described Herein

A kit comprising at least one composition described herein is also provided. In some embodiments, the kit comprises a first composition comprising a first target-binding agent and at least one first blocking agent at a first pre-determined concentration, wherein the effective binding affinity of said at least one first blocking agent for the first target-binding agent is lower than the effective binding affinity of a first target entity to be captured, and wherein the effective binding affinity of said at least one first blocking agent for the first target-binding agent is higher than the effective binding affinity of at least one first interfering molecule present in a sample to be assayed for the first target-binding agent; and instructions for using the composition for detecting or capturing the first target entity.

In some embodiments, the kit can further comprise a second composition comprising a second target-binding agent. In some embodiments, the kit can further comprise at least one second blocking agent. The second blocking agent can be included in the kit at a second pre-determined concentration. In some embodiments, the effective binding affinity of a second blocking agent for the second target-binding agent can be lower than the effective binding affinity of a second target entity to be captured, and the effective binding affinity of the second blocking agent for the second target-binding agent can be higher than the effective binding affinity of at least one second interfering molecule present in the sample to be assayed for the second target-binding agent.

In some embodiments, the first blocking agent and the second blocking agent can be selected to prevent or reduce the binding of the same interfering agent to the first target-binding agent and the second target-binding agent, respectively. By way of example only, where said at least the first interfering agent and/or said at least the second interfering agent can be a non-specific binding molecule present in a sample, the first blocking agent and the second blocking agent can be selected to prevent or reduce the binding of non-specific binding molecules to the first target-binding agent and the second target-binding agent, respectively.

In some embodiments, the first blocking agent and the second blocking agent can be selected to prevent or reduce the binding of a different interfering agent to the first target-binding agent and the second target-binding agent, respectively. By way of example only, where the kit is adapted for use in a multiplexing assay, a first target entity can be intended to be detected by a first target-binding agent but not a second target-binding agent, while a second target entity can be intended to be detected by a second target-binding agent, but not a first target-binding agent. In these embodiments, the first target entity can be considered as said second interfering agent with respect to binding interaction between the second target-binding agent and the second target entity, and the second target entity can be considered as said first interfering agent with respect to binding interaction between the first target-binding agent and the first target entity. As used herein, the term "multiplexing" refers to simultaneous detection of more than one target entity, e.g., at least 2 target entities, at least 3 target entities, at least 4 target entities, or more.

In some embodiments, the first blocking agent can be pre-bound to the first target-binding agent. In some embodiments, the second blocking agent can be pre-bound to the second target-binding agent.

In some embodiments, the first target-binding agent can be affixed to a first solid substrate. In some embodiments, the first solid substrate can be further affixed with the second target-binding agent. In some embodiments, the second target-binding agent can be affixed to a second solid substrate. Non-limiting examples of the first or the second solid substrate includes, but are not limited to, a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combination thereof.

In some embodiments, the kit can further comprise a first detection agent capable of binding to the first target entity. In some embodiments, the kit can further comprise a second detection agent capable of binding to the second target entity.

In addition to the above mentioned components, any embodiments of the kits described herein can include informational material. The informational material can be descriptive, instructional, marketing or other material that relates to the methods described herein and/or the use of the aggregates for the methods described herein. For example, the informational material can describe methods for using the kits provided herein to perform an assay for capture and/or detection of a target entity, e.g., a microbe. The kit can also include an empty container and/or a delivery device, e.g., which can be used to deliver a test sample to a test container.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments, the kit can contain separate containers, dividers or compartments for each component and informational material. For example, each different component can be contained in a bottle, vial, or syringe, and the informational material can be contained in a plastic sleeve or packet. In other embodiments, the separate elements of the kit are contained within a single, undivided container. For example, a collection of the magnetic particles is contained in a bottle, vial or syringe that has attached thereto the informational material in the form of a label.

Test Sample or Sample

In accordance with various embodiments described herein, a test sample, including any fluid or specimen (processed or unprocessed) that is intended to be evaluated for the presence of a target entity can be subjected to methods, compositions, kits and systems described herein. The test sample or fluid can be liquid, supercritical fluid, solutions, suspensions, gases, gels, slurries, and combinations thereof. The test sample or fluid can be aqueous or non-aqueous.

In some embodiments, the test sample can be an aqueous fluid. As used herein, the term "aqueous fluid" refers to any flowable water-containing material that is suspected of comprising a pathogen.

In some embodiments, the test sample can include a biological fluid obtained from a subject. Exemplary biological fluids obtained from a subject can include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied stool sample, synovial fluid, lymphatic fluid, tears, tracheal aspirate, and any mixtures thereof. In some embodiments, a biological fluid can include a homogenate of a tissue specimen (e.g., biopsy) from a subject. In one embodiment, a test sample can comprises a suspension obtained from homogenization of a solid sample obtained from a solid organ or a fragment thereof.

In some embodiments, the test sample can be a whole blood sample obtained from a subject suspected of having a microbe infection (e.g., a pathogen infection).

In some embodiments, the test sample can include a fluid or specimen obtained from an environmental source. For example, the fluid or specimen obtained from the environmental source can be obtained or derived from food products or industrial food products, food produce, poultry, meat, fish, beverages, dairy products, water (including wastewater), surfaces, ponds, rivers, reservoirs, swimming pools, soils, food processing and/or packaging plants, agricultural places, hydrocultures (including hydroponic food farms), pharmaceutical manufacturing plants, animal colony facilities, and any combinations thereof.

In some embodiments, the test sample can include a fluid or specimen collected or derived from a biological culture. For example, a biological culture can be a cell culture. Examples of a fluid or specimen collected or derived from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the test sample can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

In some embodiments, the test sample can be a fluid or specimen collected or derived from a microbe colony.

In some embodiments, the test sample can include a media or reagent solution used in a laboratory or clinical setting, such as for biomedical and molecular biology applications. As used herein, the term "media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth.

As used herein, the term "reagent" refers to any solution used in a laboratory or clinical setting for biomedical and molecular biology applications. Reagents include, but are not limited to, saline solutions, PBS solutions, buffered solutions, such as phosphate buffers, EDTA, Tris solutions, and any combinations thereof. Reagent solutions can be used to create other reagent solutions. For example, Tris solutions and EDTA solutions are combined in specific ratios to create "TE" reagents for use in molecular biology applications.

In some embodiments, the test sample can be a non-biological fluid. As used herein, the term "non-biological fluid" refers to any fluid that is not a biological fluid as the term is defined herein. Exemplary non-biological fluids include, but are not limited to, water, salt water, brine, buffered solutions, saline solutions, sugar solutions, carbohydrate solutions, lipid solutions, nucleic acid solutions, hydrocarbons (e.g. liquid hydrocarbons), acids, gasolines, petroleum, liquefied samples (e.g., liquefied samples), and mixtures thereof Capture and/or Detection of a Microbe and/or Microbial Fragments/Matter in a Test Sample In some embodiments, the methods, compositions and/or kits described herein can be used for capture and/or detection a microbe and/or microbial fragments/matter in a test sample. Specifically, in some embodiments, the microbe-binding agents (e.g., FcMBL-coated magnetic particles or FcMBL-coated hollow fibers) can be pretreated with at least one blocking agent as described herein, prior to contacting a test sample with the microbe-binding agents (e.g., FcMBL-coated magnetic particles or FcMBL-coated hollow fibers). The blocking agent is selected to have an effective binding affinity for the microbe-binding agents (e.g., FcMBL-coated magnetic particles or FcMBL-coated hollow fibers) that is lower than the effective binding affinity of the microbes and/or fragments thereof for the microbe-binding agents (e.g., FcMBL-coated magnetic particles or FcMBL-coated hollow fibers); and wherein the blocking agent is selected to have the effective binding affinity for the microbe-binding agents (e.g., FcMBL-coated magnetic particles or FcMBL-coated hollow fibers) that is higher than the effective binding affinity of at least one interfering agent present in the sample for the microbe-binding agents (e.g., FcMBL-coated magnetic particles or FcMBL-coated hollow fibers). In these embodiments, the microbes or fragments thereof can displace the blocking agent bound to the microbe-binding agents (e.g., FcMBL-coated magnetic particles or FcMBL-coated hollow fibers) and become captured on the microbe-binding agents (e.g., FcMBL-coated magnetic particles or FcMBL-coated hollow fibers).

The high affinity binding of the captured microorganism can displace the blocking agent (e.g., sugar such as glucose) and prevent undesirable binding of blood cells and other non-target materials that would interfere with downstream detection/analysis processes, e.g., ATP-based detection of viable bacteria or downstream genetic amplification efficiency or immunoenzymatic detection. In one embodiment, when performing an assay using a dialysis-like therapeutic (DLT) device, e.g., as described in the International Application Publication No. WO/2012/135834, the content of which is incorporated herein by reference, FcMBL beads or membrane can be preloaded with a blocking agent (e.g., but not limited to, glucose and/or maltose) to not only enhance the capture of pathogens and microbial carbohydrate compounds but also to enhance magnetic bead recovery and prevent FcMBL inactivation by low affinity binders such as erythrocytes.

An example process for capture of a microbe and/or fragments thereof in a test sample comprises contacting a test sample with a microbe-binding agent. The microbe-binding agent can be pre-bound with a blocking agent as described herein, or added concurrently with a blocking agent to a test sample. After allowing microbes and/or fragments thereof, if present, to bind to the microbe-binding agent, e.g., by displacing the blocking agent from the microbe-binding agent, the microbe-binding agent comprising microbes and/or fragments thereof bound thereto can be separated from the test sample. In some embodiments, the microbes and/or fragments thereof can be detected and/or identified.

Figure 5:
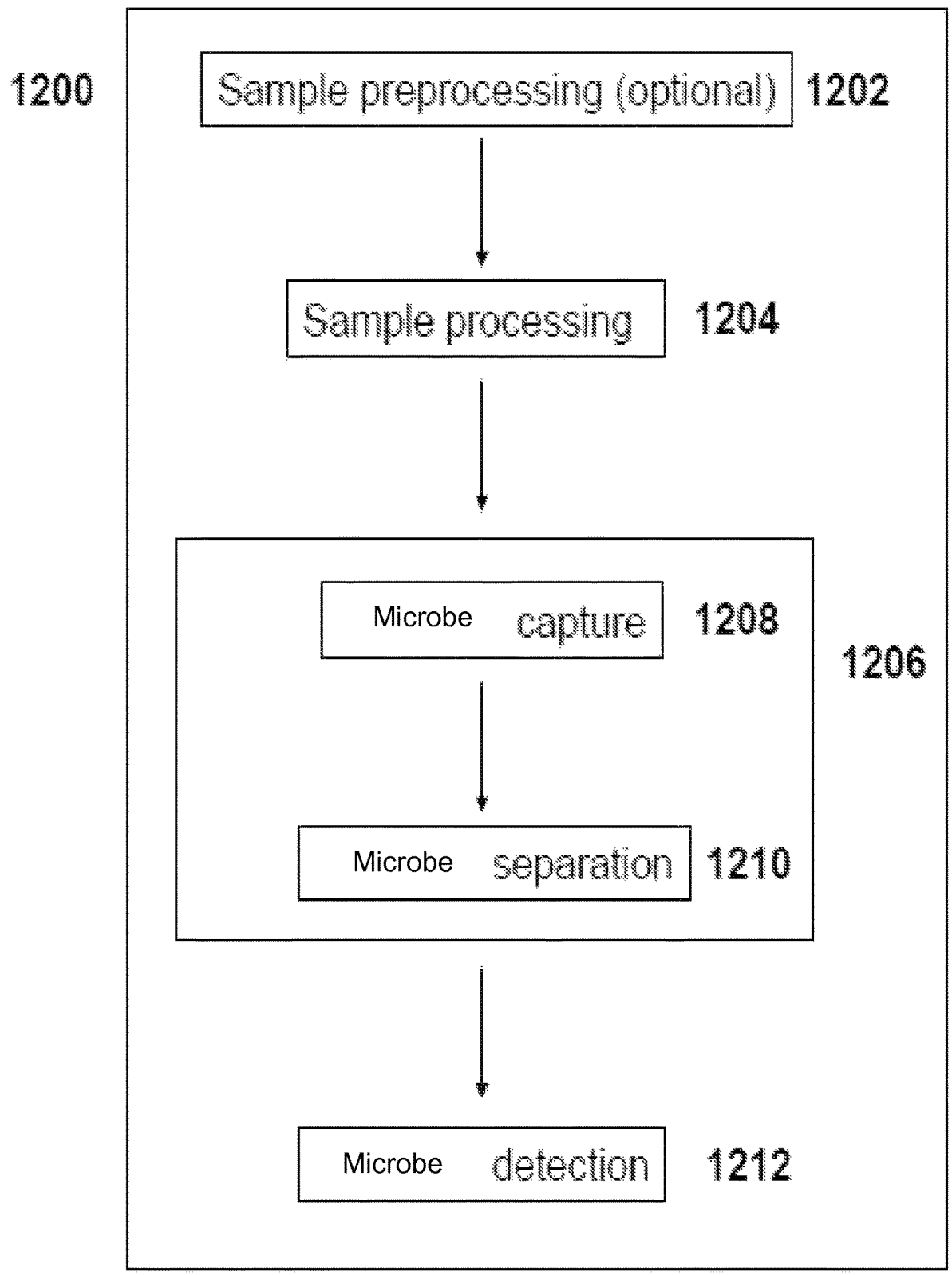
FIG. 5 is a schematic of an exemplary process comprising capture and detection of a microbe and/or microbial fragments/matter in a test sample.

An exemplary process for detecting a microbe (e.g., a pathogen) and/or microbial fragment/matter in a test sample is shown in FIG. 5. The process is provided for illustration purpose only, and one or more steps can be added, deleted, substituted and/or combined together. As shown in FIG. 5, the process 1200 comprises the optional step 1202 (preprocessing of the sample), step 1204 (processing of the sample), step 1206 comprising 1208 (microbe capture, e.g., pathogen capture) and 1210 (microbe separation, e.g., pathogen separation), step 1212 (detection of microbe and/or microbe identity and number), the optional step 1213 (microbe and/or detection agent immobilization), and the optional steps for antibiotic susceptibility testing, if desired, comprising step 1214 (incubation with the antibiotic agent) and step 1216 (detection of microbe number and/or viability). While these are discussed as discrete processes, one or more of the preprocessing, processing, capture, microbe separation, detection, and antibiotic sensitivity can be performed in a system. In one embodiment, one or more of the preprocessing, processing, capture, microbe separation, detection, and antibiotic sensitivity can be performed in a microfluidic device. In some embodiments, one or more of the microbe capture or separation, microbe incubation, and microbe detection can be included in a microfluidic device. In some embodiments, one or more of the modules or systems performing microbe capture or separation, microbe incubation, and microbe detection can comprise a microfluidic channel. Use of a microfluidic device can automate the process and/or allow processing of multiple samples at the same time. One of skill in the art is well aware of methods in the art for collecting, handling and processing biological fluids which can be used in the practice of the present disclosure. Additionally, the microfluidic devices for the various steps can be combined into one system for carrying out the method described herein. For example, such a system can comprise two or more of the following: (i) a capture or separation system for capturing a microbe from a biological fluid; (ii) an incubation system for incubating the microbe with or without an antibiotic agent; and (iii) a detection system for detecting the microbe after incubation. Alternatively, the various steps can also be carried out using separate systems or devices.

1202 (Sample Preprocessing): It can be necessary or desired that a test sample, such be preprocessed prior to microbe detection as described herein, e.g., with a preprocessing reagent. Even in cases where pretreatment is not necessary, preprocess optionally can be done for mere convenience (e.g., as part of a regimen on a commercial platform). A preprocessing reagent can be any reagent appropriate for use with the methods described herein.

The sample preprocessing step generally comprises adding one or more reagents to the sample. This preprocessing can serve a number of different purposes, including, but not limited to, hemolyzing cells such as blood cells, dilution of sample, etc. The preprocessing reagents can be present in the sample container before sample is added to the sample container or the preprocessing reagents can be added to a sample already present in the sample container. When the sample is a biological fluid, the sample container can be a VACUTAINER®, e.g., a heparinized VACUTAINER®.

The preprocessing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions.

In some embodiments, a preprocessing reagent is a surfactant or a detergent. In one embodiment, the preprocessing reagent is Triton X100.

After addition of the preprocessing reagent, the reagent can be mixed into the sample. This can be simply accomplished by agitating the sample, e.g., shaking the sample and/or moving the sample around in a microfluidic device.

1204 (Sample Processing): After the optional preprocessing step, the sample can be optionally further processed by adding one or more processing reagents to the sample. These processing reagents can degrade unwanted molecules present in the sample and/or dilute the sample for further processing. These processing reagents include, but are not limited to, surfactants and detergents, salts, cell lysing reagents, anticoagulants, degradative enzymes (e.g., proteases, lipases, nucleases, lipase, collagenase, cellulases, amylases, heparanases, and the like), and solvents, such as buffer solutions. Amount of the processing reagent to be added can depend on the particular sample to be analyzed, the time required for the sample analysis, identity of the microbe to be detected or the amount of microbe present in the sample to be analyzed.

It is not necessary, but if one or more reagents are to be added they can be present in a mixture (e.g., in a solution, "processing buffer") in the appropriate concentrations. Amount of the various components of the processing buffer can vary depending upon the sample, microbe to be detected, concentration of the microbe in the sample, or time limitation for analysis.

Generally, addition of the processing buffer can increase the volume of the sample by 5%, 10%, 15%, 20% or more. In some embodiments, about 50 µl to about 500 µl of the processing buffer are added for each ml of the sample. In some embodiments, about 100 µl to about 250 µl of the processing buffer are added for each ml of the sample. In one embodiment, about 125 µl of the processing buffer are added for each ml of the sample.

In some embodiments, a detergent or surfactant comprises about 5% to about 20% of the processing buffer volume. In some embodiment, a detergent or surfactant comprises about 5% to about 15% of the processing buffer volume. In one embodiment, a detergent or surfactant comprises about 10% of the processing buffer volume.

In some embodiments, one ml of the processing buffer comprises about 1U to about 100U of a degradative enzyme. In some embodiments, one ml of the processing buffer comprises about 5U to about 50U of a degradative enzyme. In one embodiment, one ml of the processing buffer comprises about 10U of a degradative enzyme. Enzyme unit (U) is an art known term for the amount of a particular enzyme that catalyzes the conversion of 1 µmol of substrate per minute.

In some embodiments, one ml of the processing buffer comprises about 1 µg to about 10 µg of an anti-coagulant. In some embodiment, one ml of the processing buffer comprises about 1 µg to about 5 µg of an anti-coagulant. In one embodiment, one ml of the processing buffer comprises about 4.6 µg of an anti-coagulant.

In some embodiments, one ml of the processing buffer comprises about 1 mg to about 10 mg of anti-coagulant. In some embodiment, one ml of the processing buffer comprises about 1 mg to about 5 mg of anti-coagulant. In one embodiment, one ml of the processing buffer comprises about 4.6 mg of anti-coagulant.

Exemplary anti-coagulants include, but are not limited to, heparin, heparin substitutes, salicylic acid, D-phenylalanyl-L-prolyl-L-arginine chloromethyl ketone (PPACK), Hirudin, ANCROD® (snake venom, VIPRONAX®), tissue plasminogen activator (tPA), urokinase, streptokinase, plasmin, prothrombopenic anticoagulants, platelet phosphodiesterase inhibitors, dextrans, thrombin antagonists/inhibitors, ethylene diamine tetraacetic acid (EDTA), acid citrate dextrose (ACD), sodium citrate, citrate phosphate dextrose (CPD), sodium fluoride, sodium oxalate, sodium polyanethol sulfonate (SPS), potassium oxalate, lithium oxalate, sodium iodoacetate, lithium iodoacetate and mixtures thereof.

Suitable heparinic anticoagulants include heparins or active fragments and fractions thereof from natural, synthetic, or biosynthetic sources. Examples of heparin and heparin substitutes include, but are not limited to, heparin calcium, such as calciparin; heparin low-molecular weight, such as enoxaparin (Lovenox®), Bemiparin, Certoparin, Dalteparin, Nadroparin, Parnaparin, Reviparin or Tinzaparin; heparin sodium, such as heparin, lipo-hepin, liquaemin sodium, and panheprin; heparin sodium dihydroergotamine mesylate; lithium heparin; and ammonium heparin.

Suitable prothrombopenic anticoagulants include, but are not limited to, anisindione, dicumarol, warfarin sodium, and the like.

Examples of phosphodiesterase inhibitors suitable for use in the methods described herein include, but are not limited to, anagrelide, dipyridamole, pentoxifyllin, and theophylline.

Suitable dextrans include, but are not limited to, dextran70, such as HYSKON™ (CooperSurgical, Inc., Shelton, Conn., U.S.A.) and MACRODEX™ (Pharmalink, Inc., Upplands Vasby, Sweden), and dextran 75, such as GENTRAN™ 75 (Baxter Healthcare Corporation).

Suitable thrombin antagonists include, but are not limited to, hirudin, bivalirudin, lepirudin, desirudin, argatroban, melagatran, ximelagatran and dabigatran.

As used herein, anticoagulants can also include factor Xa inhibitors, factor IIa inhibitors, and mixtures thereof. Various direct factor Xa inhibitors are known in the art including, those described in Hirsh and Weitz, Lancet, 93:203-241, (1999); Nagahara et al. Drugs of the Future, 20: 564-566, (1995); Pinto et al, 44: 566-578, (2001); Pruitt et al, Biorg. Med. Chem. Lett., 10: 685-689, (2000); Quan et al, J. Med. Chem. 42: 2752-2759, (1999); Sato et al, Eur. J. Pharmacol, 347: 231-236, (1998); Wong et al, J. Pharmacol. Exp. Therapy, 292:351-357, (2000). Exemplary factor Xa inhibitors include, but are not limited to, DX-9065a, RPR-120844, BX-807834 and SEL series Xa inhibitors. DX-9065a is a synthetic, non-peptide, propanoic acid derivative, 571 D selective factor Xa inhibitor. It directly inhibits factor Xa in a competitive manner with an inhibition constant in the nanomolar range. See for example, Herbert et al, J. Pharmacol. Exp. Ther. 276:1030-1038 (1996) and Nagahara et al, Eur. J. Med. Chem. 30(suppl):140s-143s (1995). As a non-peptide, synthetic factor Xa inhibitor, RPR-120844 (Rhone-Poulenc Rorer), is one of a series of novel inhibitors which incorporate 3-(S)-amino-2-pyrrolidinone as a central template. The SEL series of novel factor Xa inhibitors (SEL1915, SEL-2219, SEL-2489, SEL-2711: Selectide) are pentapeptides based on L-amino acids produced by combinatorial chemistry. They are highly selective for factor Xa and potency in the pM range.

Factor IIa inhibitors include DUP714, hirulog, hirudin, melgatran and combinations thereof. Melagatran, the active form of pro-drug ximelagatran as described in Hirsh and Weitz, Lancet, 93:203-241, (1999) and Fareed et al. Current Opinion in Cardiovascular, pulmonary and renal investigational drugs, 1:40-55, (1999).

Generally, salt concentration of the processing buffer can range from about 10 mM to about 100 mM. In some embodiments, the processing buffer comprises a salt at a concentration of about 25 mM to about 75 mM. In some embodiment, the processing buffer comprises a salt at a concentration of about 45 mM to about 55 mM. In one embodiment, the processing buffer comprises a salt at a concentration of about 43 mM to about 45 mM.

The processing buffer can be made in any suitable buffer solution known to a skilled artisan. In some embodiments, the buffer solution is physiologically compatible to cells. Alternatively, the processing buffer can be made in water.

In some embodiments, the processing buffer comprises a mixture of Triton-X, DNAse I, human plasmin, $CaCl_2$ and Polysorbate 20. In one embodiment, the processing buffer consists of a mixture of Triton-X, DNAse I, human plasmin, $CaCl_2$ and Polysorbate 20 in a TBS buffer.

In one embodiment, one ml of the processing buffer comprises 100 µl of Triton-X100, 10 µl of DNAse (1U/1 µl), 10 µl of human plasmin at 4.6 mg/ml and 870 µl of a mixture of TBS, 0.1% Polysorbate 20 and 50 mM $CaCl_2$.

Reagents and treatments for processing blood before assaying are also well known in the art, e.g., as used for assays on Abbott TDx, AxSYM®, and ARCHITECT® analyzers (Abbott Laboratories), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401, content of all of which is incorporated herein by reference. It is to be understood that one or more of these known reagents and/or treatments can be used in addition to or alternatively to the sample treatment described herein.

In some embodiments, after addition of the processing buffer, the sample comprises 1% Triton-X, 10U of DNase, 4.6 mg/ml of plasmin, 5 mM Calcium, 0.01% of Polysorbate 20, 2.5 mM of Tris, 150 mM of NaCl and 0.2 mM of KCl in addition to the components already present in the sample.

After addition of the processing reagents, the sample can be incubated for a period of time, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature.

1206 (1208 (Microbe Capture) and/or 1210 (Microbe Separation)): After processing of the sample, the sample can be subjected to a microbe capture process (step 1208). The microbe capture process can allow for concentrating and/or cleaning up the sample before proceeding with incubation with an antibiotic agent. Without limitations, any method known in the art for capturing or extracting or concentrating microbes from a biological sample (e.g., a biological fluid) can be used. A sample comprising the extracted microbes from the biological fluid is also referred to as a microbe sample herein.

The extraction and concentration process can be completed in less than 6 hours, less than 5 hours, less than 4 hours, less than 3 hours, less than 2 hours, less than 1 hour, less than 30 minutes, less than 15 minutes, less than 10 minutes, or shorter. In some embodiments, extraction and concentration of a microbe in the sample can be done within 10 minutes to 60 minutes of starting the process. In some embodiments, extraction and concentration of a microbe in the sample can be done in about 10 minutes, e.g., mixing a sample comprising a microbe to be extracted with at least one microbe-binding substrate (e.g., a plurality of microbe-binding magnetic particles described herein) followed by separation of the microbe-bound microbe-binding substrate from the rest of the sample.

Additionally, the extraction and concentration process described herein can be utilized to extract a microbe in a sample of any given volume. In some embodiments, sample volume is about 0.25 ml to about 50 ml, about 0.5 ml to about 25 ml, about 1 ml to about 15 ml, about 2 ml to about 10 ml. In some embodiments, sample volume is about 5 ml. In one embodiment, sample volume is 8 ml.

Generally, microbe capturing and isolating or separating microbes from the test sample comprises contacting the test sample (e.g., the biological fluid) with a microbe-binding molecule linked to a solid substrate or scaffold (e.g., beads, fibers, filters, beads, filters, fibers, screens, mesh, tubes, hollow fibers, fluidic channels, microfluidic channels, and the like) for capturing and isolating or separating microbes from the biological fluid.

The microbe capture process comprises mixing a solid substrate, surface of which is coated with microbe-binding molecules which can bind to a microbe in the sample. By "coated" is meant that a layer of microbe-binding molecules is present on a surface of the solid substrate and available for binding with a microbe. A solid substrate or a solid supporting structure coated with microbe-binding molecules is also referred to as a "microbe-binding substrate." The amount of the microbe-binding molecules used to coat a solid substrate surface can vary with a number of factors such as a solid substrate surface area, coating density, types of microbe-binding molecules, and binding performance. A skilled artisan can determine the optimum density of microbe-binding molecules on a solid substrate surface using any methods known in the art. By way of example only, the amount of the microbe-binding molecules used to coat a solid substrate can vary from about 1 wt % to about 30 wt % or from about 5 wt % to about 20 wt %. In some embodiments, the amount of the microbe-binding molecules used to coat the solid substrate can be higher or lower, depending on a specific need. However, it should be noted that if the amount of the microbe-binding molecules used to coat the substrate is too low, the microbe-binding substrate can show a lower binding performance with a microbe. On the contrary, if the amount of the microbe-binding molecules used to coat the substrate is too high, the dense layer of the microbe-binding molecules can exert an adverse influence on the binding properties.

In some embodiments, the microbe-binding substrate is a particle, e.g., a nano- or micro-particle. In some embodiments, the microbe-binding molecule coated substrate is a MBL, a recombinant MBL, FcMBL or AKT-FcMBL coated bead, microbead or magnetic microbead as described in the International Application Publication Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), contents of both of which are incorporated herein by reference. In some embodiments, the microbe-binding substrate can be coated with antibodies, aptamers, or nucleic acids against specific microbes, lectin (e.g., but not limited to MBL), or any combinations thereof.

After addition of the microbe-binding substrate, the microbe-binding substrate can be mixed in the sample to allow microbes to bind with the affinity molecule. This can be simply accomplished by agitating the sample, e.g., shaking the sample and/or moving the sample around in a microfluidic device.

In some embodiments, the microbe-binding substrate can be pretreated with the blocking agent as described herein, prior to contacting a test sample with the microbe-binding substrate. In some embodiments, a blocking agent and a test sample can be added to the microbe-binding substrate concurrently. The blocking agent is selected to have an effective binding affinity for the microbe-binding substrate that is lower than the effective binding affinity of the microbes and/or fragments thereof for the microbe-binding substrate; and wherein the blocking agent is selected to have the effective binding affinity for the microbe-binding substrate that is higher than the effective binding affinity of at least one interfering agent present in the sample for the microbe-binding substrate. In these embodiments, the microbes or fragments thereof displaces the blocking agent bound to the coated substrates (microbe-binding molecules) and becomes captured on the coated substrates.

The high affinity binding of the captured microorganism can displace the blocking agent (e.g., sugar such as glucose) and prevent undesirable binding of blood cells and/or other non-target materials that would interfere with downstream detection/analysis processes, e.g., ATP-based detection of viable bacteria or downstream genetic amplification efficiency or immunoenzymatic detection. While performing an assay using a dialysis-like therapeutic (DLT) device, e.g., as described in the International Application Publication No. WO 2012/135834, the content of which is incorporated herein by reference, FcMBL beads or membrane can be preloaded with a blocking agent (e.g., but not limited to, glucose or maltose) to not only enhance the capture of pathogens and microbial carbohydrate compounds but also to enhance magnetic bead recovery and prevent FcMBL inactivation by low affinity binders such as erythrocytes.

To prevent or reduce agglutination during separation of the microbes from the sample, additional reagents can be added to the sample mixture. For example, a reagent can be added to reduce agglutination by binding with an empty ligand binding site on the target-binding molecules.

1210 (Microbe Separation from Sample): The sample mixture is then subjected to a microbe separation process. Without wishing to be bound by a theory, in some embodiments, capture and separation of the bound microbes and/or fragments thereof from the sample can concentrate the microbes and/or fragments thereof. In some embodiments, capture and separation of the bound microbes and/or fragments thereof from the sample can deplete microbes and/or fragments thereof from a sample. In some embodiments, capture and separation of the bound microbes and/or fragments thereof from the sample can remove components which can interfere with the assay from the bound microbes and/or fragments thereof. Any method known in the art for separating the microbe-binding substrate from the sample can be employed.

For example, when the microbe-binding substrate is magnetic, e.g., a magnetic bead, a magnet can be employed to separate the substrate bound microbes from the sample fluid. Without limitations, microbe capture also can be carried out by non-magnetic means, for example, by coating microbe-binding molecules on non-magnetic solid substrates or scaffolds (e.g., beads, posts, fibers, filters, capillary tubes, etc.) and flow sample by these affinity substrates.

The skilled artisan is well aware of methods for carrying out magnetic separations. Generally, a magnetic field or magnetic field gradient can be applied to direct the magnetic beads. Optionally, the bound microbe can be washed with a buffer to remove any leftover sample and unbound components. Without wishing to be bound by a theory, capture and separation of the bound microbes from the sample can concentrate the microbes and also remove components, which can interfere with the assay or process, from the test sample.

In some embodiments where the microbe-binding agent is in a form of magnetic particles, a mixture of smaller microbe-binding magnetic particles and larger magnetic particles can be added to a test sample. The larger magnetic particles can act as local magnetic field gradient concentrators, thereby attracting the smaller microbe-bound microbe-binding magnetic particles to the larger magnetic particles and forming an aggregate, which in turn can be immobilized in the presence of a magnetic field gradient more readily than individual smaller microbe-binding magnetic particles. Thus, addition of magnetic particles that are larger than the microbe-binding magnetic particles can reduce loss of smaller microbe-bound microbe-binding particles to a fluid during each wash and/or magnetic separation. This concept of using larger magnetic particles to act as local magnetic field gradient concentrators can be extended to magnetic separation of any target-binding magnetic particles, and is described in U.S. Provisional Appl. No. 61/772,436 entitled "Methods for Magnetic Capture of a Target Molecule," the content of which is incorporated herein by reference.

In some embodiments, the magnetic field gradient can be generated by a magnetic field gradient generator described in the U.S. Provisional Application No. 61/772,360, entitled "Magnetic Separator."

In some embodiments, microbe capture and/or separation can be performed by flowing a test sample through a device comprising (i) a chamber with an inlet and an outlet, (ii) at least one capture element disposed in the chamber between the inlet and outlet, wherein the capture element has on its surface at least one microbe-binding molecule (e.g., FcMBL). An exemplary capture element can include, but is not limited to, a mixing element (e.g., a static mixer or a spiral mixer). Examples of such devices and methods of use are described in U.S. Provisional No. 61/673,071, entitled "Devices for Capturing a Microbe or Microbial Matter," the content of which is incorporated herein by reference.

In some embodiments, microbe capture and/or microbe-binding substrate separation can be performed by a rapid microbe diagnostic device as described in Int. Pat. App. No. WO 2011/091037, filed Jan. 19, 2011 (corresponding U.S. application Ser. No. 13/522,800), and/or WO 2012/135834 filed Apr. 2, 2012 (corresponding U.S. application Ser. No. 14/007,738), the contents of all of which are incorporated herein by reference. A rapid microbe diagnostic device as described in Int. Pat. App. No. WO 2011/091037, filed Jan. 19, 2011 (corresponding U.S. application Ser. No. 13/522, 800), the content of which is incorporated herein by reference, can be modified to replace the capture chamber or capture and visualization chamber with an s-shaped flow path. A magnet can then be used to capture bound microbe against the flow path wall; separating the bound microbe from rest of the sample.

Methods of separating or concentrating a microbe (e.g., a pathogen) from a biological sample are also described in the International Application Publication No. WO/2013/012924, (corresponding U.S. patent application Ser. No. 14/233,553), contents of which are incorporated herein by reference.

Without limitations, if a microbe-binding substrate does not possess a magnetic property, isolation of a microbe-binding substrate (e.g., particles, posts, fibers, dipsticks, membrane, filters, capillary tubes, etc.) from the test sample can be carried out by non-magnetic means, e.g., centrifugation, and filtration. In some embodiments where the microbe-binding substrate is in a form a dipstick or membrane, the microbe-binding dipstick or membrane can be simply removed from the test sample, where microbes, if any, in the test sample, remained bound to the engineered microbe-binding molecules conjugated to the dipstick or membrane substrate.

The extracted sample can optionally be washed any number (e.g., 1, 2, 3, 4, 5 or more) of times before microbial detection and/or incubation with an antibiotic agent, if desired, for antibiotic susceptibility testing. Without wishing to be bound by a theory, such washing can reduce and or eliminate any contaminants from the biological fluid that can be problematic during incubation or detection. In one embodiment, the microbe-binding substrate after isolated from the solution and/or the test sample can be washed with a buffer (e.g., but not limited to, TBST) for at least about 1-3 times.

Any art-recognized wash buffer that does not affect function/viability of the microbe bound on the microbe-binding substrate and does not interfere with binding of the microbe with the microbe-binding substrate can be used to wash the extracted or isolated microbe-bound microbe-binding substrates (e.g., but not limited to microbe-bound microbe-binding magnetic particles). Examples of a wash buffer can include, but are not limited to, phosphate-buffered saline, Tris-buffered saline (TBS), and a combination thereof. In some embodiments, the same processing buffer described herein without microbe-binding substrates (e.g., microbe-binding magnetic particles) and microbes can be used as the wash buffer. For example, in some embodiments, a wash buffer can include a mixture of TBS, 0.1% Polysorbate and 5 mM $Ca^{2+}$.

The amount of calcium ions ($Ca2+$) present in the processing buffer and/or wash buffer can vary from about 1 mM to about 100 mM, from about 3 mM to about 50 mM, or from about 5 mM to about 25 mM. Calcium ions can be obtained from any calcium salts, e.g., but not limited to, $CaCl_2$, $CaBr_2$, $CaI_2$, and $Ca(NO_3)_2$, and any other art-recognized calcium salts. Without wishing to be bound by theory, the presence of calcium ions in the processing buffer and/or wash buffer can facilitate and/or maintain calcium-dependent binding (e.g., lectin-mediated binding such as MBL-mediated binding) of the microbe to a microbe-binding substrate.

In some embodiments, the processing buffer and/or wash buffer can exclude calcium ions and/or include a chelator, e.g., but not limited to, EDTA. In such embodiments, microbes that solely depend on calcium-dependent binding (e.g., lectin-mediated binding such as MBL-mediated binding) to the microbe-binding substrate will less likely bind to the microbe-binding substrate in the absence of calcium ions. However, microbes (e.g., pathogens such as *S. aureus*) that at least partly depend on non-calcium-dependent interaction (e.g., but not limited to, protein A/Fc-mediated binding) with the microbe-binding substrate (e.g., FcMBL-coated magnetic particles) can bind to the microbe-binding substrate in the absence of calcium ions, and additional information can be found, e.g., in the International Application Publication No. WO/2013/012924, or in the U.S. Provisional App. No. 61/605,052 filed Feb. 29, 2012, the content of which is incorporated herein by reference.

In some embodiments, the capture or extraction from the biological fluid or other test samples can be accomplished by a method that does not require the identity of the microbe to be known for capture or extraction. This can be accomplished using a solid substrate coated with a broad-spectrum microbe-binding molecule for microbe extraction from the test sample. For example, in their previous work, the inventors described a method for the extraction and concentration of microbes (e.g., pathogens) from blood that does not require prior identification of pathogen. See PCT Application No. PCT/US2011/021603, filed Jan. 19, 2011, content of which is incorporated herein by reference. The method is based on beads that are coated with mannose binding lectin (MBL) or a genetically engineered version of MBL (FcMBL or Akt-FcMBL). MBL is a key component of the innate immune system, which binds to carbohydrate structures containing mannose, N-acetyl glucosamine and fucose on the surface of microbes or pathogens and that are not found on mammalian cells. MBL binds to at least 36 species of bacteria (e.g. Gram positive: Staphylococci, MRSA, VRSA, Streptococci, *Clostridium*; Gram negative: *Pseudomonas, E. coli, Klebsiella*,), 17 viruses (e.g. CMV, HIV, Ebola, HSV, HepB), 20 fungi (e.g., *Candida, Aspergillus, Cryptococcus*), and 9 parasites (e.g. Malaria, *Schistosoma*), in addition to at least one molecular toxin (e.g., LPS endotoxin). Consequently, MBL can serve as a broad-spectrum capture reagent, allowing a wide range of microbes (e.g., pathogens) to be extracted and concentrated from blood samples or other biological fluids.

Accordingly, in some embodiments of the aspects described herein, microbe capture or extraction from a biological sample or other test sample is by substrate coated with a broad-spectrum microbe-binding molecule. For example, microbe capture or extraction from a biological sample is by magnetic micro- or nano-beads as described in the International Application Publication Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), contents of both of which are incorporated herein by reference.

In some embodiments, adding a solid substrate coated with an anticoagulant to the extracted microbe sample can allow for better sample division, analysis or reproducibility. Without wishing to be bound by theory, addition of additional anticoagulant can reduce clumping of microbe-binding substrates. Accordingly, in some embodiments, anticoagulant coated substrate can be added to the test sample before or during or after the capture step. Without limitations, anticoagulant can be coated on a microbe-binding substrate (i.e. a solid substrate coated with a microbe-binding molecule). Generally, coating the substrate with an anticoagulant before coating with microbe-binding molecule provides substantially same efficiency as for a microbe-binding substrate that has not been coated with an anticoagulant. Alternatively, or in addition, a solid substrate coated only with anticoagulant can be added.

Any amount of anticoagulant coated substrate can be added to the test sample. For example, amount of anticoagulant coated substrate can be from about 5 wt % to about 500 wt % of the microbe-binding molecule coated substrate to be used for microbe extraction.

In some embodiments, about equal amounts of anticoagulant coated and microbe-binding molecule coated substrate can be added to the test sample.

1212 (Microbe Detection/Analysis): A detection component, device or system can be used to detect and/or analyze the presence of the separated microbe, for example, by spectroscopy, electrochemical detection, polynucleotide detection, fluorescence anisotropy, fluorescence resonance energy transfer, electron transfer, enzyme assay, magnetism, electrical conductivity, isoelectric focusing, chromatography, immunoprecipitation, immunoseparation, aptamer binding, filtration, electrophoresis, use of a CCD camera, immunoassay, ELISA, Gram staining, immunostaining, microscopy, immunofluorescence, western blot, polymerase chain reaction (PCR), RT-PCR, fluorescence in situ hybridization, sequencing, mass spectroscopy, or substantially any combination thereof. The separated microbe can remain bound on the microbe-binding substrate during detection and/or analysis, or be isolated form the microbe-binding substrate prior to detection and/or analysis.

In some embodiments, labeling molecules that can bind with the microbe can also be used to label the microbes for detection. As used herein, a "labeling molecule" refers to a molecule that comprises a detectable label and can bind with a target microbe. Labeling molecules can include, but are not limited to, MBL or a portion thereof, FcMBL, AKT-FcMBL, wheat germ agglutinin, lectins, antibodies (e.g., gram-negative antibodies or gram-positive antibodies, antibiotics to specific microbial strains or species), antigen binding fragments of antibodies, aptamers, ligands (agonists or antagonists) of cell-surface receptors and the like. The labeling molecule can also be a non-specific labeling molecule that non-specifically stains all viable cells in a sample.

As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices described herein.

A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments, the detectable label is a fluorophore or a quantum dot. Without wishing to be bound by a theory, using a fluorescent reagent can reduce signal-to-noise in the imaging/readout, thus maintaining sensitivity. Accordingly, in some embodiments, prior to detection, the microbes isolated from or remained bound on the microbe-binding substrate can be stained with at least one stain, e.g., at least one fluorescent staining reagent comprising a microbe-binding molecule, wherein the microbe-binding molecule comprises a fluorophore or a quantum dot. Examples of fluorescent stains include, but are not limited to, any microbe-binding element (e.g., microbe-specific antibodies or any microbe-binding proteins or peptides or oligonucleotides) typically conjugated with a fluorophore or quantum dot, and any fluorescent stains used for detection as described herein.

In some embodiments, a labeling molecule can be configured to include a "smart label", which is undetectable when conjugated to the microbe-binding molecules, but produces a color change when released from the engineered molecules in the presence of a microbe enzyme. Thus, when a microbe binds to the engineered microbe-binding molecules, the microbe releases enzymes that release the detectable label from the engineered molecules. An observation of a color change indicates presence of the microbe in the sample.

In some embodiments, the microbe-binding substrate can be conjugated with a label, such as a detectable label or a biotin label.

In some embodiments, the labeling molecule can comprise MBL or a microbe-binding molecule described herein. In one embodiment, the labeling molecule comprises FcMBL. Without wishing to be bound by a theory, labeling molecules based on MBL, and FcMBL in particular, attach selectively to a broad range of microbes, and so they enable the method described herein to detect the majority of blood-borne microbes with high sensitivity and specificity.

Any method known in the art for detecting the particular label can be used for detection. Exemplary methods include, but are not limited to, spectrometry, fluorometry, microscopy imaging, immunoassay, and the like. While the microbe capture step can specifically capture microbes, it can be beneficial to use a labeling molecule that can enhance this specificity. If imaging, e.g., microscopic imaging, is to be used for detecting the label, the staining can be done either prior to or after the microbes have been laid out for microscopic imaging. Additionally, imaging analysis can be performed via automated image acquisition and analysis.

For optical detection, including fluorescent detection, more than one stain or dye can be used to enhance the detection or identification of the microbe. For example, a first dye or stain can be used that can bind with a genus of microbes, and a second dye or strain can be used that can bind with a specific microbe. Colocalization of the two dyes then provides enhanced detection or identification of the microbe by reducing false positive detection of microbes.

In some embodiments, microscopic imaging can be used to detect signals from label on the labeling agent. Generally, the microbes in the subsample are stained with a staining reagent and one or more images taken from which an artisan can easily count the number of cells present in a field of view.

In particular embodiments, microbe can be detected through use of one or more enzyme assays, e.g., enzyme-linked assay (ELISA). Numerous enzyme assays can be used to provide for detection. Examples of such enzyme assays include, but are not limited to, beta-galactosidase assays, peroxidase assays, catalase assays, alkaline phosphatase assays, and the like. In some embodiments, enzyme assays can be configured such that an enzyme will catalyze a reaction involving an enzyme substrate that produces a fluorescent product. Enzymes and fluorescent enzyme substrates are known and are commercially available (e.g., Sigma-Aldrich, St. Louis, Mo.). In some embodiments, enzyme assays can be configured as binding assays that provide for detection of microbe. For example, in some embodiments, a labeling molecule can be conjugated with an enzyme for use in the enzyme assay. An enzyme substrate can then be introduced to the one or more immobilized enzymes such that the enzymes are able to catalyze a reaction involving the enzyme substrate to produce a detectable signal.

In some embodiments, an enzyme-linked assay (ELISA) can be used to detect signals from the labeling molecule. In ELISA, the labeling molecule can comprise an enzyme as the detectable label. Each labeling molecule can comprise one or more (e.g., 1, 2, 3, 4, 5, 6, 7, 8, 9, 10 or more) enzymes. Additionally, each labeling molecule can comprise one or more (e.g., 1, 2, 3, 4, 5, 6, 7, 8, 9, 10 or more) sites for binding with a microbe. Without wishing to be bound by a theory, presence of multimeric probe molecules can enhance ELISA signal.

For ELISA, any labeling molecule conjugated to an enzyme can be used. Exemplary labeling molecule include those comprising MBL, FcMBL, AKT-FcMBL, wheat germ agglutinin, lectins, antibodies (e.g., gram-negative antibodies or gram-positive antibodies), antigen binding fragments of antibodies, aptamers, ligands (agonists or antagonists) of cell-surface receptors and the like.

In some embodiments, the labeling molecule can comprise MBL or FcMBL labeled with a detectable label.

Similarly, a variety of enzymes can be used, with either colorimetric or fluorogenic substrates. In some embodiments, the reporter-enzyme produces a calorimetric change which can be measured as light absorption at a particular wavelength. Exemplary enzymes include, but are not limited to, beta-galactosidases, peroxidases, catalases, alkaline phosphatases, and the like.

In some embodiments, the enzyme is a horseradish peroxidase (HRP).

In some embodiments, the enzyme is an alkaline peroxidase (AP).

A microbe-binding molecule and the enzyme can be linked to each other by a linker. In some embodiments, the linker between the microbe-binding molecule and the enzyme is an amide bond. In some embodiments, the linker between the microbe-binding molecule and the enzyme is a disulfide (S—S) bond.

When the microbe-binding molecule is a peptide, polypeptide or a protein, the enzyme can be linked at the N-terminus, the C-terminus, or at an internal position of the microbe-binding molecule. Similarly, the enzyme can be linked by its N-terminus, C-terminus, or an internal position.

In one embodiment, the ELISA probe molecule can comprise a MBL or a portion there of or a FcMBL molecule linked to a HRP. Conjugation of HRP to any proteins and antibodies are known in the art. In one embodiment, FcMBL-HRP construct is generated by direct coupling HRP to FcMBL using any commercially-available HRP conjugation kit. In some embodiments, the microbes isolated from or remained bound on the microbe-binding substrate can be incubated with the HRP-labeled microbe-binding molecules, e.g., MBL or a portion thereof, or a FcMBL molecule linked to a HRP for a period of time, e.g., at least about 5 mins, at least about 10 mins, at least about 15 mins, at least about 20 mins, at least about 25 mins, at least about 30 mins. The typical concentrations of HRP-labeled molecules used in the ELISA assay can range from about 1:500 to about 1:20,000 dilutions. In one embodiment, the concentration of HRP-labeled microbe-binding molecules, e.g., MBL or a portion thereof, or a FcMBL molecule linked to a HRP molecule, can be about 1:1000 to about 1:10000 dilutions.

In one embodiment, the ELISA probe molecule can comprise a MBL or a portion thereof, or a FcMBL molecule linked to a AP. Conjugation of AP to any proteins and antibodies are known in the art. In one embodiment, FcMBL-AP construct is generated by direct coupling AP to FcMBL using any commercially-available AP conjugation kit. In some embodiments, the microbes isolated from or remained bound on the microbe-binding substrate can be incubated with the AP-labeled microbe-binding molecule, e.g., MBL or a portion thereof, or a FcMBL molecule linked to a AP for a period of time, e.g., at least about 5 mins, at least about 10 mins, at least about 15 mins, at least about 20 mins, at least about 25 mins, at least about 30 mins. The typical concentrations of AP-labeled molecules used in the ELISA assay can range from about 1:1000 to about 1:20,000 dilutions. In one embodiment, the concentration of AP-labeled microbe-binding molecules, e.g., MBL or a portion thereof, or a FcMBL molecule linked to a AP molecule, can be about 1:5000 to about 1:10000 dilutions.

Following incubation with the ELISA probe molecules, the sample can be washed with a wash buffer one or more (e.g., 1, 2, 3, 4, 5 or more) times to remove any unbound probes. An appropriate substrate for the enzyme (e.g., HRP or AP) can be added to develop the assay. Chromogenic substrates for the enzymes (e.g., HRP or AP) are known to one of skill in the art. A skilled artisan can select appropriate chromogenic substrates for the enzyme, e.g., TMB substrate for the HRP enzyme, or BCIP/NBT for the AP enzyme. In some embodiments, the wash buffer used after incubation with an ELISA probe molecule can contain calcium ions at a concentration of about at least about 0.01 mM, at least about 0.05 mM, at least about 0.1 mM, at least about 0.5 mM, at least about 1 mM, at least about 2.5 mM, at least about 5 mM, at least about 10 mM, at least about 20 mM, at least about 30 mM, at least about 40 mM, at least about 50 mM or more. In alternative embodiments, the wash buffer used after incubation with an ELISA probe molecule can contain no calcium ions. In some embodiments, the wash buffer used after incubation with an ELISA probe molecule can contain a chelating agent. A wash buffer can be any art-recognized buffer used for washing between incubations with antibodies and/or labeling molecules. An exemplary wash buffer can include, but is not limited to, TBST.

In some embodiments, without wishing to be bound by theory, it can be desirable to use a wash buffer without a surfactant or a detergent for the last wash before addition of a chromogenic substrate, because a surfactant or detergent may have adverse effect to the enzymatic reaction with a chromogenic substrate.

One advantage of the ELISA-based approach is that the solid substrate does not need to be dispersed or dissociated from the microbe before binding the secondary reagents. This is in contrast to microscopic techniques, in which excess residual solid substrate may obscure the microbe during imaging. Furthermore, the optical readout components for ELISA are likely cheaper than in the microscopy case, and there is no need for focusing or for demanding that the sample be on the same focal plane. A further advantage of the ELISA-based approach is that it can take advantage of commercially available laboratory equipment. In particular, when the solid substrate is magnetic, magnetic separation can be automated using the KINGFISHER® system, the brief culture can be performed using an airlift fermenter, and the colorimetric/fluorescent readout can be attained using a standard plate reader.

Further amplification of the ELISA signal can be obtained by multimerizing the recognition molecule (e.g., the microbe-binding molecule) or by multimerizing the detection enzyme (HRP, etc.). For instance, phage expression can be used to yield multimerized MBL and provide a scaffold to increase the concentration of HRP (either through direct coupling of HRP to the phage particles or using an HRP-antiM13 conjugated antibody).

In some embodiments, microbe can be detected through use of immunoassay. Numerous types of detection methods may be used in combination with immunoassay based methods.

Without limitations, detection of microbes in a sample can also be carried out using light microscopy with phase contrast imaging based on the characteristic size (5 um diameter), shape (spherical to elliptical) and refractile characteristics of target components such as microbes that are distinct from all normal blood cells. Greater specificity can be obtained using optical imaging with fluorescent or cytochemical stains that are specific for all microbes or specific subclasses (e.g. calcofluor (1 µM to 100 µM) for chitin in fungi, fluorescent antibodies directed against fungal surface molecules, gram stains, acid-fast stains, fluorescent MBL, fluorescent Fc-MBL, etc.).

In some embodiments, a microbe can be detected through use of spectroscopy. Numerous types of spectroscopic methods can be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, a metabolic assay is used to determine the relative number of microbes in a sample compared to a control. As will be apparent to one of ordinary skill in the art any metabolic indicator that can be associated with cells can be used, such as but not limited to, turbidity, fluorescent dyes, and redox indicators such as, but not limited to, Alamar Blue, MTT, XTT, MTS, and WST. Metabolic indicators can be components inherent to the cells or components added to the environment of the cells. In some embodiments, changes in or the state of the metabolic indicator can result in alteration of ability of the media containing the sample to absorb or reflect particular wavelengths of radiation.

In some embodiments, microbes isolated from or remained bound on microbe-binding substrate can be labeled with nucleic acid barcodes for subsequent detection and/or multiplexing detection. Nucleic acid barcoding methods for detection of one or more analytes in a sample are well known in the art.

In other embodiments, the captured microbe can be analyzed and/or detected in the capture chamber or capture and visualization chamber of a rapid microbe diagnostic device described in the Int. Pat. App. No. WO 2011/091037, filed Jan. 19, 2011 (corresponding U.S. application Ser. No. 13/522,800), the contents of which are incorporated herein by reference. Alternatively, the captured microbe can be recovered (i.e., removed) and analyzed and/or detected.

In some embodiments, the captured microbe is recovered and analyzed and/or detected using a particle on membrane assay as described in U.S. Pat. No. 7,781,226, content of which is incorporated herein by reference. A particle on membrane assay as described in U.S. Pat. No. 7,781,226 can be operably linked with a rapid microbe diagnostic device of the Int. Pat. App. No. WO 2011/091037 (corresponding U.S. application Ser. No. 13/522,800), the contents of which are incorporated herein by reference, to reduce the number of sample handling steps, automate the process and/or integrate the capture, separation and analysis/detection steps into a microfluidic device.

In some embodiments, microbe capture, separation and analysis can be done using a hybrid microfluidic SPR and molecular imagining device as described in U.S. Pat. App. Pub. No. US 2011/0039280.

In some embodiments, microbe detection and/or identification can use one or more embodiments of the compositions and/or methods described in the International Application No. PCT/US12/71398 filed Dec. 21, 2012, content of which is incorporated herein by reference.

In some embodiments, the processes or assays described herein can detect the presence or absence of a microbe and/or identify a microbe in a test sample in less than 24 hours, less than 12 hours, less than 10 hours, less than 8 hours, less than 6 hours, less than 4 hours, less than 3 hours, less than 2 hours, less than 1 hour, or lower. In some embodiments, the processes or assays described herein can detect the presence or absence of a microbe and/or identify a microbe in a test sample in less than 6 hours, less than 4 hours, less than 3 hours, less than 2 hours, less than 1 hour, or lower.

Optional additional analyses or treatment—culturing: In some embodiments of any aspects described herein, the assay or process can further comprise culturing any microbe bound on the microbe-binding substrate (e.g., microbe-binding magnetic microbeads) for a period of time. In such embodiments, the microbe bound on the microbe-binding substrate can expand in population by at least about 10% after culturing for a period of time.

In some embodiments, the microbes bound on the microbe-binding substrates (e.g., microbe-binding magnetic microbeads) can be cultured on a microbe-compatible culture medium, e.g., plated on an agar plate or cultured in LB broth. One of skill in the art will readily recognize microbial culture techniques, including, but not limited to, the use of incubators and/or equipment used to provide a gentle agitation, e.g., rotator platforms, and shakers, if necessary, e.g., to prevent the cells from aggregation without subjecting them to a significant shear stress and provide aerial agitation.

The microbes can remain bound on the microbe-binding substrate (e.g., microbe-binding magnetic microbeads) during detection and/or additional analyses described herein or they can be detached, eluted off or removed from a microbe-binding substrate prior to detection or additional analyses described herein. In some embodiments where the bound microbes are desired to be detached, eluted off or removed from a microbe-binding substrate, the microbe-binding molecules of the microbe-binding substrate can be further contacted with a low pH buffer, e.g., a pH buffer less than 6, less than 5, less than 4, less than 3, less than 2, less than 1 or lower. In some embodiments, a low pH buffer that does not cause precipitation of a chelating agent, if present, can be used. In one embodiment, a low pH buffer can be arginine. In another embodiment, a low pH buffer can be pyrophosphate.

In some embodiments of any aspects described herein, the microbe-binding molecules of the microbe-binding substrate can be further contacted with a low pH buffer and a chelating agent. In some embodiments, the contact of the microbe-binding molecules of the microbe-binding substrate with the low pH buffer and the chelating agent can be concurrent or sequentially. In one embodiment, the microbe-binding molecules of the microbe-binding substrate can be further contacted with arginine (e.g., 2 M) with EDTA or EGTA at pH 4.4.

The isolated microbes can then be used for analyses described earlier or additional treatment, e.g., expansion in culture, antibiotic sensitivity testing, sequencing and/or DNA or RNA analysis.

Optional additional analyses or treatment—antibiotic sensitivity or susceptibility testing: In some embodiments of any aspects described herein, the process or assay described herein can further comprise subjecting the microbes bound on the microbe-binding substrate (e.g., microbe-binding magnetic microbeads) and/or the expanded cultures of microbes isolated from the microbe-binding substrate (e.g., microbe-binding magnetic microbeads) to one or more antibiotics. The response of the microbe to an antibiotic can then be evaluated with any known methods in the art, e.g., by measuring the viability of microbes. Thus, an appropriate antibiotic can be identified for treatment of an infection caused by a microbe, even though the specific species of the microbe bound onto the microbe-binding substrate is initially unknown. Additional details for use of engineered microbe-binding molecules described herein in antibiotic sensitivity testings can be found, e.g., in the International Application No. PCT/US13/28409 filed Feb. 28, 2013.

Any processes or steps described herein can be performed by a module or device. While these are discussed as discrete processes, one or more of the processes or steps described herein can be combined into one system for carrying out the assays of any aspects described herein.

In some embodiments, the assay or process 1200 described herein can be adapted for use in a high-throughput platform, e.g., an automated system or platform.

Microbe-binding Agents or Molecules

In some embodiments, the target-binding agents comprise microbe-binding agents or molecules. In some embodiments, the target-binding molecules comprise microbe-binding molecules. In some embodiments, the blocking agent is pre-bound to the microbe-binding agents or microbe-binding molecules. Any molecule or material that can bind to a microbe can be employed as the microbe-binding molecule. Exemplary microbe-binding molecules (or microbe-binding molecules) include, but are not limited to, opsonins, lectins, antibodies and antigen binding fragments thereof, proteins, peptides, nucleic acids, carbohydrates, lipids, and any combinations thereof. The microbe-binding molecule can comprise at least one (e.g., one, two, three, four, five, six, seven, eight, nine, ten, eleven, twelve, thirteen, fourteen, fifteen, sixteen, seventeen, eighteen, nineteen, twenty or more) microbe surface-binding domain ("microbe binding domain"). The term "microbe surface-binding domain" as used herein refers to any molecules or a fragment thereof that can specifically bind to the surface of a microbe, e.g., any component present on a surface of a microbe.

Materials or substances which can serve as microbe-binding molecules include, for example, peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof. The microbe-binding molecule can be covalently (e.g., cross-linked) or non-covalently linked to the substrate surface.

In some embodiments, the microbe surface-binding domain can comprise an opsonin or a fragment thereof. The term "opsonin" as used herein refers to naturally-occurring and synthetic molecules which are capable of binding to or attaching to the surface of a microbe or a pathogen, of acting as binding enhancers for a process of phagocytosis. Examples of opsonins which can be used in the engineered molecules described herein include, but are not limited to, vitronectin, fibronectin, complement components such as C1q (including any of its component polypeptide chains A, B and C), complement fragments such as C3d, C3b and C4b, mannose-binding protein, conglutinin, surfactant proteins A and D, C-reactive protein (CRP), alpha2-macroglobulin, and immunoglobulins, for example, the Fc portion of an immunoglobulin.

In some embodiments, the microbe surface-binding domain comprises a carbohydrate recognition domain or a carbohydrate recognition portion thereof. As used herein, the term "carbohydrate recognition domain" refers to a region, at least a portion of which, can bind to carbohydrates on a surface of a microbe (e.g., a pathogen).

In some embodiments, the microbe surface-binding domain comprises a lectin or a carbohydrate recognition or binding fragment or portion thereof. The term "lectin" as used herein refers to any molecules including proteins, natural or genetically modified, that interact specifically with saccharides (i.e., carbohydrates). The term "lectin" as used herein can also refer to lectins derived from any species, including, but not limited to, plants, animals, insects and microorganisms, having a desired carbohydrate binding specificity. Examples of plant lectins include, but are not limited to, the Leguminosae lectin family, such as ConA, soybean agglutinin, peanut lectin, lentil lectin, and *Galanthus nivalis* agglutinin (GNA) from the *Galanthus* (snowdrop) plant. Other examples of plant lectins are the Gramineae and Solanaceae families of lectins. Examples of animal lectins include, but are not limited to, any known lectin of the major groups S-type lectins, C-type lectins, P-type lectins, and I-type lectins, and galectins. In some embodiments, the carbohydrate recognition domain can be derived from a C-type lectin, or a fragment thereof. C-type lectin can include any carbohydrate-binding protein that requires calcium for binding. In some embodiments, the C-type lectin can include, but not be limited to, collectin, DC-SIGN, and fragments thereof. Without wishing to be bound by theory, DC-SIGN can generally bind various microbes by recognizing high-mannose-containing glycoproteins on their envelopes and/or function as a receptor for several viruses such as HIV and Hepatitis C.

In some embodiments, the microbe-binding molecules or microbe-binding molecules can comprise a microbe-binding portion of the C-type lectins, including, e.g., but not limited to, soluble factors such as Collectins (e.g., MBL, surfactant protein A, surfactant protein D and Collectin 11), ficolins (e.g. L-Ficolin, Ficolin A), receptor based lectins (e.g., DC-SIGN, DC-SIGNR, SIGNR1, Macrophage Mannose Receptor 1, Dectin-1 and Dectin-2), lectins from the shrimp *Marsupenaeus japonicus* (e.g. Lectin A, Lectin B and Lectin C), or any combinations thereof.

In some embodiments, the microbe-binding molecules can comprise at least a portion of non-C-type lectins (e.g., but not limited to, Wheat Germ Agglutinin).

In some embodiments, the microbe-binding molecules can comprise at least a portion of lipopolysaccharide (LPS)-binding proteins and/or endotoxin binding proteins (e.g., but not limited to, CD14, MD2, lipopolysaccharide binding proteins (LBP), limulus anti-LPS factor (LAL-F), or any combinations thereof).

In some embodiments, the microbe-binding molecules can comprise at least a portion of peptidoglycan binding proteins (e.g., but not limited to, mammalian peptidoglycan recognition protein-1 (PGRP-1), PGRP-2, PGRP-3, PGRP-4, or any combinations thereof.

Collectins are soluble pattern recognition receptors (PRRs) belonging to the superfamily of collagen containing C-type lectins. Exemplary collectins include, without limitations, mannan-binding lectin (MBL) or mannose-binding protein, surfactant protein A (SP-A), surfactant protein D (SP-D), collectin liver 1 (CL-L1), collectin placenta 1 (CL-P1), conglutinin, collectin of 43 kDa (CL-43), collectin of 46 kDa (CL-46), and a fragment thereof.

In some embodiments, the microbe-surface binding domain comprises the full amino acid sequence of a carbohydrate-binding protein. In some embodiments, the microbe-surface binding domain comprises a sequence of a carbohydrate recognition domain of a carbohydrate-binding protein. Examples of carbohydrate-binding proteins include, but are not limited to, lectin, collectin, ficolin, mannose-binding lectin (MBL), maltose-binding protein, arabinose-binding protein, glucose-binding protein, *Galanthus nivalis* agglutinin, peanut lectin, lentil lectin, DC-SIGN, C-reactive protein (CRP), and any combinations thereof.

In some embodiments, the microbe surface-binding molecule comprises a mannose-binding lectin (MBL) or a carbohydrate binding fragment or portion thereof. Mannose-binding lectin, also called mannose binding protein (MBP), is a calcium-dependent serum protein that can play a role in the innate immune response by binding to carbohydrates on the surface of a wide range of microbes or pathogens (viruses, bacteria, fungi, protozoa) where it can activate the complement system. MBL can also serve as a direct opsonin and mediate binding and uptake of microbes or pathogens by tagging the surface of a microbe or pathogen to facilitate recognition and ingestion by phagocytes. MBL and an engineered form of MBL (FcMBL and Akt-FcMBL) are described in the International Application Publication Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), contents of both of which are incorporated herein by reference.

In some embodiments, the microbe surface-binding molecule comprises at least a portion of C-reactive protein that binds to a microbe or fragment thereof. Microbe-binding molecules comprising a portion of C-reactive protein described in U.S. Provisional App. No. 61/917,705 entitled "CRP Capture/Detection of Gram Positive Bacteria," the contents of which are incorporated herein by reference.

Without wishing to be bound by a theory, microbe binding molecules comprising lectins or modified versions thereof can act as broad-spectrum microbe binding molecules (e.g., pathogen binding molecules). Accordingly, antibiotic susceptibility method utilizing lectins (e.g., MBL and genetically engineered version of MBL (FcMBL and Akt-FcMBL)) as broad-spectrum microbe binding molecules (e.g., pathogen binding molecules) to capture and grow the microbes, can be carried out without identifying the microbe (e.g., pathogen), either for extraction or for antibiotic sensitivity testing.

In some embodiments, at least two microbe surface-binding domains (e.g. two, three, four, five, six, seven or more) microbe surface-binding domains, can be linked together to form a multimeric microbe surface-binding domain. In such embodiments, the distances between microbe surface-binding domains can be engineered to match with the distance between the binding sites on the target microbe surface. In some embodiments, the microbe surface-binding domain can be present in a form of a monomer, dimer, trimer, tetramer, pentamer, hexamer, or an entity comprising more than six sub-units.

A multimeric microbe surface-binding domain can have each of the individual microbe surface-binding domains be identical. Alternatively, a multimeric microbe surface-binding domain can have at least one, at least two, or at least three microbe surface-binding domains different from the rest. In such embodiments, microbe surface-binding domains that share a common binding specificity for molecule on a microbe surface can be used. By way of example only, the fibrinogen-like domain of several lectins has a similar function to the CRD of C-type lectins including MBL, and function as pattern-recognition receptors to discriminate microbes or pathogens from self. One of such lectins comprising the fibrinogen-like domain is serum ficolins.

Serum ficolins have a common binding specificity for GlcNAc (N-acetyl-glucosamine), elastin or GalNAc (N-acetyl-galactosamine). The fibrinogen-like domain is responsible for the carbohydrate binding. In human serum, two types of ficolin, known as L-ficolin (also called P35, ficolin L, ficolin 2 or hucolin) and H-ficolin (also called Hakata antigen, ficolin 3 or thermolabile b2-macroglycoprotein), have been identified, and both of them have lectin activity. L-ficolin recognizes GlcNAc and H-ficolin recognizes GalNAc. Another ficolin known as M-ficolin (also called P3 5-related protein, ficolin 1 or ficolin A) is not considered to be a serum protein and is found in leucocytes and in the lungs. L-ficolin and H-ficolin activate the lectin-complement pathway in association with MASPs. M-Ficolin, L-ficolin and H-ficolin have calcium-independent lectin activity. Accordingly, in some embodiments, a microbe-binding molecule can comprise MBL and L-ficolin carbohydrate recognition domains, MBL and H-ficolin carbohydrate recognition domains, or a combination thereof.

Any art-recognized recombinant carbohydrate-binding proteins or carbohydrate recognition domains can also be used in the microbe-binding molecules. For example, recombinant mannose-binding lectins, e.g., but not limited to, the ones disclosed in the U.S. Pat. Nos. 5,270,199; 6,846,649; and U.S. Patent App. Publication No. US 2004/0229212, contents of all of which are incorporated herein by reference, can be used in constructing a microbe-binding molecule.

The microbe binding molecule can further comprise at least one (e.g., one, two, three, four, five, six, seven, eight, nine, ten, eleven, twelve, thirteen, fourteen, fifteen, sixteen, seventeen, eighteen, nineteen, twenty or more) substrate surface binding domain ("substrate binding domain") adapted for orienting the microbe binding domain away from the substrate surface. As used herein, the term "substrate-binding domain" refers to any molecule that facilitates the conjugation of the engineered molecules described herein to a solid substrate or a functionalized substrate. The microbe binding domain and the substrate binding domains can be linked by a linker. Similarly, the substrate binding domain and the substrate surface can be linked by a linker.

The substrate-binding domain can comprise at least one amino group that can non-covalently or covalently couple with functional groups on the surface of the substrate. For example, the primary amines of the amino acid residues (e.g., lysine or cysteine residues) at the N-terminus or in close proximity to the N-terminus of the microbe surface-binding domains can be used to couple with functional groups on the substrate surface.

In some embodiments, the substrate-binding domain can comprise at least one, at least two, at least three or more oligopeptides. The length of the oligonucleotide can vary from about 2 amino acid residues to about 10 amino acid residues, or about 2 amino acid residues to about 5 amino acid residues. Determination of an appropriate amino acid sequence of the oligonucleotide for binding with different substrates is well within one of skill in the art. For example, an oligopeptide comprising an amino acid sequence of Alanine-Lysine-Threonine (AKT), which provides a single biotinylation site for subsequent binding to streptavidin-coated substrate. Such single biotinylation site can also enable the microbe surface binding domain of a microbe binding molecule to orient away from the substrate, and thus become more accessible to microbes or pathogens. See, for example, Witus et al. (2010) JACS 132: 16812.

In some embodiments, the substrate-binding domain can comprise at least one oligonucleotide. The sequence and length of the oligonucleotides can be configured according to the types of the substrate, binding density, and/or desired binding strength. For example, if the substrate is a nucleic acid scaffold, e.g., a DNA scaffold, the oligonucleotide sequence of the substrate-binding domain can be designed such that it is complementary to a sub-sequence of the nucleic acid scaffold to where the substrate-binding domain can hybridize.

In some embodiments, the oligonucleotides can include aptamers. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art. The oligonucleotides including aptamers can be of any length, e.g., from about 1 nucleotide to about 100 nucleotides, from about 5 nucleotides to about 50 nucleotides, or from about 10 nucleotides to about 25 nucleotides. Generally, a longer oligonucleotide for hybridization to a nucleic acid scaffold can generate a stronger binding strength between the engineered microbe surface-binding domain and substrate.

The microbe-binding molecules can contain sequences from the same species or from different species. For example, an interspecies hybrid microbe-binding molecule can contain a linker, e.g., a peptide linker, from a murine species, and a human sequence from a carbohydrate recognition domain protein, provided that they do not provide unacceptable levels of deleterious effects. The engineered microbe-binding molecules described herein can also include those that are made entirely from murine-derived sequences or fully human.

General methods of preparing such microbe-binding molecules are well known in the art (Ashkenazi, A. and S. M. Chamow (1997), "Immunoadhesins as research tools and therapeutic agents," Curr. Opin. Immunol. 9(2): 195-200, Chamow, S. M. and A. Ashkenazi (1996). "Immunoadhesins: principles and applications," Trends Biotechnol. 14(2):52-60). In one example, an engineered microbe-binding molecule can be made by cloning into an expression vector such as Fc-X vector as discussed in Lo et al. (1998) 11:495 and PCT application no. PCT/US2011/021603, filed Jan. 19, 2011, content of both of which is incorporated herein by reference.

In some embodiments, the microbe-binding molecule is a fusion protein or peptide comprising (a) a carbohydrate recognition domain derived from a carbohydrate binding protein, and (b) a linker as defined below. In some embodiments, the fusion protein or peptide further comprise a substrate binding domain at one of its terminus (e.g., N-terminus), which permits a microbe-binding molecule to attach to a solid substrate such that the carbohydrate recognition domain points away from the solid substrate surface.

In one embodiment, the microbe-binding molecule comprises an MBL, a carbohydrate recognition domain of an MBL, or a genetically engineered version of MBL (FcMBL) as described in the International Application Publication Nos. WO/2011/090954 (corresponding U.S. patent application Ser. No. 13/574,191 entitled "Engineered opsonin for pathogen detection and treatment") and WO/2013/012924 (corresponding U.S. patent application Ser. No. 14/233,553 entitled "Engineered microbe-targeting molecules and uses thereof"), contents of both of which are incorporated herein by reference. Amino acid sequences for MBL and engineered MBL are:

```
(i) MBL full length (SEQ ID NO. 1):
MSLFPSLPLL LLSMVAASYS ETVTCEDAQK TCPAVIACSS

PGINGFPGKD GRDGTKGEKG EPGQGLRGLQ GPPGKLGPPG

NPGPSGSPGP KGQKGDPGKS PDGDSSLAAS ERKALQTEMA

RIKKWLTFSL GKQVGNKFFL TNGEIMTFEK VKALCVKFQA

SVATPRNAAE NGAIQNLIKE EAFLGITDEK TEGQFVDLTG

NRLTYTNWNE GEPNNAGSDE DCVLLLKNGQ WNDVPCSTSH

LAVCEFPI (ii) MBL without the signal sequence
(SEQ ID NO. 2):
ETVTCEDAQK TCPAVIACSS PGINGFPGKD GRDGTKGEKG

EPGQGLRGLQ GPPGKLGPPG NPGPSGSPGP KGQKGDPGKS

PDGDSSLAAS ERKALQTEMA RIKKWLTFSL GKQVGNKFFL

TNGEIMTFEK VKALCVKFQA SVATPRNAAE NGAIQNLIKE

EAFLGITDEK TEGQFVDLTG NRLTYTNWNE GEPNNAGSDE

DCVLLLKNGQ WNDVPCSTSH LAVCEFPI (iii) Truncated MBL (SEQ ID NO. 3):
AASERKALQT EMARIKKWLT FSLGKQVGNK FFLTNGEIMT

FEKVKALCVK FQASVATPRN AAENGAIQNL IKEEAFLGIT

DEKTEGQFVD LTGNRLTYTN WNEGEPNNAG SDEDCVLLLK

NGQWNDVPCS TSHLAVCEFP I (iv) Carbohydrate recognition domain
(CRD) of MBL (SEQ ID NO. 4):
VGNKFFLTNG EIMTFEKVKA LCVKFQASVA TPRNAAENGA

IQNLIKEEAF LGITDEKTEG QFVDLTGNRL TYTNWNEGEP

NNAGSDEDCV LLLKNGQWND VPCSTSHLAV CEFPI (v) Neck + Carbohydrate recognition
domain of MBL (SEQ ID NO. 5):
PDGDSSLAAS ERKALQTEMA RIKKWLTFSL GKQVGNKFFL

TNGEIMTFEK VKALCVKFQA SVATPRNAAE NGAIQNLIKE

EAFLGITDEK TEGQFVDLTG NRLTYTNWNE GEPNNAGSDE

DCVLLLKNGQ WNDVPCSTSH LAVCEFPI (vi) FcMBL.81 (SEQ ID NO. 6):
EPKSSDKTHT CPPCPAPELL GGPSVFLFPP KPKDTLMISR

TPEVTCVVVD VSHEDPEVKFNWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTPPVLDSDGSFF LYSKLTVDKS

RWQQGNVFSC SVMHEALHNH YTQKSLSLSP

GAPDGDSSLAASERKALQTE MARIKKWLTF SLGKQVGNKF

FLTNGEIMTF EKVKALCVKF QASVATPRNA AENGAIQNLI

KEEAFLGITD EKTEGQFVDL TGNRLTYTNW NEGEPNNAGS

DEDCVLLLKN GQWNDVPCST SHLAVCEFPI (vii) Akt-FcMBL (SEQ ID NO. 7):
AKTEPKSSDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GAPDGDSSLA

ASERKALQTE MARIKKWLTF SLGKQVGNKF FLTNGEIMTF

EKVKALCVKF QASVATPRNA AENGAIQNLI KEEAFLGITD

EKTEGQFVDL TGNRLTYTNW NEGEPNNAGS DEDCVLLLKN

GQWNDVPCST SHLAVCEFPI (viii) FcMBL.111 (SEQ ID NO. 8):
EPKSSDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GATSKQVGNKF

FLTNGEIMTF EKVKALCVKF QASVATPRNA AENGAIQNLI

KEEAFLGITD EKTEGQFVDL TGNRLTYTNW NEGEPNNAGS

DEDCVLLLKN GQWNDVPCST SHLAVCEFPI
```

In some embodiments, microbe-binding molecule comprises an amino acid sequence selected from SEQ ID NO. 1-SEQ ID NO. 8.

In some embodiments, microbe-binding agent is a "microbe-binding substrate" as defined herein.

Linkers

As used herein, the term "linker" generally refers to a molecular entity that can directly or indirectly connect two parts of a composition, e.g., at least one microbe-binding molecule and at least one substrate-binding domain or at least one enzyme and at least one microbe-binding molecule. In some embodiments, the linker can directly or indirectly connect to one or more microbe-binding molecule or microbe-binding domain.

Linkers can be configures according to a specific need, e.g., based on at least one of the following characteristics. By way of example only, in some embodiments, linkers can be configured to have a sufficient length and flexibility such that it can allow for a microbe surface-binding domain to orient accordingly with respect to at least one carbohydrate on a microbe surface. In some embodiments, linkers can be configured to allow multimerization of at least two engineered microbe-binding molecules (e.g., to from a di-, tri-, tetra-, penta-, or higher multimeric complex) while retaining biological activity (e.g., microbe-binding activity). In some embodiments, linkers can be configured to facilitate expression and purification of the engineered microbe-binding molecule described herein. In some embodiments, linkers can be configured to provide at least one recognition-site for proteases or nucleases. In addition, linkers should be non-reactive with the functional components of the engineered molecule described herein (e.g., minimal hydrophobic or charged character to react with the functional protein domains such as a microbe surface-binding domain or a substrate-binding domain).

In some embodiments, a linker can be configured to have any length in a form of a peptide, a protein, a nucleic acid (e.g., DNA or RNA), or any combinations thereof. In some embodiments, the peptide or nucleic acid linker can vary from about 1 to about 1000 amino acids long, from about 10 to about 500 amino acids long, from about 30 to about 300 amino acids long, or from about 50 to about 150 amino acids long. Longer or shorter linker sequences can be also used for the engineered microbe-binding molecules described herein. In one embodiment, the peptide linker has an amino acid sequence of about 200 to 300 amino acids in length.

In some embodiments, a peptide or nucleic acid linker can be configured to have a sequence comprising at least one of the amino acids selected from the group consisting of glycine (Gly), serine (Ser), asparagine (Asn), threonine (Thr), methionine (Met) or alanine (Ala), or at least one of codon sequences encoding the aforementioned amino acids (i.e., Gly, Ser, Asn, Thr, Met or Ala). Such amino acids and corresponding nucleic acid sequences are generally used to provide flexibility of a linker. However, in some embodiments, other uncharged polar amino acids (e.g., Gln, Cys or Tyr), nonpolar amino acids (e.g., Val, Leu, Ile, Pro, Phe, and Trp), or nucleic acid sequences encoding the amino acids thereof can also be included in a linker sequence. In alternative embodiments, polar amino acids or nucleic acid sequence thereof can be added to modulate the flexibility of a linker. One of skill in the art can control flexibility of a linker by varying the types and numbers of residues in the linker. See, e.g., Perham, 30 Biochem. 8501 (1991); Wriggers et al., 80 Biopolymers 736 (2005).

In alternative embodiments, a linker can be a chemical linker of any length. In some embodiments, chemical linkers can comprise a direct bond or an atom such as oxygen or sulfur, a unit such as NH, C(O), C(O)NH, SO, SO2, SO2NH, or a chain of atoms, such as substituted or unsubstituted C1-C6 alkyl, substituted or unsubstituted C2-C6 alkenyl, substituted or unsubstituted C2-C6 alkynyl, substituted or unsubstituted C6-C12 aryl, substituted or unsubstituted C5-C12 heteroaryl, substituted or unsubstituted C5-C12 heterocyclyl, substituted or unsubstituted C3-C12 cycloalkyl, where one or more methylenes can be interrupted or terminated by O, S, S(O), SO2, NH, or C(O). In some embodiments, the chemical linker can be a polymer chain (branched or linear).

In some embodiments where the linker is a peptide, such peptide linker can comprise at least a portion of an immunoglobulin, e.g., IgA, IgD, IgE, IgG and IgM including their subclasses (e.g., IgG1), or a modified thereof. In some embodiments, the peptide linker can comprise a portion of fragment crystallization (Fc) region of an immunoglobulin or a modified thereof. In such embodiments, the portion of the Fc region that can be used as a linker can comprise at least one region selected from the group consisting of a hinge region, a CH2 region, a CH3 region, and any combinations thereof. By way of example, in some embodiments, a CH2 region can be excluded from the portion of the Fc region as a linker. In one embodiment, Fc linker comprises a hinge region, a CH2 domain and a CH3 domain. Such Fc linker can be used to facilitate expression and purification of the engineered microbe-binding molecules described herein. The N terminal Fc has been shown to improve expression levels, protein folding and secretion of the fusion partner. In addition, the Fc has a staphylococcal protein A binding site, which can be used for one-step purification protein A affinity chromatography. See Lo K M et al. (1998) Protein Eng. 11: 495-500. Further, such Fc linker have a molecule weight above a renal threshold of about 45 kDa, thus reducing the possibility of engineered microbe-binding molecules being removed by glomerular filtration. Additionally, the Fc linker can allow dimerization of two engineered microbe-binding molecules to form a dimer, e.g., a dimeric MBL molecule.

In various embodiments, the N-terminus or the C-terminus of the linker, e.g., the portion of the Fc region, can be modified. By way of example only, the N-terminus or the C-terminus of the linker can be extended by at least one additional linker described herein, e.g., to provide further flexibility, or to attach additional molecules. In some embodiments, the N-terminus of the linker can be linked directly or indirectly (via an additional linker) with a substrate-binding domain adapted for orienting the carbohydrate recognition domain away from the substrate. Exemplary Fc linked MBL (FcMBL and Akt-FcMBL) are described in PCT application no. PCT/US2011/021603, filed Jan. 19, 2011, content of which is incorporated herein by reference.

In some embodiments, the linker can be embodied as part of the microbe surface-binding domain, or part of the microbe surface-binding domain.

In some embodiments, the distance between the microbe surface-binding domain and the substrate surface can range from about 50 angstroms to about 5000 angstroms, from about 100 angstroms to about 2500 angstroms, or from about 200 angstroms to about 1000 angstroms.

In some embodiments, the linkers can be branched. For branched linkers, the linker can linked together at least one (e.g., one, two, three, four, five, six, seven, eight, nine, ten or more) surface binding domain and at least one (e.g., one, two, three, four, five, six, seven, eight, nine, ten or more) microbe surface-binding domain.

In some embodiments provided herein, the linker can further comprise a detectable label. In some embodiments, the detectable label can be a chromogenic or fluorogenic microbe enzyme substrate so that when a microbe binds to the engineered microbe-binding molecule, the enzyme that the microbe releases can interact with the detectable label to induce a color change. Examples of such microbe enzyme substrate can include, but are not limited to, indoxyl butyrate, indoxyl glucoside, esculin, magneta glucoside, red-β-glucuronide, 2-methoxy-4-(2-nitrovinyl) phenyl β-D-glu-copyranoside, 2-methoxy-4-(2-nitrovinyl) phenyl β-D-cetamindo-2-deoxyglucopyranoside, and any other art-recognized microbe enzyme substrates. Such embodiments can act as an indicator for the presence of a microbe or pathogen.

Exemplary Microbes or Pathogens that can be Detected or Captured Using the Methods, Compositions, Kits and Systems Described Herein As used interchangeably herein, the terms "microbes" and "pathogens" generally refer to microorganisms, including bacteria, fungi, protozoan, archaea, protists, e.g., algae, and a combination thereof. The term "microbes" also includes pathogenic microbes, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria causing diseases such as sepsis. The term "microbe" or "microbes" can also encompass non-pathogenic microbes, e.g., some microbes used in industrial applications.

In some embodiments, the term "microbe" or "microbes" also encompasses fragments of microbes, e.g., cell components of microbes, LPS, and/or endotoxin.

One skilled in the art can understand that the method described herein can be used to determine the antibiotic susceptibility of any microorganism.

In some other embodiments, the method described herein can be used to determine the antibiotic susceptibility of at least one of the following pathogens that causes diseases: *Bartonella henselae, Borrelia burgdorferi, Campylobacter jejuni, Campylobacterfetus, Chlamydia trachomatis, Chlamydia pneumoniae, Chylamydia psittaci, Simkania negevensis, Escherichia coli* (e.g., O157:H7 and K88), *Ehrlichia chafeensis, Clostridium botulinum, Clostridium perfringens, Clostridium tetani, Enterococcus faecalis, Haemophilius influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum, Human rhinovirus, Human coronavirus,* Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B 19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida, Cryptooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi,* among other viruses, bacteria, archaea, protozoa, and fungi).

In some embodiments, the method described herein can be used to determine the antibiotic susceptibility of a bacteria present in a biofilm. For example, *Listeria monocytogenes* can form biofilms on a variety of materials used in food processing equipment and other food and non-food contact surfaces (Blackman, J Food Prot 1996; 59:827-31; Frank, J Food Prot 1990; 53:550-4; Krysinski, J Food Prot 1992; 55:246-51; Ronner, J Food Prot 1993; 56:750-8). Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990: 195-231; Costerton et al., Annu Rev Microbiol 1995; 49:711-45).

In some embodiments, the method described herein can be used to determine the antibiotic susceptibility of a plant pathogen. Plant fungi have caused major epidemics with huge societal impacts. Examples of plant fungi include, but are not limited to, *Phytophthora infestans, Crinipellis perniciosa,* frosty pod (*Moniliophthora roreri*)*, oomycete Phytophthora capsici, Mycosphaerella fijiensis, Fusarium Ganoderma* spp fungi and *Phytophthora*. An exemplary plant bacterium includes *Burkholderia cepacia*. Exemplary plant viruses include, but are not limited to, soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus.

In yet other embodiments, the method described herein can be used to determine the antibiotic susceptibility of bioterror agents (e.g., B. *Anthracis*, and smallpox).

Embodiments of various aspects described herein can be defined in any of the following numbered paragraphs:

1. A method of detecting or capturing at least one target entity comprising:
   contacting a sample with a composition comprising a target-binding agent and a blocking agent bound thereto,
   wherein the blocking agent is selected for reducing the binding of at least one interfering agent present in the sample to the target-binding agent, while permitting a first target entity, if present in the sample, to (a) displace the blocking agent bound to the target-binding agent, or to (b) bind to the target-binding agent without the blocking agent bound thereto.
2. The method of paragraph 1, wherein the blocking agent is selected to have an effective binding affinity for the target-binding agent that is lower than the effective binding affinity of the first target entity for the target-binding agent; and wherein the blocking agent is selected to have the effective binding affinity for the target-binding agent that is higher than the effective binding affinity of at least one interfering agent present in the sample for the target-binding agent.
3. The method of paragraph 1 or 2, wherein the effective binding affinity of the blocking agent is a function of properties comprising surface composition of the blocking agent, avidity, single-bond affinity or affinity, surface composition of the target-binding agent, concentration of the blocking agent, concentration of the first target entity in the sample, concentration of said at least one interfering agent, or any combinations thereof.
4. The method of any of paragraphs 1-3, wherein the effective binding affinity of the first target entity is a function of properties comprising surface composition of the first target entity, avidity, single-bond affinity or affinity, surface composition of the target-binding agent, concentration of the blocking agent, concentration of the first target entity in the sample, concentration of said at least one interfering agent, or any combinations thereof.
5. The method of any of paragraphs 1-4, wherein the effective binding affinity of said at least one interfering agent is a function of properties comprising composition of the interfering agent, avidity, single-bond affinity or affinity, surface composition of the target-binding agent, concentration of the blocking agent, concentration of the first target entity in the sample, concentration of said at least one interfering agent, or any combinations thereof.
6. The method of any of paragraphs 1-5, wherein the first target entity is a microbe or a fragment thereof.
7. The method of any of paragraphs 1-6, wherein the target-binding agent comprises a microbe-binding agent.
8. The method of paragraph 7, wherein the microbe-binding agent comprises a lectin (e.g., a FcMBL molecule).
9. The method of any of paragraphs 1-8, wherein the blocking agent is a saccharide.
10. The method of any of paragraphs 1-9, wherein the blocking agent is a monomer, which has no free binding site after binding to the target-binding agent.
11. The method of paragraph 10, wherein the monomer is a monosaccharide or modification thereof.
12. The method of any of paragraphs 1-9, wherein the blocking agent is a multimer which has at least one free binding site after binding to the target-binding agent.
13. The method of paragraph 12, wherein the multimer is a disaccharide, an oligosaccharide, a polysaccharide, modifications thereof, or any combinations thereof.
14. The method of any of paragraphs 9-13, wherein the saccharide is selected from the group consisting of hexose (e.g., glucose), mannose, maltose, N-acetyl-muramic acid, amino sugars (e.g., galactosamine, glucosamine, sialic acid, N-acetylgludosamine), sulfosugars (e.g., sulfoquinovose), trehalose, cellobiose, lactose, lactulose, sucrose, fructo-oligosaccharides, cellulose, chitin, or any combinations thereof.
15. The method of paragraph 14, wherein the saccharide is selected from the group consisting of glucose, maltose, N-acetyl-muramic acid, or any combinations thereof.
16. The method of any of paragraphs 1-15, wherein the blocking agent comprises glucose.
17. The method of any of paragraphs 1-16, wherein said at least one interfering agent is a blood cell and/or a fragment thereof present in the sample, e.g., a red blood cell (or an erythryocyte) and/or a fragment thereof.
18. The method of any of paragraphs 1-16, wherein said at least one interfering agent is a second target entity to be captured or detected.
19. The method of any of paragraphs 1-16, wherein said at least one interfering agent is a non-specific binding molecule, or a specific but lower affinity binding molecule.
20. The method of any of paragraphs 1-19, wherein the effective binding affinity of the blocking agent for the target-binding agent is lower than the effective binding affinity of the first target entity for the target-binding agent by at least about 10%.
21. The method of any of paragraphs 1-20, wherein the effective binding affinity of the blocking agent for the target-binding agent is higher than the effective binding affinity of at least one interfering agent present in the sample for the target-binding agent by at least about 10%.
22. The method of any of paragraphs 1-21, wherein the effective binding affinity of the blocking agent for the target-binding agent is selected for increasing specificity of the target-binding agent to the first target entity in the sample, as compared to the specificity in the absence of the blocking agent.
23. The method of any of paragraphs 1-22, wherein the effective binding affinity of the blocking agent for the target-binding agent, as indicated by a dissociation constant for the binding of the blocking agent to the target-binding agent, ranges from about 1 nM to about 500 mM, or about 1 µM to about 100 mM, or about 1 mM to about 50 mM.
24. The method of any of paragraphs 1-23, wherein the effective binding affinity of the first target entity for the target-binding agent, as indicated by a dissociation constant for the binding of the first target entity to the target-binding agent, is less than 25 mM, less than 1 mM, less than 1 µM, or less than 1 nM.
25. The method of any of paragraphs 1-24, wherein the effective binding affinity of said at least one interfering agent for the target-binding agent, as indicated by a dissociation constant for the binding of the interfering agent to the target-binding agent, is more than 500 µM, or more than 1 mM, or more than 10 mM.
26. The method of any of paragraphs 1-25, wherein the blocking agent is present in a pre-determined concentration that does not reduce the binding of the first target entity to the target-binding agent by more than 30%, as compared to the binding in the absence of the blocking agent.
27. The method of any of paragraphs 1-26, wherein the pre-determined concentration of the blocking agent is sufficient to not decrease detection sensitivity of the target-binding agent binding to the first target entity in the sample by at least about 10%, when compared to the detection sensitivity in the absence of the blocking agent.
28. The method of any of paragraphs 1-27, further comprising exposing the target-binding agent to the blocking agent at the pre-determined concentration to form the composition comprising the target-binding agent and the blocking agent bound thereto.
29. The method of any of paragraphs 1-28, further comprising a competitive washing to release said at least one interfering agent that is bound to the target-binding agent after the contacting.
30. The method of any of paragraphs 1-29, further comprising separating the target-binding agent from the sample after the contacting.
31. The method of any of paragraphs 1-30, further comprising detecting the displaced blocking agent.
32. The method of any of paragraphs 1-31, wherein the blocking agent comprises a detectable label.

33. The method of any of paragraphs 1-32, further comprising detecting the first target entity that is bound to the target-binding agent.
34. The method of paragraph 33, wherein the first target entity that is bound to the target-binding agent is detected by a method comprising contacting the bound first target entity with a detection agent.
35. The method of any of paragraphs 1-34, wherein the sample is selected from the group consisting of a biological sample (e.g., bodily fluids such as blood, cells, tissue samples), an environmental sample, a cell culture sample, a blood culture, water, pharmaceutical preparations, foods, beverages, and any combinations thereof.
36. The method of any of paragraphs 1-35, wherein the sample is a fluid sample.
37. The method of paragraph 36, wherein the fluid sample comprises blood or serum.
38. The method of any of paragraphs 1-37, wherein the sample comprises or is attached to a solid substrate.
39. The method of any of paragraphs 1-38, wherein the composition comprises a solid substrate affixed with the target-binding agent.
40. The method of paragraph 38 or 39, wherein the solid substrate is selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge and any combinations thereof.
41. The method of any of paragraphs 1-40, wherein the target-binding agent, the blocking agent and the first target entity are each independently selected from the group consisting of cells, peptides, polypeptides, proteins, peptidomimetics, antibodies, antibody fragments (e.g., antigen binding fragments of antibodies), carbohydrate-binding protein, e.g., lectins, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, endotoxins (e.g., bacterial lipopolysaccharide), and any combinations thereof.
42. The method of paragraph 41, wherein the cells are selected from the group consisting of prokaryotes (e.g., microbes such as bacteria) and eukaryotes (e.g., animal cells, plant cells, yeasts, fungi), blood cells, and any fragments thereof.
43. A composition comprising a target-binding agent and at least one blocking agent at a pre-determined concentration, wherein the effective binding affinity of said at least one blocking agent for the target-binding agent is lower than the effective binding affinity of a target entity to be captured, and wherein the effective binding affinity of said at least one blocking agent for the target-binding agent is higher than the effective binding affinity of at least one interfering molecule present in a sample to be assayed for the target-binding agent.
44. The composition of paragraph 43, said at least one blocking agent is pre-bound to the target-binding agent.
45. The composition of paragraph 43 or 44, wherein the target-binding agent and said at least one blocking agent are present in a buffered solution.
46. The composition of any of paragraphs 43-45, further comprising a solid substrate affixed with the target-binding agent.
47. The composition of paragraph 46, wherein the solid substrate is selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combinations thereof.
48. The composition of any of paragraphs 43-47, wherein said at least one interfering agent is a second target molecule to be captured or detected.
49. The composition of any of paragraphs 43-48, wherein said at least one interfering agent is a non-specific binding molecule, or a specific but lower affinity binding molecule.
50. The composition of any of paragraphs 43-49, wherein the target-binding agent, the blocking agent, and said at least one interfering agent are each independently selected from the group consisting of peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptide aptamers, peptidoglycan, lipopolysaccharide, small molecules, endotoxins (e.g., bacterial lipopolysaccharide), cells, and any combinations thereof.
51. The composition of any of paragraphs 43-50, wherein the target-binding agent comprises an antibody.
52. The composition of any of paragraphs 43-50, wherein the target-binding agent comprises a microbe-binding agent.
53. The composition of paragraph 52, wherein the microbe-binding agent comprises a lectin (e.g., a FcMBL molecule).
54. The composition of any of paragraphs 43-53, wherein said at least one blocking agent comprises glucose, maltose, N-acetyl-muramic acid, or any combinations thereof.
55. The composition of any of paragraphs 43-54, wherein said at least one blocking agent comprises glucose.
56. The composition of paragraph 55, wherein the pre-determined concentration of glucose ranges from about 5 mM to about 200 mM.
57. The composition of any of paragraphs 43-56, wherein said at least one blocking agent comprises a detectable label.
58. A kit (for multiplexing) comprising:
    a first composition comprising a first target-binding agent and at least one first blocking agent at a first pre-determined concentration, wherein the effective binding affinity of said at least one first blocking agent for the first target-binding agent is lower than the effective binding affinity of a first target entity to be captured, and wherein the effective binding affinity of said at least one first blocking agent for the first target-binding agent is higher than the effective binding affinity of at least one first interfering molecule present in a sample to be assayed for the first target-binding agent; and
    instructions for using the composition for detecting or capturing the first target entity.

59. The kit of paragraph 58, further comprising:
    a second composition comprising a second target-binding agent and optionally at least one second blocking agent at a second pre-determined concentration, wherein the effective binding affinity of said at least one second blocking agent for the second target-binding agent is lower than the effective binding affinity of a second target entity to be captured, and wherein the effective binding affinity of said at least one second blocking agent for the second target-binding agent is higher than the effective binding affinity of at least one second interfering molecule present in the sample to be assayed for the second target-binding agent.
60. The kit of paragraph 58 or 59, wherein said at least the first interfering agent and said at least the second interfering agent are the same.
61. The kit of any of paragraphs 59-60, wherein said at least the first interfering agent and said at least the second interfering agent are different.
62. The kit of any of paragraphs 58-60, wherein said at least the first interfering agent comprises the second target entity and/or a third target entity.
63. The kit of any of paragraphs 59-60, wherein said at least the second interfering agent comprises the first target entity and/or the third target entity.
64. The kit of any of paragraphs 59-60, wherein said at least the first interfering agent and/or said at least the second interfering agent is a non-specific binding molecule.
65. The kit of any of paragraphs 58-64, wherein the first target-binding agent is affixed to a first solid substrate.
66. The kit of paragraph 65, wherein the first solid substrate is further affixed with the second target-binding agent.
67. The kit of any of paragraphs 59-66, wherein the second target-binding agent is affixed to a second solid substrate.
68. The kit of any of paragraphs 58-67, wherein the first or the second solid substrate is selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combination thereof.
69. The kit of any of paragraphs 58-68, further comprising a first detection agent capable of binding to the first target entity.
70. The kit of any of paragraphs 59-69, further comprising a second detection agent capable of binding to the second target entity.
71. A method of detecting or capturing at least one target entity comprising:
    contacting a sample with a composition comprising a target-binding agent and a blocking agent bound thereto, wherein the blocking agent is selected for reducing the binding of at least one interfering agent present in the sample to the target-binding agent, while permitting a first target entity, if present in the sample, to (a) displace the blocking agent bound to the target-binding agent, or to (b) bind to the target-binding agent without the blocking agent bound thereto.
72. The method of paragraph 71, wherein the blocking agent is selected to have an effective binding affinity for the target-binding agent that is lower than the effective binding affinity of the first target entity for the target-binding agent; and wherein the blocking agent is selected to have the effective binding affinity for the target-binding agent that is higher than the effective binding affinity of at least one interfering agent present in the sample for the target-binding agent.
73. The method of 71 or 72, wherein the first target entity is a microbe or a fragment thereof and the target-binding agent comprises a microbe-binding agent.
74. The method of paragraph 73, wherein the microbe-binding agent comprises a carbohydrate recognition domain derived from at least one carbohydrate-binding protein selected from the group consisting of lectin, collectin, ficolin, mannose-binding lectin (MBL), maltose-binding protein, arabinose-binding protein, glucose-binding protein, *Galanthus nivalis* agglutinin, peanut lectin, lentil lectin, DC-SIGN, C-reactive protein, and any combinations thereof.
75. The method of paragraph 74, wherein the microbe-binding agent comprises an amino acid sequence selected from SEQ ID NO: 1-SEQ ID NO: 8.
76. The method of any of paragraphs 71-75, wherein the blocking agent is a monomer, the monomer having no free binding site after binding to the target-binding agent; or a multimer, the multimer having at least one free-binding site after binding to the target-binding agent.
77. The method of any of paragraphs 71-76, wherein the blocking agent is a saccharide.
78. The method of paragraph 77, wherein the saccharide is selected from the group consisting of hexose, glucose, mannose, maltose, N-acetyl-muramic acid, amino sugars (e.g., galactosamine, glucosamine, sialic acid, N-acetyl-gludosamine), sulfosugars (e.g., sulfoquinovose), trehalose, cellobiose, lactose, lactulose, sucrose, fructo-oligosaccharides, cellulose, chitin, or any combinations thereof.
79. The method of any of paragraphs 71-78, wherein said at least one interfering agent is selected from the group consisting of
    a. a blood cell and/or a fragment thereof present in the sample, e.g., a red blood cell (or an erythrocyte) and/or a fragment thereof;
    b. a second target entity to be captured or detected;
    c. a non-specific binding molecule;
    d. a specific but low affinity binding molecule; and
    e. any combinations thereof.
80. The method of any of paragraphs 71-79, wherein the effective binding affinity of the blocking agent for the target-binding agent is measured by a dissociation constant, wherein the dissociation constant for binding of the blocking agent to the target-binding agent ranges from about 1 mM to about 50 mM.
81. The method of any of paragraphs 71-80, further comprising, prior to the contacting, exposing the target-binding agent to the blocking agent to form the composition comprising the target-binding agent and the blocking agent bound thereto.
82. The method of any of paragraphs 71-81, further comprising a competitive washing to release said at least one interfering agent that is bound to the target-binding agent after the contacting.
83. The method of any of paragraphs 71-82, further comprising separating the target-binding agent from the sample after the contacting.
84. The method of any of paragraphs 71-83, further comprising detecting the at least one target entity that is bound to the target-binding agent.
85. The method of paragraph 84, wherein the at least one target entity is detected by a method comprising contacting the bound target entity with a detection agent, wherein the detection agent does not bind to the blocking agent.

86. The method of any of paragraphs 71-85, wherein the sample is selected from the group consisting of a biological sample (e.g., bodily fluids such as blood, cells, tissue samples), an environmental sample, a cell culture sample, a blood culture, water, pharmaceutical preparations, foods, beverages, solid supports (e.g., membranes, slides, plates) comprising the at least one target entity, and any combinations thereof.

87. The method of paragraph 86, wherein the sample is a fluid sample comprising blood or serum.

88. The method of any of paragraphs 71-87, wherein the target-binding agent is attached to a solid substrate.

89. The method of paragraph 88, wherein the solid substrate is selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combinations thereof.

90. A composition comprising a target-binding agent and a blocking agent, wherein the effective binding affinity of the blocking agent for the target-binding agent is lower than the effective binding affinity of a target entity to be captured, and wherein the effective binding affinity of the blocking agent for the target-binding agent is higher than the effective binding affinity of at least one interfering molecule present in a sample to be assayed for the target-binding agent.

91. The composition of paragraph 90, wherein the target-binding agent is a microbe-binding agent comprising a carbohydrate recognition domain derived from at least one carbohydrate-binding protein selected from the group consisting of lectin, collectin, ficolin, mannose-binding lectin (MBL), maltose-binding protein, arabinose-binding protein, glucose-binding protein, *Galanthus nivalis* agglutinin, peanut lectin, lentil lectin, DC-SIGN, C-reactive protein, and any combinations thereof.

92. The composition of paragraph 91, wherein the microbe-binding agent further comprises (i) a linker (e.g., Fc portion) linked to carbohydrate recognition domain; and optionally (ii) a substrate binding domain adapted for orienting the carbohydrate recognition domain away from a solid substrate surface.

93. The composition of paragraph 92, wherein the solid substrate is selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a mixing element (e.g., a spiral mixer), a microscopic slide, a hollow fiber, a hollow fiber cartridge, and any combinations thereof.

94. The composition of any of paragraphs 90-93, said at least one blocking agent is pre-bound to the target-binding agent.

95. The composition of any of paragraphs 90-94, wherein said at least one blocking agent comprises a saccharide selected from the group consisting of hexose, glucose, mannose, maltose, N-acetyl-muramic acid, amino sugars (e.g., galactosamine, glucosamine, sialic acid, N-acetyl-gludosamine), sulfosugars (e.g., sulfoquinovose), trehalose, cellobiose, lactose, lactulose, sucrose, fructo-oligosaccharides, cellulose, chitin, and any combinations thereof.

96. A kit for differentiating a first target entity from a second target entity in a sample comprising:
a first composition comprising a first target-binding agent and a blocking agent, wherein the effective binding affinity of the blocking agent for the first target-binding agent is lower than the effective binding affinity of the first target entity for the first target-binding agent, and wherein the effective binding affinity of the blocking agent for the first target-binding agent is higher than the effective binding affinity of the second target entity for the first target-binding agent;
a second composition comprising a second target-binding agent; and
instructions for using the composition for differentiating a first target entity from a second target entity in a sample.

Some Selected Definitions

For Convenience, Certain Terms Employed in the Entire Application (Including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one aspect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these As used herein, the term "peptidomimetic" refers to a molecule capable of folding into a defined three-dimensional structure similar to a natural peptide.

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Improvement of Lectin Binding Specificity Using Competing Low Affinity Substrates (Blocking Agent)

Lectins are proteins that have binding sites for specific mono- or oligo-saccharides. Lectins recognize a range of different carbohydrates and carbohydrate-containing patterns based on a number of factors, including, e.g., the chemical nature of the carbohydrate, and/or the density or geometry of the carbohydrate relative to its tethering point. Different lectins (either native or engineered) have different affinities towards different ligands. The low affinity binding of lectins to some carbohydrate moieties limit the usefulness of lectins in many biological applications.

Accordingly, in one embodiment, presented herein is a method to improve the binding specificity of a target-binding agent comprising lectin in an assay by the addition of a blocking agent, e.g., a binding substrate of intermediate affinity, in a competitive manner. An example of a binding substrate of intermediate affinity is a binding substrate with an effective binding affinity for the target-binding agent between the effective binding affinity of a target entity (e.g., a microbe or a fragment thereof) for the target-binding agent and the effective binding affinity of an interfering agent present in a sample (e.g., a red blood cell or a fragment thereof) for the target-binding agent.

By way of example only, assuming that substance A is the preferred ligand (target entity) of a given target binding agent (e.g., lectin L), L can be used to bind A for any purpose, such as purification, detection, removal or other. However, L can also bind to a substance B with lower affinity (an interfering agent) which will impair the purification, detection, and/or removal of A by L. In a complex matrix such as blood or serum or food or other mixtures, it is often found that L binds to the more abundant B therefore decreasing the performance of L binding to A. Accordingly, some embodiments of the methods described herein relates to adding a blocking agent (e.g., carbohydrate C of intermediate affinity to L), which is preferentially bound over B but easily displaced by A, in order to improve binding specificity and/or sensitivity of L to A. The adequate choice of C is selected such that it does not interfere with the desired function assigned to L, e.g., C binding to L does not compete with the binding of A to L but prevents the binding of B to L.

In one embodiment where L is FcMBL, A is mannan, B is glucose, it is found that in a simple controlled medium where mannan is the sole carbohydrate present, FcMBL can detect mannan down to amounts equal or lower than 2 ng/ml. However, when mannan is added to a complex medium such as blood, the detection of mannan is impaired by a background, e.g., the binding of erythrocytes or other carbohydrates via the mannose binding domains on FcMBL. The binding of erythrocytes (or other carbohydrates) can impair downstream detection because bound erythrocytes generally interfere with the successive detection steps, thereby raising the detection threshold (up to 500 ng/ml or more from 2 ng/ml).

The inventors have discovered that addition of a small amount of mannan can decrease the background by preventing the binding of erythrocytes or other endogenous components from blood to FcMBL.

The inventors have also discovered that the addition of a medium affinity ligand of FcMBL such as glucose ($K_d$=23 mM), or maltose ($K_d$=15 mM) or N-acetyl Muramic acid (MurNAc, $K_d$=17 mM) to FcMBL prior to the capture of mannan in the presence of blood decreases the background of the FcMBL ELISA. Without wishing to be bound by theory, this reduced background can be related to the prevention of FcMBL low affinity binding to erythrocytes (or other endogenous components in blood) by the medium affinity sugar that in turn can be displaced by the higher affinity targets such as mannan, lipopolysaccharides (LPS), and/or a microbe or fragment thereof.

As shown in FIG. 1, the addition of ~10 mM glucose does not adversely affect mannan binding in buffer, whereas ~20 mM glucose effectively reduces the mannan binding by ~50% and ~40 mM glucose almost abolishes the mannan binding in buffer. Further, the addition of ~10 mM glucose decreases non-specific binding of FcMBL to blood without affecting the detection of mannan in donor blood. Accordingly, the concentration of a blocking agent (e.g., glucose) for use in an assay (e.g., FcMBL assay) is selected such that the presence of the blocking agent (e.g., glucose) does not significantly affect target binding (e.g., mannan binding in this Example), while sufficient to prevent the binding of interfering agents (e.g., erythrocytes) to a target-binding agent (e.g., FcMBL).

FcMBL also has a high affinity for bacterial lipopolysaccharide (LPS) also known as endotoxin. As shown in FIG. 2, competition assays show that higher concentrations of glucose are required to effectively compete for binding to FcMBL. Unlike mannan detection, the addition of ~40 mM glucose or ~80 mM glucose does not significantly affect the detection of LPS in serum. When glucose was added at a concentration of about 160 mM, the LPS detection was reduced to 10% as compared to the detection level determined in the absence of glucose.

FIG. 3A shows that the addition of glucose reduces the background noise contributed by interfering agents present in donor blood, thereby increasing the specificity of FcMBL binding to LPS, as evidenced by decreasing $OD_{450}$ signal as the concentration of LPS spiked in donor blood decreases.

Further, FIG. 3B shows that the addition of glucose significantly decreases the binding of haemocytes (e.g., erythrocytes) to FcMBL in donor blood.

Figure 4:
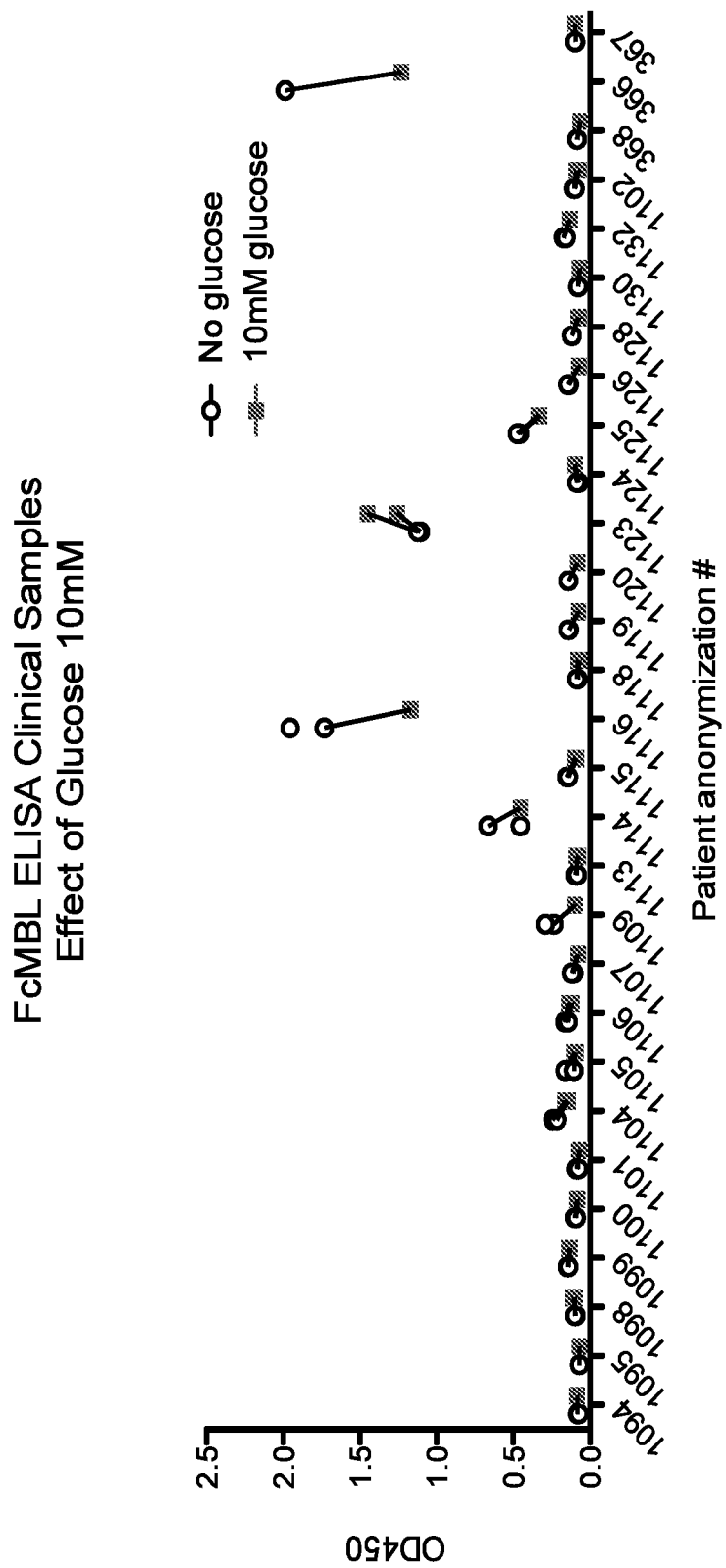
FIG. 4 is data graph showing effects of adding a blocking agent (e.g., ~10 mM glucose) on binding of a microbe or a fragment thereof to a target-binding agent (e.g., FcMBL) in clinical samples. The microbial detection was determined by FcMBL ELISA.

In addition to reduced background, the presence of a medium affinity target (e.g., but not limited to glucose) for capture can be used to reduce false positives in the assays resulting from captured non-target materials such as erythrocytes. For example, as shown in FIG. 4, the FcMBL ELISA assay indicates that a microbe is detected in a clinical sample of patient 1109, when the assay was performed without addition of a blocking agent (e.g., glucose). However, the positive microbial detection disappeared when the assay was performed in the presence of a blocking agent (e.g., glucose) at an appropriate concentration (e.g., ~10 mM). The addition of glucose can prevent binding of non-target materials such as erythrocytes from binding to FcMBL, which would otherwise contribute to a false-positive.

In some embodiments, the competition of a blocking agent (e.g., glucose) over an interfering agent (e.g., erythrocytes) can also permit the inclusion of at least one competitive wash step to release the interfering agent (e.g., erythrocytes) that are still bound to the target-binding agent (e.g., FcMBL), thereby increasing the stringency/sensitivity of the detection reaction. For example, after contacting a sample with a composition comprising a target-binding agent (e.g., FcMBL) and a blocking agent (e.g., glucose) bound to the target-binding agent (e.g., FcMBL), the mixture can be washed with a wash buffer comprising a blocking agent (e.g., glucose) so as to remove any residual interfering agent (e.g., erythrocytes) not competed away by the target-binding agent (e.g., FcMBL), e.g., due to low abundance of the target-binding agent (e.g., FcMBL).

The methods described herein comprising addition of a blocking agent to an assay are applicable to all functions performed by FcMBL in addition to microbial detection. In the use of FcMBL for depletion of microbes from blood or food, e.g., for detection purposes, glucose can be added to a storage buffer and prebound to FcMBL. The high affinity binding of the captured microorganism can displace the blocking agent (e.g., sugar such as glucose) and prevent undesirable binding of blood cells etc., that would interfere with downstream detection processes, e.g., ATP-based detection of viable bacteria or downstream genetic amplification efficiency or immunoenzymatic detection. While performing an assay using a dialysis-like therapeutic (DLT) device, e.g., as described in the International Application Publication No. WO 2012/135834, the content of which is incorporated herein by reference, FcMBL beads or membrane can be preloaded with a blocking agent (e.g., glucose or maltose etc.) to not only enhance the capture of pathogens and microbial carbohydrate compounds but also to enhance magnetic bead recovery and prevent FcMBL inactivation by low affinity binders such as erythrocytes.

The addition of a blocking agent to a test sample in a competitive manner can be applied to any other protein-ligand system where low affinity binders interfere. For example, in an antibody (Ab)-based assay, some common interfering epitopes are low affinity binders and can compromise the assay.

In one embodiment, the addition of a blocking agent to a test sample in a competitive manner can be used in immunoglobulin secondary detection reactions. An example of such an application is described below: Fluorescent-labeled IgG1 has been raised to detect rabbit F(c) fragment for which IgG1 has high affinity. However, IgG1 also has a low affinity to goat F(c) and a medium affinity to an aptamer derived from the rabbit F(c) epitope. Thus, incubating HRP-labeled IgG1 in multiplex labeling assay where a goat primary Ab and a rabbit primary Ab are both used can result in the fluorescent labeling of both the goat and rabbit primary Abs.

In order to distinguish the labeling of both the goat and rabbit primary Abs, fluorescent-labeled IgG1 can be incubated with the aptamers (derived from the rabbit F(c) epitope) with a medium affinity prior to addition into a multiplex labeling assay where both a goat primary Ab and a rabbit are used. In this example, the high affinity ligand A is the rabbit Ab, the low affinity undesirable ligand B is the goat Ab and the intermediate affinity ligand C is the aptamer. The rabbit Ab (A) can displace the aptamers (C) that are bound to the fluorescent-labeled IgG1 but the goat Ab (B) is less likely to bind to the fluorescent-labeled IgG1 because the fluorescent-labeled IgG1 has already bound to the aptamers, which cannot be displaced by the goat Ab (B) with lower affinity. In some embodiments, the goat Ab (B) that is not bound to the first fluorescent-labeled IgG1 can be then detected with another fluorescent-labeled IgG1, thus enabling detection of different target entities in a multiplex labeling assay, e.g., using the same detection agent (e.g., IgG1) but with a different detectable label (e.g., a different fluorescent label) for each target entity (e.g., rabbit Ab and goat Ab).

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of capturing at least one target entity in a sample, the method comprising:
    contacting a sample with a composition comprising a target-binding agent attached to a solid substrate, the target-binding agent having a blocking agent bound thereto, wherein the blocking agent comprises a hexose, and wherein the target-binding agent comprises a mannan-binding lectin (MBL) consisting of an amino acid sequence selected from the group consisting of SEQ ID NO: 1-SEQ ID NO: 8; and
    allowing the target entity, wherein the target entity comprises a microbe or a microbial fragment, to displace the blocking agent and to bind to the target-binding agent, thereby capturing the target entity comprising a microbe or the microbial fragment.

2. The method of claim 1, wherein the sample comprises blood and the blocking agent has an effective binding affinity for the target-binding agent that is lower than an effective binding affinity of the microbe or the microbial fragment for the target-binding agent, and that is higher than the effective binding affinity of a blood cell or a fragment thereof for the target-binding agent.

3. The method of claim 1, wherein the blocking agent is a monomer, the monomer having no free binding site after binding to the target-binding agent.

4. The method of claim 1, wherein the blocking agent is a multimer, the multimer having at least one free-binding site after binding to the target-binding agent.

5. The method of claim 1, wherein the blocking agent comprises glucose.

6. The method of claim 1, wherein the blocking agent inhibits binding of the target-binding agent to a blood cell or a fragment thereof present in the sample prior to the binding of the microbe or the microbial fragment to the target-binding agent.

7. The method of claim 1, wherein the effective binding affinity of the blocking agent for the target-binding agent is characterized by a dissociation constant, wherein the dissociation constant ranges from about 1 mM to about 50 mM.

8. The method of claim 7, wherein the blocking agent is pre-bound to the target-binding agent prior to the contacting.

9. The method of claim 1, further comprising separating the target-binding agent from the sample after the microbe or the microbial fragment is captured on the target-binding agent.

10. The method of claim 1, further comprising detecting the microbe or the microbial fragment that is bound to the target-binding agent.

11. The method of claim 10, wherein the microbe or the microbial fragment is detected by a method comprising contacting the bound microbe or microbial fragment with a detection agent, wherein the detection agent does not bind to the blocking agent.

12. The method of claim 1, wherein target-binding agent comprises a fusion protein that includes an Fc portion of an immunoglobulin linked to the MBL (FcMBL), the Fc portion being attached to the solid support, and further wherein the blocking agent comprises a glucose bound to a carbohydrate recognition domain of the MBL to inhibit binding of a blood cell or a fragment to the target-binding agent.

13. The method of claim 1, wherein the solid substrate is selected from the group consisting of: a medical apparatus a filtration device, a membrane, a diagnostic strip, a dipstick, and an extracorporeal device.

14. The method of claim 1, wherein the solid substrate is selected from the group consisting of: a microparticle, a microbead, a nanotube, a microtiter plate, an implant, a microchip, a mixing element, a microscopic slide, a hollow fiber, and a hollow fiber cartridge.

* * * * *